(12) United States Patent
Draper et al.

(10) Patent No.: US 11,096,999 B2
(45) Date of Patent: Aug. 24, 2021

(54) TREATMENT AND PREVENTION OF MALARIA

(71) Applicant: OXFORD UNIVERSITY INNOVATION LIMITED, Oxford (GB)

(72) Inventors: Simon Draper, Oxford (GB); Matthew Higgins, Oxford (GB); Katherine Wright, Oxford (GB); Alexander Douglas, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 15/500,269

(22) PCT Filed: Jul. 30, 2015

(86) PCT No.: PCT/GB2015/052205
§ 371 (c)(1),
(2) Date: Jan. 30, 2017

(87) PCT Pub. No.: WO2016/016651
PCT Pub. Date: Feb. 4, 2016

(65) Prior Publication Data
US 2017/0209558 A1 Jul. 27, 2017

(30) Foreign Application Priority Data
Jul. 30, 2014 (GB) .................................. 1413530

(51) Int. Cl.
| | | |
|---|---|---|
| A61K 39/015 | (2006.01) |
| A61K 39/00 | (2006.01) |
| A61K 39/02 | (2006.01) |
| C07K 16/20 | (2006.01) |
| A61K 39/005 | (2006.01) |
| C07K 14/445 | (2006.01) |
| C12N 7/00 | (2006.01) |
| C12N 15/115 | (2010.01) |

(52) U.S. Cl.
CPC .......... *A61K 39/015* (2013.01); *A61K 39/005* (2013.01); *C07K 14/445* (2013.01); *C07K 16/205* (2013.01); *C12N 7/00* (2013.01); *A61K 2039/5256* (2013.01); *A61K 2039/53* (2013.01); *C07K 2319/02* (2013.01); *C12N 15/115* (2013.01); *C12N 2710/10334* (2013.01); *C12N 2710/10343* (2013.01); *C12N 2710/24033* (2013.01); *C12N 2710/24034* (2013.01); *Y02A 50/30* (2018.01)

(58) Field of Classification Search
CPC ..... A61K 39/00; A61K 39/002; A61K 39/015
USPC .......... 424/130.1, 184.1, 265.1, 269.1, 272.1
See application file for complete search history.

(56) References Cited

U.S. PATENT DOCUMENTS

| | | | |
|---|---|---|---|
| 9,181,313 B2 | 11/2015 | Douglas et al. | |
| 2013/0183332 A1* | 7/2013 | Douglas ............... | A61K 39/015 424/191.1 |
| 2014/0010816 A1 | 1/2014 | Chen et al. | |
| 2014/0093540 A1 | 4/2014 | Wright et al. | |
| 2016/0129099 A1 | 5/2016 | Douglas et al. | |

FOREIGN PATENT DOCUMENTS

| | | | | |
|---|---|---|---|---|
| WO | 2005/018665 A1 | 3/2005 | | |
| WO | 2010/022452 A1 | 3/2010 | | |
| WO | 2012046081 A1 | 4/2012 | | |
| WO | WO2012/046081 | * 4/2012 | ........... | A61K 39/015 |
| WO | 2012061882 A1 | 5/2012 | | |
| WO | 2012/114125 A2 | 8/2012 | | |
| WO | WO2012/114125 | * 8/2012 | | |
| WO | 2012172277 A1 | 12/2012 | | |
| WO | 2013/108272 A2 | 7/2013 | | |

OTHER PUBLICATIONS

Search Report for counterpart Appl. No. GB1413530.5 from United Kingdom Intellectual Property, dated Apr. 23, 2015.
International Search Report for International Appl. No. PCT/GB2015/052205, European Patent Office, dated Mar. 14, 2016.
Baum et al., Reticulocyte-binding protein homologue 5—An essential adhesin involved in invasion of human erythrocytes by Plasmodium falciparum, International Journal for Parasitology, 39:371-380 (2009).
Douglas et al., The blood-stage malaria antigen PfRH5 is susceptible to vaccine-inducible cross-strain neutralizing antibody, Nature Communications, 2:601 (2011).
Arevalo-Pinzon et al., A single amino acid change in the Plasmodium falciparum RH5 (PfRH5) human RBC binding sequence modifies its structure and determines species-specific binding activity, Vaccine, 30:637-646 (2012).
Draper et al., Enhancing Blood-Stage Malaria Subunit Vaccine Immunogenicity in Rhesus Macaques by Combining Adenovirus, Poxvirus, and Protein-In-Adjuvant Vaccines, Journal of Immunology, 185:7583-7595 (2010).

(Continued)

*Primary Examiner* — Rodney P Swartz
(74) *Attorney, Agent, or Firm* — Nevrivy Patent Law Group P.L.L.C.

(57) ABSTRACT

There are provided antigens, vectors encoding the antigens, and antibodies and other binding compounds to the antigens and uses thereof in the prevention or treatment of malaria. In particular, compositions are provided comprising fragments of Reticulocyte-binding protein Homologue 5 (PfRH5). In particular, the invention provides fragments of PfRH5 rationally designed on the basis of the PfRH5 crystal structure, wherein said fragments which lack disordered regions, particularly the flexible N-terminal region and/or flexible central linker.

16 Claims, 9 Drawing Sheets

Specification includes a Sequence Listing.

(56) References Cited

OTHER PUBLICATIONS

Wright et al., Structure of malaria invasion protein RH5 with erythrocyte basigin and blocking antibodies, Nature 515 7527:427-430 (2014).
Deans et al., Rat monoclonal antibodies which inhibit the in vitro multiplication of Plasmodium knowlesi, Clin. Exp. Immunol., 49:297-309 (1982).
Stowers et al., Vaccination of Monkeys with Recombinant Plasmodium falciparum Apical Membrane Antigen 1 Confers Protection against Blood-Stage Malaria, Infection and Immunity 70(2):6961-6967 (2002).
Singh et al., Immunity to Recombinant Plasmodium falciparum Merozoite Surface Protein 1 (MSP1): Protection in Aotus nancymai Monkeys Strongly Correlates with Anti-MSP1 Antibody Titer and In Vitro Parasite-Inhibitory Activity, Infection and Immunity, 74(8):4573-4580 (2006).
Douglas et al., A PfRH5-Based Vaccine Is Efficacious against Heterologous Strain Blood-Stage Plasmodium falciparu Infection in Aotus Monkeys, Cell Host & Microbe 17:130-139 (Jan. 2015).
Douglas et al., PfRH5 vaccine efficacy against heterologous strain bloodstage Plasmodium falciparum, The Lancet Poster, 64, p. 43 (available online Feb. 26, 2014).
Sridhar et al., Single-Dose Protection Against Plasmodium Berghei by a Simian Adenovirus Vector Using a Human Cytomegalovirus Promoter Containing Intron A, Journal of Virology, 82:3822-3833 (2008).
Rodriguez et al. PFRH5: A Novel Reticulocyte-Binding Family Homolog of Plasmodium Falciparum That Binds to the Erythrocyte, and an Investigation of Its Receptor, PLOS One, 3:E3300 (2008).
Struik et al., Does Malaria suffer from lack of memory?, Immunological Reviews 201:268-290 (2004).
Vaughn et al., Malarial vaccine development: persistent challenges, Current Opinion in Immunology, 24:324-331 (2012).
Official Communication from European Appl. No. 15747523.7, dated Apr. 4, 2018.
Official Communication from European Appl. No. 15747523.7, dated Jan. 29, 2019.
Bachmann et al., Vaccine delivery: a matter of size, geometry, kinetics and molecular patterns, Nature Reviews, (2010), 10: 787-796.
Biswas et al.,Transgene Optimization, Immunogenicity and In Vitro Efficacy of Viral Vectored Vaccines Expressing Two Alleles of Plasmodium falciparum AMA1, PLoS ONE, (2011), 6:1-16.
Bruder et al., Adenovectors induce functional antibodies capable of potent inhibition of blood stage malaria parasite growth, Vaccine, (2010) 28:3201-3210.
Bunka et al., Aptamers come of age—at last, Nature Reviews, (2006), 4: 588-596.
Miura et al., Anti-Apical-Membrane-Antigen-1 Antibody Is More Effective than Anti-42-Kilodalton-Merozoite-Surface-Protein-1 Antibody in Inhibiting Plasmodium falciparum Growth, as Determined by the In Vitro Growth Inhibition Assay, Clinical and Vaccine Immunology, (2009), 16:963-968.
Dutta et al., High Antibody Titer against Apical Membrane Antigen-1 Is Required to Protect against Malaria in the Aotus Model. PLoS ONE, (2009), 4:1-12.
Ellis et al., Phase 1 Study in Malaria Naïve Adults of BSAM2/Alhydrogel®+CPG 7909, a Blood Stage Vaccine against P. falciparum Malaria, PLOS ONE, (2012), 7:1-11.
Faber et al., Diversity Covering AMA1-MSP119 Fusion Proteins as Malaria Vaccines, Infection and Immunity, (2013), 81:1479-1490.
Forbes et al., Combining Liver- and Blood-Stage Malaria Viral-Vectored Vaccines: Investigating Mechanisms of CD8+ T Cell Interference, The Journal of Immunology, (2011), 187:3738-3750.
Geall et al., Nonviral delivery of self-amplifying RNA vaccines, PNAS, (2012), 109:14604-14609.
Goodman et al., Blood-stage malaria vaccines—recent progress and future challenges, Annals of Tropical Medicine & Parasitology, (2010),104:189-211.
Henikoff et al., Amino acid substitution matrices from protein blocks, Proc. Natl. Acad. Sci. USA, (1992), 89:10915-10919.
Hirose et al., POODLE-L: a two-level SVM prediction system for reliably predicting long disordered regions, (2007) 23:2046-2053.
Ibrahimi et al., Highly Efficient Multicistronic Lentiviral Vectors with Peptide 2A Sequences, Human Gene Therapy, (2009), 20:845-860.
Pichyangkul et al., Evaluation of the safety and immunogenicity of Plasmodium falciparum apical membrane antigen 1, merozoite surface protein 1 or RTS,S vaccines with adjuvant system AS02A administered alone or concurrently in rhesus monkeys, Vaccine, (2010), 28:452-462.
Porter et al., A human Phase I/IIa malaria challenge trial of a polyprotein malaria vaccine, Vaccine, (2011), 29:7514-7522.
Sheehy et al., Phase Ia Clinical Evaluation of the Plasmodium falciparum Blood-stage Antigen MSP1 in ChAd63 and MVA Vaccine Vectors, The American Society of Gene & Cell Therapy, Molecular Therapy, (2011),19:2269-2276.
Sheehy et al., ChAd63-MVA-vectored Blood-stage Malaria Vaccines Targeting MSP1 and AMA1: Assessment of Efficacy Against Mosquito Bite Challenge in Humans, Molecular Therapy, (2012), 20:2355-2368.
Spencer et al., Fusion of the *Mycobacterium tuberculosis* Antigen 85A to an Oligomerization Domain Enhances Its Immunogenicity in Both Mice and Non-Human Primates, PLoS ONE, (2012), 7:1-11.
Spring et al., Phase 1/2a Study of the Malaria Vaccine Candidate Apical Membrane Antigen-1 (AMA-1) Administered in Adjuvant System AS01B or AS02A, PLoS ONE, (2009), 4:1-13.
Tine et al., NYVAC-Pf7: a Poxvirus-Vectored, Multiantigen, Multistage Vaccine Candidate for Plasmodium falciparum Malaria, Infection and Immunity, (1996), 64:3833-3844.
Wu et al., Sustained high-titer antibody responses induced by conjugating a malarial vaccine candidate to outer-membrane protein complex, PNAS, (2006), 103:18243-18248.
Lyon et al., Protection Induced by Plasmodium falciparum MSP142 Is Strain-Specific, Antigen and Adjuvant Dependent, and Correlates with Antibody Responses, PLoS ONE, (2008), 3:1-11.
Miura et al., Development and characterization of a standardized ELISA including a reference serum on each plate to detect antibodies induced by experimental malaria vaccines, (2008), 26:193-200.

* cited by examiner

```
                               SEQUENCE LISTING

<160> NUMBER OF SEQ ID NOS: 14

<210> SEQ ID NO 1
<211> LENGTH: 526
<212> TYPE: PRT
<213> ORGANISM: Plasmodium falciparum

<400> SEQUENCE: 1

Met Ile Arg Ile Lys Lys Lys Leu Ile Leu Thr Ile Ile Tyr Ile His
1               5                  10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45

Glu Glu Lys Asp Asp Ile Lys Asn Gly Lys Asp Ile Lys Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
            100                 105                 110

Phe Asn Gln Ile Asn Asp Gly Met Leu Leu Asn Glu Lys Asn Asp Val
        115                 120                 125

Lys Asn Asn Glu Asp Tyr Lys Asn Val Asp Tyr Lys Asn Val Asn Phe
    130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
                165                 170                 175

Pro His Tyr Thr Phe Leu Asp Tyr Tyr Lys His Leu Ser Tyr Asn Ser
            180                 185                 190
```

```
Ile Tyr His Lys Ser Ser Thr Tyr Gly Lys Cys Ile Ala Val Asp Ala
            195                 200                 205

Phe Ile Lys Lys Ile Asn Glu Thr Tyr Asp Lys Val Lys Ser Lys Cys
210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Ser Tyr Arg Tyr Asp Ile
            245                 250                 255

Ser Glu Glu Ile Asp Asp Lys Ser Glu Thr Asp Asp Thr Glu
                260                 265                 270

Glu Val Glu Asp Ser Ile Gln Asp Thr Asp Ser Asn His Thr Pro Ser
            275                 280                 285

Asn Lys Lys Lys Asn Asp Leu Met Asn Arg Thr Phe Lys Lys Met Met
    290                 295                 300

Asp Glu Tyr Asn Thr Lys Lys Lys Leu Ile Lys Cys Ile Lys Asn
305                 310                 315                 320

His Glu Asn Asp Phe Asn Lys Ile Cys Met Asp Met Lys Asn Tyr Gly
                325                 330                 335

Thr Asn Leu Phe Glu Gln Leu Ser Cys Tyr Asn Asn Asn Phe Cys Asn
            340                 345                 350

Thr Asn Gly Ile Arg Tyr His Tyr Asp Glu Tyr Ile His Lys Leu Ile
        355                 360                 365

Leu Ser Val Lys Ser Lys Asn Leu Asn Lys Asp Leu Ser Asp Met Thr
    370                 375                 380

Asn Ile Leu Gln Gln Ser Glu Leu Leu Leu Thr Asn Leu Asn Lys Lys
385                 390                 395                 400

Met Gly Ser Tyr Ile Tyr Ile Asp Thr Ile Lys Phe Ile His Lys Glu
                405                 410                 415

Met Lys His Ile Phe Asn Arg Ile Glu Tyr His Thr Lys Ile Ile Asn
            420                 425                 430

Asp Lys Thr Lys Ile Ile Gln Asp Lys Ile Lys Leu Asn Ile Trp Arg
        435                 440                 445

Thr Phe Gln Lys Asp Glu Leu Leu Lys Arg Ile Leu Asp Met Ser Asn
450                 455                 460

Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
                485                 490                 495

Leu Ile Tyr Val Leu Gln Met Lys Phe Asn Asp Val Pro Ile Lys Met
            500                 505                 510

Glu Tyr Phe Gln Thr Tyr Lys Lys Asn Lys Pro Leu Thr Gln
        515                 520                 525

<210> SEQ ID NO 2
<211> LENGTH: 526
<212> TYPE: PRT
<213> ORGANISM: Plasmodium falciparum

<400> SEQUENCE: 2

Met Ile Arg Ile Lys Lys Lys Leu Ile Leu Thr Ile Tyr Ile His
1               5                   10                  15

Leu Phe Ile Leu Asn Arg Leu Ser Phe Glu Asn Ala Ile Lys Lys Thr
            20                  25                  30

Lys Asn Gln Glu Asn Asn Leu Thr Leu Leu Pro Ile Lys Ser Thr Glu
        35                  40                  45
```

-continued

Glu Glu Lys Asp Asp Ile Lys Asn Gly Lys Asp Ile Lys Lys Glu Ile
    50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
            100                 105                 110

Phe Asn Gln Ile Asn Asp Gly Met Leu Leu Asn Glu Lys Asn Asp Val
        115                 120                 125

Lys Asn Asn Glu Asp Tyr Lys Asn Val Asp Tyr Lys Asn Val Asn Phe
    130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
                165                 170                 175

Pro His Tyr Thr Phe Leu Asp Tyr Tyr Lys His Leu Ser Tyr Asn Ser
            180                 185                 190

Ile Tyr His Lys Ser Ser Thr Tyr Gly Lys Tyr Ile Ala Val Asp Ala
        195                 200                 205

Phe Ile Lys Lys Ile Asn Glu Thr Tyr Asp Lys Val Lys Ser Lys Cys
    210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Ser Tyr Arg Tyr Asp Ile
                245                 250                 255

Ser Glu Glu Ile Asp Asp Lys Ser Glu Glu Thr Asp Asp Glu Thr Glu
            260                 265                 270

Glu Val Glu Asp Ser Ile Gln Asp Thr Asp Ser Asn His Thr Pro Ser
        275                 280                 285

Asn Lys Lys Asn Asp Leu Met Asn Arg Thr Phe Lys Lys Met Met
    290                 295                 300

Asp Glu Tyr Asn Thr Lys Lys Lys Leu Ile Lys Cys Ile Lys Asn
305                 310                 315                 320

His Glu Asn Asp Phe Asn Lys Ile Cys Met Asp Met Lys Asn Tyr Gly
                325                 330                 335

Thr Asn Leu Phe Glu Gln Leu Ser Cys Tyr Asn Asn Asn Phe Cys Asn
            340                 345                 350

Thr Asn Gly Ile Arg Tyr His Tyr Asp Glu Tyr Ile His Lys Leu Ile
        355                 360                 365

Leu Ser Val Lys Ser Lys Asn Leu Asn Lys Asp Leu Ser Asp Met Thr
    370                 375                 380

Asn Ile Leu Gln Gln Ser Glu Leu Leu Leu Thr Asn Leu Asn Lys Lys
385                 390                 395                 400

Met Gly Ser Tyr Ile Tyr Ile Asp Thr Ile Lys Phe Ile His Lys Glu
                405                 410                 415

Met Lys His Ile Phe Asn Arg Ile Glu Tyr His Thr Lys Ile Ile Asn
            420                 425                 430

Asp Lys Thr Lys Ile Ile Gln Asp Lys Ile Lys Leu Asn Ile Trp Arg
        435                 440                 445

Thr Phe Gln Lys Asp Glu Leu Leu Lys Arg Ile Leu Asp Met Ser Asn
    450                 455                 460

```
Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
                485                 490                 495

Leu Ile Tyr Val Leu Gln Met Lys Phe Asn Asp Val Pro Ile Lys Met
            500                 505                 510

Glu Tyr Phe Gln Thr Tyr Lys Lys Asn Lys Pro Leu Thr Gln
        515                 520                 525

<210> SEQ ID NO 3
<211> LENGTH: 387
<212> TYPE: PRT
<213> ORGANISM: Plasmodium falciparum

<400> SEQUENCE: 3

Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Tyr Lys His
        35                  40                  45

Leu Ser Tyr Asn Ser Ile Tyr His Lys Ser Ser Thr Tyr Gly Lys Cys
    50                  55                  60

Ile Ala Val Asp Ala Phe Ile Lys Lys Ile Asn Glu Ala Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Asp Asp Ser
            100                 105                 110

Tyr Arg Tyr Asp Ile Ser Glu Glu Ile Asp Asp Lys Ser Glu Glu Thr
        115                 120                 125

Asp Asp Glu Thr Glu Glu Val Glu Asp Ser Ile Gln Asp Thr Asp Ser
130                 135                 140

Asn His Ala Pro Ser Asn Lys Lys Asn Asp Leu Met Asn Arg Ala
145                 150                 155                 160

Phe Lys Lys Met Met Asp Glu Tyr Asn Thr Lys Lys Lys Leu Ile
                165                 170                 175

Lys Cys Ile Lys Asn His Glu Asn Asp Phe Asn Lys Ile Cys Met Asp
            180                 185                 190

Met Lys Asn Tyr Gly Thr Asn Leu Phe Glu Gln Leu Ser Cys Tyr Asn
        195                 200                 205

Asn Asn Phe Cys Asn Thr Asn Gly Ile Arg Tyr His Tyr Asp Glu Tyr
210                 215                 220

Ile His Lys Leu Ile Leu Ser Val Lys Ser Lys Asn Leu Asn Lys Asp
225                 230                 235                 240

Leu Ser Asp Met Thr Asn Ile Leu Gln Gln Ser Glu Leu Leu Leu Thr
                245                 250                 255

Asn Leu Asn Lys Lys Met Gly Ser Tyr Ile Tyr Ile Asp Thr Ile Lys
            260                 265                 270

Phe Ile His Lys Glu Met Lys His Ile Phe Asn Arg Ile Glu Tyr His
        275                 280                 285

Thr Lys Ile Ile Asn Asp Lys Thr Lys Ile Ile Gln Asp Lys Ile Lys
        290                 295                 300

Leu Asn Ile Trp Arg Thr Phe Gln Lys Asp Glu Leu Leu Lys Arg Ile
305                 310                 315                 320
```

```
Leu Asp Met Ser Asn Glu Tyr Ser Leu Phe Ile Thr Ser Asp His Leu
            325                 330                 335

Arg Gln Met Leu Tyr Asn Thr Phe Tyr Ser Lys Glu Lys His Leu Asn
            340                 345                 350

Asn Ile Phe His His Leu Ile Tyr Val Leu Gln Met Lys Phe Asn Asp
            355                 360                 365

Val Pro Ile Lys Met Glu Tyr Phe Gln Thr Tyr Lys Lys Asn Lys Pro
            370                 375                 380

Leu Thr Gln
385

<210> SEQ ID NO 4
<211> LENGTH: 387
<212> TYPE: PRT
<213> ORGANISM: Plasmodium falciparum

<400> SEQUENCE: 4

Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Tyr Lys His
            35                  40                  45

Leu Ser Tyr Asn Ser Ile Tyr His Lys Ser Ser Thr Tyr Gly Lys Tyr
        50                  55                  60

Ile Ala Val Asp Ala Phe Ile Lys Lys Ile Asn Glu Ala Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Asp Asp Ser
            100                 105                 110

Tyr Arg Tyr Asp Ile Ser Glu Glu Ile Asp Asp Lys Ser Glu Glu Thr
            115                 120                 125

Asp Asp Glu Thr Glu Glu Val Glu Asp Ser Ile Gln Asp Thr Asp Ser
130                 135                 140

Asn His Ala Pro Ser Asn Lys Lys Asn Asp Leu Met Asn Arg Ala
145                 150                 155                 160

Phe Lys Lys Met Met Asp Glu Tyr Asn Thr Lys Lys Lys Lys Leu Ile
            165                 170                 175

Lys Cys Ile Lys Asn His Glu Asn Asp Phe Asn Lys Ile Cys Met Asp
            180                 185                 190

Met Lys Asn Tyr Gly Thr Asn Leu Phe Glu Gln Leu Ser Cys Tyr Asn
            195                 200                 205

Asn Asn Phe Cys Asn Thr Asn Gly Ile Arg Tyr His Tyr Asp Glu Tyr
        210                 215                 220

Ile His Lys Leu Ile Leu Ser Val Lys Ser Lys Asn Leu Asn Lys Asp
225                 230                 235                 240

Leu Ser Asp Met Thr Asn Ile Leu Gln Gln Ser Glu Leu Leu Leu Thr
                245                 250                 255

Asn Leu Asn Lys Lys Met Gly Ser Tyr Ile Tyr Ile Asp Thr Ile Lys
            260                 265                 270

Phe Ile His Lys Glu Met Lys His Ile Phe Asn Arg Ile Glu Tyr His
            275                 280                 285

Thr Lys Ile Ile Asn Asp Lys Thr Lys Ile Ile Gln Asp Lys Ile Lys
```

```
                    290                 295                 300
Leu Asn Ile Trp Arg Thr Phe Gln Lys Asp Glu Leu Leu Lys Arg Ile
305                 310                 315                 320

Leu Asp Met Ser Asn Glu Tyr Ser Leu Phe Ile Thr Ser Asp His Leu
                325                 330                 335

Arg Gln Met Leu Tyr Asn Thr Phe Tyr Ser Lys Glu Lys His Leu Asn
            340                 345                 350

Asn Ile Phe His His Leu Ile Tyr Val Leu Gln Met Lys Phe Asn Asp
        355                 360                 365

Val Pro Ile Lys Met Glu Tyr Phe Gln Thr Tyr Lys Lys Asn Lys Pro
370                 375                 380

Leu Thr Gln
385

<210> SEQ ID NO 5
<211> LENGTH: 367
<212> TYPE: PRT
<213> ORGANISM: Plasmodium falciparum

<400> SEQUENCE: 5

Ser Ile Asp Ile Leu Gln Glu Lys Glu Gly His Leu Asp Phe Val Ile
1               5                   10                  15

Ile Pro His Tyr Thr Phe Leu Asp Tyr Lys His Leu Ser Tyr Asn
            20                  25                  30

Ser Ile Tyr His Lys Ser Ser Thr Tyr Gly Lys Cys Ile Ala Val Asp
        35                  40                  45

Ala Phe Ile Lys Lys Ile Asn Glu Ala Tyr Asp Lys Val Lys Ser Lys
    50                  55                  60

Cys Asn Asp Ile Lys Asn Asp Leu Ile Ala Thr Ile Lys Lys Leu Glu
65                  70                  75                  80

His Pro Tyr Asp Ile Asn Asn Lys Asn Asp Asp Ser Tyr Arg Tyr Asp
                85                  90                  95

Ile Ser Glu Glu Ile Asp Asp Lys Ser Glu Glu Thr Asp Asp Glu Thr
            100                 105                 110

Glu Glu Val Glu Asp Ser Ile Gln Asp Thr Asp Ser Asn His Ala Pro
        115                 120                 125

Ser Asn Lys Lys Lys Asn Asp Leu Met Asn Arg Ala Phe Lys Lys Met
    130                 135                 140

Met Asp Glu Tyr Asn Thr Lys Lys Lys Leu Ile Lys Cys Ile Lys
145                 150                 155                 160

Asn His Glu Asn Asp Phe Asn Lys Ile Cys Met Asp Met Lys Asn Tyr
                165                 170                 175

Gly Thr Asn Leu Phe Glu Gln Leu Ser Cys Tyr Asn Asn Asn Phe Cys
            180                 185                 190

Asn Thr Asn Gly Ile Arg Tyr His Tyr Asp Glu Tyr Ile His Lys Leu
        195                 200                 205

Ile Leu Ser Val Lys Ser Lys Asn Leu Asn Lys Asp Leu Ser Asp Met
    210                 215                 220

Thr Asn Ile Leu Gln Gln Ser Glu Leu Leu Leu Thr Asn Leu Asn Lys
225                 230                 235                 240

Lys Met Gly Ser Tyr Ile Tyr Ile Asp Thr Ile Lys Phe Ile His Lys
                245                 250                 255

Glu Met Lys His Ile Phe Asn Arg Ile Glu Tyr His Thr Lys Ile Ile
            260                 265                 270
```

```
Asn Asp Lys Thr Lys Ile Ile Gln Asp Lys Ile Lys Leu Asn Ile Trp
            275                 280                 285

Arg Thr Phe Gln Lys Asp Glu Leu Leu Lys Arg Ile Leu Asp Met Ser
        290                 295                 300

Asn Glu Tyr Ser Leu Phe Ile Thr Ser Asp His Leu Arg Gln Met Leu
305                 310                 315                 320

Tyr Asn Thr Phe Tyr Ser Lys Glu Lys His Leu Asn Asn Ile Phe His
                325                 330                 335

His Leu Ile Tyr Val Leu Gln Met Lys Phe Asn Asp Val Pro Ile Lys
            340                 345                 350

Met Glu Tyr Phe Gln Thr Tyr Lys Lys Asn Lys Pro Leu Thr Gln
        355                 360                 365

<210> SEQ ID NO 6
<211> LENGTH: 367
<212> TYPE: PRT
<213> ORGANISM: Plasmodium falciparum

<400> SEQUENCE: 6

Ser Ile Asp Ile Leu Gln Glu Lys Glu Gly His Leu Asp Phe Val Ile
1               5                   10                  15

Ile Pro His Tyr Thr Phe Leu Asp Tyr Tyr Lys His Leu Ser Tyr Asn
            20                  25                  30

Ser Ile Tyr His Lys Ser Ser Thr Tyr Gly Lys Tyr Ile Ala Val Asp
        35                  40                  45

Ala Phe Ile Lys Lys Ile Asn Glu Ala Tyr Asp Lys Val Lys Ser Lys
    50                  55                  60

Cys Asn Asp Ile Lys Asn Asp Leu Ile Ala Thr Ile Lys Lys Leu Glu
65                  70                  75                  80

His Pro Tyr Asp Ile Asn Asn Lys Asn Asp Asp Ser Tyr Arg Tyr Asp
                85                  90                  95

Ile Ser Glu Glu Ile Asp Asp Lys Ser Glu Glu Thr Asp Asp Glu Thr
            100                 105                 110

Glu Glu Val Glu Asp Ser Ile Gln Asp Thr Asp Ser Asn His Ala Pro
        115                 120                 125

Ser Asn Lys Lys Lys Asn Asp Leu Met Asn Arg Ala Phe Lys Lys Met
    130                 135                 140

Met Asp Glu Tyr Asn Thr Lys Lys Lys Leu Ile Lys Cys Ile Lys
145                 150                 155                 160

Asn His Glu Asn Asp Phe Asn Lys Ile Cys Met Asp Met Lys Asn Tyr
                165                 170                 175

Gly Thr Asn Leu Phe Glu Gln Leu Ser Cys Tyr Asn Asn Phe Cys
            180                 185                 190

Asn Thr Asn Gly Ile Arg Tyr His Tyr Asp Glu Tyr Ile His Lys Leu
        195                 200                 205

Ile Leu Ser Val Lys Ser Lys Asn Leu Asn Lys Asp Leu Ser Asp Met
    210                 215                 220

Thr Asn Ile Leu Gln Gln Ser Glu Leu Leu Leu Thr Asn Leu Asn Lys
225                 230                 235                 240

Lys Met Gly Ser Tyr Ile Tyr Ile Asp Thr Ile Lys Phe Ile His Lys
                245                 250                 255

Glu Met Lys His Ile Phe Asn Arg Ile Glu Tyr His Thr Lys Ile Ile
            260                 265                 270

Asn Asp Lys Thr Lys Ile Ile Gln Asp Lys Ile Lys Leu Asn Ile Trp
        275                 280                 285
```

Arg Thr Phe Gln Lys Asp Glu Leu Leu Lys Arg Ile Leu Asp Met Ser
            290                 295                 300

Asn Glu Tyr Ser Leu Phe Ile Thr Ser Asp His Leu Arg Gln Met Leu
305                 310                 315                 320

Tyr Asn Thr Phe Tyr Ser Lys Glu Lys His Leu Asn Asn Ile Phe His
                325                 330                 335

His Leu Ile Tyr Val Leu Gln Met Lys Phe Asn Asp Val Pro Ile Lys
            340                 345                 350

Met Glu Tyr Phe Gln Thr Tyr Lys Lys Asn Lys Pro Leu Thr Gln
            355                 360                 365

<210> SEQ ID NO 7
<211> LENGTH: 338
<212> TYPE: PRT
<213> ORGANISM: Artificial Sequence
<220> FEATURE:
<223> OTHER INFORMATION: PfRH5 (3D7) sequence excluding flexible N-
      terminal (1-139) and flexible loop regions

<400> SEQUENCE: 7

Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Lys His
            35                  40                  45

Leu Ser Tyr Asn Ser Ile Tyr His Lys Ser Ser Thr Tyr Gly Lys Cys
50                  55                  60

Ile Ala Val Asp Ala Phe Ile Lys Lys Ile Asn Glu Ala Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Lys Asn Arg Ala Phe
            100                 105                 110

Lys Lys Met Met Asp Glu Tyr Asn Thr Lys Lys Lys Leu Ile Lys
            115                 120                 125

Cys Ile Lys Asn His Glu Asn Asp Phe Asn Lys Ile Cys Met Asp Met
130                 135                 140

Lys Asn Tyr Gly Thr Asn Leu Phe Glu Gln Leu Ser Cys Tyr Asn Asn
145                 150                 155                 160

Asn Phe Cys Asn Thr Asn Gly Ile Arg Tyr His Tyr Asp Glu Tyr Ile
                165                 170                 175

His Lys Leu Ile Leu Ser Val Lys Ser Lys Asn Leu Asn Lys Asp Leu
            180                 185                 190

Ser Asp Met Thr Asn Ile Leu Gln Gln Ser Glu Leu Leu Leu Thr Asn
            195                 200                 205

Leu Asn Lys Lys Met Gly Ser Tyr Ile Tyr Ile Asp Thr Ile Lys Phe
            210                 215                 220

Ile His Lys Glu Met Lys His Ile Phe Asn Arg Ile Glu Tyr His Thr
225                 230                 235                 240

Lys Ile Ile Asn Asp Lys Thr Lys Ile Gln Asp Lys Ile Lys Leu
                245                 250                 255

Asn Ile Trp Arg Thr Phe Gln Lys Asp Glu Leu Leu Lys Arg Ile Leu
            260                 265                 270

Asp Met Ser Asn Glu Tyr Ser Leu Phe Ile Thr Ser Asp His Leu Arg

```
                    275                 280                 285
Gln Met Leu Tyr Asn Thr Phe Tyr Ser Lys Glu Lys His Leu Asn Asn
            290                 295                 300
Ile Phe His His Leu Ile Tyr Val Leu Gln Met Lys Phe Asn Asp Val
305                 310                 315                 320
Pro Ile Lys Met Glu Tyr Phe Gln Thr Tyr Lys Lys Asn Lys Pro Leu
                325                 330                 335
Thr Gln

<210> SEQ ID NO 8
<211> LENGTH: 338
<212> TYPE: PRT
<213> ORGANISM: Artificial Sequence
<220> FEATURE:
<223> OTHER INFORMATION: PfRH5 (7G8) sequence excluding flexible N-
      terminal (1-139) and flexible loop regions

<400> SEQUENCE: 8

Lys Asn Val Asn Phe Leu Gln Tyr His Phe Lys Glu Leu Ser Asn Tyr
1               5                   10                  15
Asn Ile Ala Asn Ser Ile Asp Ile Leu Gln Glu Lys Glu Gly His Leu
            20                  25                  30
Asp Phe Val Ile Ile Pro His Tyr Thr Phe Leu Asp Tyr Tyr Lys His
        35                  40                  45
Leu Ser Tyr Asn Ser Ile Tyr His Lys Ser Ser Thr Tyr Gly Lys Tyr
    50                  55                  60
Ile Ala Val Asp Ala Phe Ile Lys Lys Ile Asn Glu Ala Tyr Asp Lys
65                  70                  75                  80
Val Lys Ser Lys Cys Asn Asp Ile Lys Asn Asp Leu Ile Ala Thr Ile
                85                  90                  95
Lys Lys Leu Glu His Pro Tyr Asp Ile Asn Asn Lys Asn Arg Ala Phe
            100                 105                 110
Lys Lys Met Met Asp Glu Tyr Asn Thr Lys Lys Lys Leu Ile Lys
            115                 120                 125
Cys Ile Lys Asn His Glu Asn Asp Phe Asn Lys Ile Cys Met Asp Met
130                 135                 140
Lys Asn Tyr Gly Thr Asn Leu Phe Glu Gln Leu Ser Cys Tyr Asn Asn
145                 150                 155                 160
Asn Phe Cys Asn Thr Asn Gly Ile Arg Tyr His Tyr Asp Glu Tyr Ile
                165                 170                 175
His Lys Leu Ile Leu Ser Val Lys Ser Lys Asn Leu Asn Lys Asp Leu
            180                 185                 190
Ser Asp Met Thr Asn Ile Leu Gln Gln Ser Glu Leu Leu Leu Thr Asn
        195                 200                 205
Leu Asn Lys Lys Met Gly Ser Tyr Ile Tyr Ile Asp Thr Ile Lys Phe
    210                 215                 220
Ile His Lys Glu Met Lys His Ile Phe Asn Arg Ile Glu Tyr His Thr
225                 230                 235                 240
Lys Ile Ile Asn Asp Lys Thr Lys Ile Ile Gln Asp Lys Ile Lys Leu
                245                 250                 255
Asn Ile Trp Arg Thr Phe Gln Lys Asp Glu Leu Leu Lys Arg Ile Leu
            260                 265                 270
Asp Met Ser Asn Glu Tyr Ser Leu Phe Ile Thr Ser Asp His Leu Arg
        275                 280                 285
Gln Met Leu Tyr Asn Thr Phe Tyr Ser Lys Glu Lys His Leu Asn Asn
```

```
                290                 295                 300
Ile Phe His His Leu Ile Tyr Val Leu Gln Met Lys Phe Asn Asp Val
305                 310                 315                 320

Pro Ile Lys Met Glu Tyr Phe Gln Thr Tyr Lys Lys Asn Lys Pro Leu
                325                 330                 335

Thr Gln

<210> SEQ ID NO 9
<211> LENGTH: 318
<212> TYPE: PRT
<213> ORGANISM: Artificial Sequence
<220> FEATURE:
<223> OTHER INFORMATION: PfRH5 (3D7) sequence excluding flexible N-
      terminal (1-159) and flexible loop regions

<400> SEQUENCE: 9

Ser Ile Asp Ile Leu Gln Glu Lys Glu Gly His Leu Asp Phe Val Ile
1               5                   10                  15

Ile Pro His Tyr Thr Phe Leu Asp Tyr Tyr Lys His Leu Ser Tyr Asn
                20                  25                  30

Ser Ile Tyr His Lys Ser Ser Thr Tyr Gly Lys Cys Ile Ala Val Asp
            35                  40                  45

Ala Phe Ile Lys Lys Ile Asn Glu Ala Tyr Asp Lys Val Lys Ser Lys
        50                  55                  60

Cys Asn Asp Ile Lys Asn Asp Leu Ile Ala Thr Ile Lys Lys Leu Glu
65                  70                  75                  80

His Pro Tyr Asp Ile Asn Asn Lys Asn Arg Ala Phe Lys Lys Met Met
                85                  90                  95

Asp Glu Tyr Asn Thr Lys Lys Lys Leu Ile Lys Cys Ile Lys Asn
                100                 105                 110

His Glu Asn Asp Phe Asn Lys Ile Cys Met Asp Met Lys Asn Tyr Gly
            115                 120                 125

Thr Asn Leu Phe Glu Gln Leu Ser Cys Tyr Asn Asn Phe Cys Asn
        130                 135                 140

Thr Asn Gly Ile Arg Tyr His Tyr Asp Glu Tyr Ile His Lys Leu Ile
145                 150                 155                 160

Leu Ser Val Lys Ser Lys Asn Leu Asn Lys Asp Leu Ser Asp Met Thr
                165                 170                 175

Asn Ile Leu Gln Gln Ser Glu Leu Leu Leu Thr Asn Leu Asn Lys Lys
            180                 185                 190

Met Gly Ser Tyr Ile Tyr Ile Asp Thr Ile Lys Phe Ile His Lys Glu
        195                 200                 205

Met Lys His Ile Phe Asn Arg Ile Glu Tyr His Thr Lys Ile Ile Asn
    210                 215                 220

Asp Lys Thr Lys Ile Ile Gln Asp Lys Ile Lys Leu Asn Ile Trp Arg
225                 230                 235                 240

Thr Phe Gln Lys Asp Glu Leu Leu Lys Arg Ile Leu Asp Met Ser Asn
                245                 250                 255

Glu Tyr Ser Leu Phe Ile Thr Ser Asp His Leu Arg Gln Met Leu Tyr
            260                 265                 270

Asn Thr Phe Tyr Ser Lys Glu Lys His Leu Asn Asn Ile Phe His His
        275                 280                 285

Leu Ile Tyr Val Leu Gln Met Lys Phe Asn Asp Val Pro Ile Lys Met
    290                 295                 300

Glu Tyr Phe Gln Thr Tyr Lys Lys Asn Lys Pro Leu Thr Gln
```

<210> SEQ ID NO 10
<211> LENGTH: 318
<212> TYPE: PRT
<213> ORGANISM: Artificial Sequence
<220> FEATURE:
<223> OTHER INFORMATION: PfRH5 (7G8) sequence excluding flexible N-
      terminal (1-159) and flexible loop regions

<400> SEQUENCE: 10

Ser Ile Asp Ile Leu Gln Glu Lys Glu Gly His Leu Asp Phe Val Ile
1               5                   10                  15

Ile Pro His Tyr Thr Phe Leu Asp Tyr Tyr Lys His Leu Ser Tyr Asn
            20                  25                  30

Ser Ile Tyr His Lys Ser Ser Thr Tyr Gly Lys Tyr Ile Ala Val Asp
        35                  40                  45

Ala Phe Ile Lys Lys Ile Asn Glu Ala Tyr Asp Lys Val Lys Ser Lys
50                  55                  60

Cys Asn Asp Ile Lys Asn Asp Leu Ile Ala Thr Ile Lys Lys Leu Glu
65                  70                  75                  80

His Pro Tyr Asp Ile Asn Asn Lys Asn Arg Ala Phe Lys Lys Met Met
                85                  90                  95

Asp Glu Tyr Asn Thr Lys Lys Lys Leu Ile Lys Cys Ile Lys Asn
            100                 105                 110

His Glu Asn Asp Phe Asn Lys Ile Cys Met Asp Met Lys Asn Tyr Gly
        115                 120                 125

Thr Asn Leu Phe Glu Gln Leu Ser Cys Tyr Asn Asn Phe Cys Asn
130                 135                 140

Thr Asn Gly Ile Arg Tyr His Tyr Asp Glu Tyr Ile His Lys Leu Ile
145                 150                 155                 160

Leu Ser Val Lys Ser Lys Asn Leu Asn Lys Asp Leu Ser Asp Met Thr
                165                 170                 175

Asn Ile Leu Gln Gln Ser Glu Leu Leu Leu Thr Asn Leu Asn Lys Lys
            180                 185                 190

Met Gly Ser Tyr Ile Tyr Ile Asp Thr Ile Lys Phe Ile His Lys Glu
        195                 200                 205

Met Lys His Ile Phe Asn Arg Ile Glu Tyr His Thr Lys Ile Ile Asn
210                 215                 220

Asp Lys Thr Lys Ile Ile Gln Asp Lys Ile Lys Leu Asn Ile Trp Arg
225                 230                 235                 240

Thr Phe Gln Lys Asp Glu Leu Leu Lys Arg Ile Leu Asp Met Ser Asn
                245                 250                 255

Glu Tyr Ser Leu Phe Ile Thr Ser Asp His Leu Arg Gln Met Leu Tyr
            260                 265                 270

Asn Thr Phe Tyr Ser Lys Glu Lys His Leu Asn Asn Ile Phe His His
        275                 280                 285

Leu Ile Tyr Val Leu Gln Met Lys Phe Asn Asp Val Pro Ile Lys Met
        290                 295                 300

Glu Tyr Phe Gln Thr Tyr Lys Lys Asn Lys Pro Leu Thr Gln
305                 310                 315

<210> SEQ ID NO 11
<211> LENGTH: 411
<212> TYPE: PRT
<213> ORGANISM: Artificial Sequence
<220> FEATURE:

<223> OTHER INFORMATION: Sv2 (3D7) sequence excluding flexible N-terminal (1-139) region, with Bip leader and Hexa-His tag

<400> SEQUENCE: 11

```
Met Lys Leu Cys Ile Leu Leu Ala Val Val Ala Phe Val Gly Leu Ser
1               5                   10                  15

Leu Gly Lys Asn Val Asn Phe Leu Gln Tyr His Phe Lys Glu Leu Ser
            20                  25                  30

Asn Tyr Asn Ile Ala Asn Ser Ile Asp Ile Leu Gln Glu Lys Glu Gly
        35                  40                  45

His Leu Asp Phe Val Ile Ile Pro His Tyr Thr Phe Leu Asp Tyr Tyr
    50                  55                  60

Lys His Leu Ser Tyr Asn Ser Ile Tyr His Lys Ser Ser Thr Tyr Gly
65                  70                  75                  80

Lys Cys Ile Ala Val Asp Ala Phe Ile Lys Ile Asn Glu Ala Tyr
                85                  90                  95

Asp Lys Val Lys Ser Lys Cys Asn Asp Ile Lys Asn Asp Leu Ile Ala
            100                 105                 110

Thr Ile Lys Lys Leu Glu His Pro Tyr Asp Ile Asn Asn Lys Asn Asp
            115                 120                 125

Asp Ser Tyr Arg Tyr Asp Ile Ser Glu Glu Ile Asp Asp Lys Ser Glu
        130                 135                 140

Glu Thr Asp Asp Glu Thr Glu Val Glu Asp Ser Ile Gln Asp Thr
145                 150                 155                 160

Asp Ser Asn His Ala Pro Ser Asn Lys Lys Lys Asn Asp Leu Met Asn
                165                 170                 175

Arg Ala Phe Lys Lys Met Met Asp Glu Tyr Asn Thr Lys Lys Lys Lys
                180                 185                 190

Leu Ile Lys Cys Ile Lys Asn His Glu Asn Asp Phe Asn Lys Ile Cys
            195                 200                 205

Met Asp Met Lys Asn Tyr Gly Thr Asn Leu Phe Glu Gln Leu Ser Cys
        210                 215                 220

Tyr Asn Asn Asn Phe Cys Asn Thr Asn Gly Ile Arg Tyr His Tyr Asp
225                 230                 235                 240

Glu Tyr Ile His Lys Leu Ile Leu Ser Val Lys Ser Lys Asn Leu Asn
                245                 250                 255

Lys Asp Leu Ser Asp Met Thr Asn Ile Leu Gln Gln Ser Glu Leu Leu
            260                 265                 270

Leu Thr Asn Leu Asn Lys Lys Met Gly Ser Tyr Ile Tyr Ile Asp Thr
        275                 280                 285

Ile Lys Phe Ile His Lys Glu Met Lys His Ile Phe Asn Arg Ile Glu
290                 295                 300

Tyr His Thr Lys Ile Ile Asn Asp Lys Thr Lys Ile Ile Gln Asp Lys
305                 310                 315                 320

Ile Lys Leu Asn Ile Trp Arg Thr Phe Gln Lys Asp Glu Leu Leu Lys
                325                 330                 335

Arg Ile Leu Asp Met Ser Asn Glu Tyr Ser Leu Phe Ile Thr Ser Asp
            340                 345                 350

His Leu Arg Gln Met Leu Tyr Asn Thr Phe Tyr Ser Lys Glu Lys His
        355                 360                 365

Leu Asn Asn Ile Phe His His Leu Ile Tyr Val Leu Gln Met Lys Phe
    370                 375                 380

Asn Asp Val Pro Ile Lys Met Glu Tyr Phe Gln Thr Tyr Lys Lys Asn
385                 390                 395                 400
```

```
Lys Pro Leu Thr Gln His His His His His
                405                 410

<210> SEQ ID NO 12
<211> LENGTH: 411
<212> TYPE: PRT
<213> ORGANISM: Artificial Sequence
<220> FEATURE:
<223> OTHER INFORMATION: Sv2 (7G8) sequence excluding flexible N-
      terminal (1-139) region, with Bip leader and Hexa-His tag

<400> SEQUENCE: 12

Met Lys Leu Cys Ile Leu Leu Ala Val Ala Phe Val Gly Leu Ser
1               5                   10                  15

Leu Gly Lys Asn Val Asn Phe Leu Gln Tyr His Phe Lys Glu Leu Ser
            20                  25                  30

Asn Tyr Asn Ile Ala Asn Ser Ile Asp Ile Leu Gln Glu Lys Glu Gly
        35                  40                  45

His Leu Asp Phe Val Ile Ile Pro His Tyr Thr Phe Leu Asp Tyr Tyr
    50                  55                  60

Lys His Leu Ser Tyr Asn Ser Ile Tyr His Lys Ser Ser Thr Tyr Gly
65                  70                  75                  80

Lys Tyr Ile Ala Val Asp Ala Phe Ile Lys Lys Ile Asn Glu Ala Tyr
                85                  90                  95

Asp Lys Val Lys Ser Lys Cys Asn Asp Ile Lys Asn Asp Leu Ile Ala
            100                 105                 110

Thr Ile Lys Lys Leu Glu His Pro Tyr Asp Ile Asn Asn Lys Asn Asp
        115                 120                 125

Asp Ser Tyr Arg Tyr Asp Ile Ser Glu Glu Ile Asp Asp Lys Ser Glu
    130                 135                 140

Glu Thr Asp Asp Glu Thr Glu Glu Val Glu Asp Ser Ile Gln Asp Thr
145                 150                 155                 160

Asp Ser Asn His Ala Pro Ser Asn Lys Lys Asn Asp Leu Met Asn
                165                 170                 175

Arg Ala Phe Lys Lys Met Met Asp Glu Tyr Asn Thr Lys Lys Lys Lys
                180                 185                 190

Leu Ile Lys Cys Ile Lys Asn His Glu Asn Asp Phe Asn Lys Ile Cys
            195                 200                 205

Met Asp Met Lys Asn Tyr Gly Thr Asn Leu Phe Glu Gln Leu Ser Cys
    210                 215                 220

Tyr Asn Asn Asn Phe Cys Asn Thr Asn Gly Ile Arg Tyr His Tyr Asp
225                 230                 235                 240

Glu Tyr Ile His Lys Leu Ile Leu Ser Val Lys Ser Lys Asn Leu Asn
                245                 250                 255

Lys Asp Leu Ser Asp Met Thr Asn Ile Leu Gln Gln Ser Glu Leu Leu
            260                 265                 270

Leu Thr Asn Leu Asn Lys Lys Met Gly Ser Tyr Ile Tyr Ile Asp Thr
        275                 280                 285

Ile Lys Phe Ile His Lys Glu Met Lys His Ile Phe Asn Arg Ile Glu
    290                 295                 300

Tyr His Thr Lys Ile Ile Asn Asp Lys Thr Lys Ile Ile Gln Asp Lys
305                 310                 315                 320

Ile Lys Leu Asn Ile Trp Arg Thr Phe Gln Lys Asp Glu Leu Leu Lys
                325                 330                 335

Arg Ile Leu Asp Met Ser Asn Glu Tyr Ser Leu Phe Ile Thr Ser Asp
```

340                 345                 350
His Leu Arg Gln Met Leu Tyr Asn Thr Phe Tyr Ser Lys Glu Lys His
            355                 360                 365

Leu Asn Asn Ile Phe His His Leu Ile Tyr Val Leu Gln Met Lys Phe
        370                 375                 380

Asn Asp Val Pro Ile Lys Met Glu Tyr Phe Gln Thr Tyr Lys Lys Asn
385                 390                 395                 400

Lys Pro Leu Thr Gln His His His His His His
                405                 410

<210> SEQ ID NO 13
<211> LENGTH: 362
<212> TYPE: PRT
<213> ORGANISM: Artificial Sequence
<220> FEATURE:
<223> OTHER INFORMATION: Sv3 (3D7) sequence excluding flexible N-
      terminal (1-139) and flexible loop regions, with Bip leader and
      Hexa-His tag

<400> SEQUENCE: 13

Met Lys Leu Cys Ile Leu Leu Ala Val Val Ala Phe Val Gly Leu Ser
1               5                   10                  15

Leu Gly Lys Asn Val Asn Phe Leu Gln Tyr His Phe Lys Glu Leu Ser
            20                  25                  30

Asn Tyr Asn Ile Ala Asn Ser Ile Asp Ile Leu Gln Glu Lys Glu Gly
        35                  40                  45

His Leu Asp Phe Val Ile Ile Pro His Tyr Thr Phe Leu Asp Tyr Tyr
    50                  55                  60

Lys His Leu Ser Tyr Asn Ser Ile Tyr His Lys Ser Ser Thr Tyr Gly
65                  70                  75                  80

Lys Cys Ile Ala Val Asp Ala Phe Ile Lys Lys Ile Asn Glu Ala Tyr
                85                  90                  95

Asp Lys Val Lys Ser Lys Cys Asn Asp Ile Lys Asn Asp Leu Ile Ala
            100                 105                 110

Thr Ile Lys Lys Leu Glu His Pro Tyr Asp Ile Asn Asn Lys Asn Arg
        115                 120                 125

Ala Phe Lys Lys Met Met Asp Glu Tyr Asn Thr Lys Lys Lys Lys Leu
    130                 135                 140

Ile Lys Cys Ile Lys Asn His Glu Asn Asp Phe Asn Lys Ile Cys Met
145                 150                 155                 160

Asp Met Lys Asn Tyr Gly Thr Asn Leu Phe Glu Gln Leu Ser Cys Tyr
                165                 170                 175

Asn Asn Asn Phe Cys Asn Thr Asn Gly Ile Arg Tyr His Tyr Asp Glu
            180                 185                 190

Tyr Ile His Lys Leu Ile Leu Ser Val Lys Ser Lys Asn Leu Asn Lys
        195                 200                 205

Asp Leu Ser Asp Met Thr Asn Ile Leu Gln Gln Ser Glu Leu Leu
    210                 215                 220

Thr Asn Leu Asn Lys Lys Met Gly Ser Tyr Ile Tyr Ile Asp Thr Ile
225                 230                 235                 240

Lys Phe Ile His Lys Glu Met Lys His Ile Phe Asn Arg Ile Glu Tyr
                245                 250                 255

His Thr Lys Ile Ile Asn Asp Lys Thr Lys Ile Ile Gln Asp Lys Ile
            260                 265                 270

Lys Leu Asn Ile Trp Arg Thr Phe Gln Lys Asp Glu Leu Leu Lys Arg
        275                 280                 285

Ile Leu Asp Met Ser Asn Glu Tyr Ser Leu Phe Ile Thr Ser Asp His
    290                 295                 300

Leu Arg Gln Met Leu Tyr Asn Thr Phe Tyr Ser Lys Glu Lys His Leu
305                 310                 315                 320

Asn Asn Ile Phe His His Leu Ile Tyr Val Leu Gln Met Lys Phe Asn
                325                 330                 335

Asp Val Pro Ile Lys Met Glu Tyr Phe Gln Thr Tyr Lys Lys Asn Lys
            340                 345                 350

Pro Leu Thr Gln His His His His His His
        355                 360

<210> SEQ ID NO 14
<211> LENGTH: 362
<212> TYPE: PRT
<213> ORGANISM: Artificial Sequence
<220> FEATURE:
<223> OTHER INFORMATION: Sv3 (7G8) sequence excluding flexible N-
      terminal (1-139) and flexible loop regions, with Bip leader and
      Hexa-His tag

<400> SEQUENCE: 14

Met Lys Leu Cys Ile Leu Leu Ala Val Val Ala Phe Val Gly Leu Ser
1               5                   10                  15

Leu Gly Lys Asn Val Asn Phe Leu Gln Tyr His Phe Lys Glu Leu Ser
            20                  25                  30

Asn Tyr Asn Ile Ala Asn Ser Ile Asp Ile Leu Gln Glu Lys Glu Gly
        35                  40                  45

His Leu Asp Phe Val Ile Ile Pro His Tyr Thr Phe Leu Asp Tyr Tyr
    50                  55                  60

Lys His Leu Ser Tyr Asn Ser Ile Tyr His Lys Ser Ser Thr Tyr Gly
65                  70                  75                  80

Lys Tyr Ile Ala Val Asp Ala Phe Ile Lys Lys Ile Asn Glu Ala Tyr
                85                  90                  95

Asp Lys Val Lys Ser Lys Cys Asn Asp Ile Lys Asn Asp Leu Ile Ala
            100                 105                 110

Thr Ile Lys Lys Leu Glu His Pro Tyr Asp Ile Asn Asn Lys Asn Arg
        115                 120                 125

Ala Phe Lys Lys Met Met Asp Glu Tyr Asn Thr Lys Lys Lys Lys Leu
    130                 135                 140

Ile Lys Cys Ile Lys Asn His Glu Asn Asp Phe Asn Lys Ile Cys Met
145                 150                 155                 160

Asp Met Lys Asn Tyr Gly Thr Asn Leu Phe Glu Gln Leu Ser Cys Tyr
                165                 170                 175

Asn Asn Asn Phe Cys Asn Thr Asn Gly Ile Arg Tyr His Tyr Asp Glu
            180                 185                 190

Tyr Ile His Lys Leu Ile Leu Ser Val Lys Ser Lys Asn Leu Asn Lys
        195                 200                 205

Asp Leu Ser Asp Met Thr Asn Ile Leu Gln Gln Ser Glu Leu Leu Leu
    210                 215                 220

Thr Asn Leu Asn Lys Lys Met Gly Ser Tyr Ile Tyr Ile Asp Thr Ile
225                 230                 235                 240

Lys Phe Ile His Lys Glu Met Lys His Ile Phe Asn Arg Ile Glu Tyr
                245                 250                 255

His Thr Lys Ile Ile Asn Asp Lys Thr Lys Ile Ile Gln Asp Lys Ile
            260                 265                 270

```
Lys Leu Asn Ile Trp Arg Thr Phe Gln Lys Asp Glu Leu Leu Lys Arg
        275                 280                 285

Ile Leu Asp Met Ser Asn Glu Tyr Ser Leu Phe Ile Thr Ser Asp His
        290                 295                 300

Leu Arg Gln Met Leu Tyr Asn Thr Phe Tyr Ser Lys Glu Lys His Leu
305                 310                 315                 320

Asn Asn Ile Phe His His Leu Ile Tyr Val Leu Gln Met Lys Phe Asn
                325                 330                 335

Asp Val Pro Ile Lys Met Glu Tyr Phe Gln Thr Tyr Lys Lys Asn Lys
            340                 345                 350

Pro Leu Thr Gln His His His His His His
        355                 360
```

TREATMENT AND PREVENTION OF MALARIA

FIELD OF THE INVENTION

The present invention relates to antigens, antibodies and vaccines for treatment or prevention of malaria.

BACKGROUND OF THE INVENTION

The infection of red blood cells (RBCs) by the blood-stage form of the Plasmodium parasite is responsible for the clinical manifestations of malaria. Examples of Plasmodium parasite include the species P. falciparum, P. vivax, P. ovale and P. malariae. The parasite of particular interest is P. falciparum, as it is this parasite which causes the most lethal infections since it can infect RBCs of all ages and is not limited to immature RBCs. P. falciparum alone is responsible for around a million deaths per year, mainly in children.

It would therefore be highly desirable to develop a vaccine.

The most advanced current vaccine candidates are based on the RTS,S protein, which acts by blocking infection of P. falciparum in the liver, have achieved only partial efficacy. There is therefore a need for a vaccine which can emulate natural immunity by protecting against the disease-causing blood-stage Plasmodium parasite.

Previous studies have investigated the potential for antigens to induce antibodies which are effective against blood-stage malaria parasites in vitro, using the standard growth inhibitory activity (GIA) assay. One such antigen is apical membrane antigen 1 (PfAMA1).

GIA assay investigations into other protein families involved in blood-stage Plasmodium parasite invasion of RBCs have found them to be ineffective or less effective than PfAMA1.

PfAMA1 has therefore been a major focus of research on countering blood-stage malarial parasites, with ongoing clinical trials. However, antibodies against PfAMA1 appear only to be effective at an extremely high concentration. In addition, PfAMA1 induces strain-specific antibodies which are not effective against genetically diverse strains of the Plasmodium parasite (A. L. Goodman, S. J. Draper, Ann. Trop. Med. Parasitol. 104, 189 (2010)). In addition, vaccine development has been hampered by the requirement for potentially reactogenic chemical adjuvants in addition to the antigen to induce sufficient antibody responses in human subjects.

Research has also been ongoing to identify other candidate malarial antigens for vaccines. In particular, the present inventors have previously identified Reticulocyte-binding protein Homologue 5 (PfRH5) as a potential antigen candidate for malarial vaccines (WO 2012/114125).

The Reticulocyte binding Homologue (PfRH) family comprises six members (PfRH1, PfRH2a, PfRH2b, PfRH3, PfRH4 and PfRH5), each of which is involved in the binding of the Plasmodium parasite to RBCs, with the possible exception of PfRH3 which may be a non-expressed pseudogene. The PfRH family has been identified as adhesins on the surface of the merozoite form of the Plasmodium parasite, which bind to receptors on the surface of the erythrocyte and hence permit invasion of RBCs by the parasite in its blood-stage. The PfRH5 antigen has an approximate molecular weight of 63 KDa. In vitro cleaved fragments of approximately 45 KDa and 28 KDa have been reported.

The present inventors have previously demonstrated that PfRH5 induces antibodies which are highly effective in the GIA assay against the blood-stage Plasmodium parasite and which neutralise parasites more effectively than PfAMA1 and remain effective at lower concentrations of immunoglobulin. In addition, PfRH5 induces antibodies which are effective against genetically diverse strains of the Plasmodium parasite. Therefore, PfRH5 is a promising candidate antigen for a malarial vaccine.

However, although PfRH5 is in itself a preferred candidate vaccine antigen than other antigens such as RTS,S (proprietary vaccine formulation by GlaxoSmithKline and the recognized malarial antigen is a fragment of Plasmodium falciparum circumsporozoite protein (PfCSP)) and PfAMA1, the use of a full-length protein antigen such as full length PfRH5, or empirically selected fragments thereof, may be further improved upon. In particular, only certain regions or amino acid residues within PfRH5 are likely to give rise to protective antibodies. Administering full length PfRH5, or empirically selected fragments thereof, as a vaccine to an individual will necessarily involve the administration of polypeptide chains that do not give rise to protective antibodies, and may even be associated with unwanted side effects.

Therefore, there is an ongoing need for the development of rationally designed antigens with improved properties. In particular, there is a need for improved antigens that will induce antibodies that are effective even at lower concentrations of immunoglobulin, for improved antigens that will induce antibodies that are effective against genetically diverse strains of the Plasmodium parasite, and for improved antigens that are effective without requiring potentially reactogenic chemical adjuvants. Further, there is a need to provide antigens that can be produced more inexpensively.

The present invention addresses one or more of the above needs by providing antigens, vectors encoding the antigens, and antibodies (and antibody-like molecules including aptamers and peptides) raised against the antigen, together with the use thereof (either alone or in combination) in the prevention or treatment of malaria. Antibodies and antibody-like molecules raised against the antigen may bind (e.g. specifically bind) to the antigen.

SUMMARY OF THE INVENTION

The crystal structure of PfRH5 binding to basigin, its receptor on red blood cells, has been solved for the first time by the present inventors. The present inventors have identified the key amino acid residues in PfRH5 which contact basigin. The inventors have also solved for the first time the crystal structure of PfRH5 binding to a number of antibodies known to inhibit the invasion of red blood cells by Plasmodium parasites. Using this information, the present inventors have been able to design and develop PfRH5 fragments as improved malarial vaccine candidates.

In particular, the present inventors have developed antigenic fragments of PfRH5 which lack the flexible N-terminal region of the full length PfRH5 protein, which surprisingly generate a more efficient antibody response that full length PfRH5. The present inventors have further developed discontinuous fragments of PfRH5, which lack the flexible loop region of full length PfRH5 as well as lacking the flexible N-terminal region. These discontinuous fragments provide a further improvement in the efficiency of the generated antibody response.

Accordingly, the present invention provides a vaccine composition comprising a Reticulocyte-binding protein Homologue 5 (PfRH5) antigen, wherein said antigen is a basigin-binding fragment of PfRH5 which lacks the flexible N-terminal region of PfRH5.

The flexible N-terminal region of PfRH5 may comprise amino acid residues corresponding to amino acid residues 1 to 139 of SEQ ID NO: 1 or 2. In a preferred embodiment, the flexible N-terminal region of PfRH5 corresponds to amino acid residues 1 to 159 of SEQ ID NO: 1 or 2.

Said fragment of PfRH5 may be a fragment of amino acid residues 140 to 526 of SEQ ID NO: 1 or 2, or a fragment of an amino acid sequence having at least 90% sequence identity to amino acid residues 140 to 526 of SEQ ID NO: 1 or 2. In a preferred embodiment, said fragment of PfRH5 may be a fragment of amino acid residues 160 to 526 of SEQ ID NO: 1 or 2, or a fragment of an amino acid sequence having at least 90% sequence identity to amino acid residues 160 to 526 of SEQ ID NO: 1 or 2.

Said fragment of PfRH5 may include a region of at least ten continuous amino acids that overlaps with amino acid residue 191 and/or amino acid residue 359 of SEQ ID NO: 1 or 2. In a preferred embodiment, said fragment of PfRH5 comprises at least amino acid residues: (i) 197 to 200, 350 to 362 and 447 to 449 of SEQ ID NO: 1 or 2; (ii) 196, 197, 346 to 354 and 452 of SEQ ID NO: 1 or 2; (iii) 205 to 212 and 331 to 342 of SEQ ID NO: 1 or 2; or (iv) any combination thereof. Optionally said fragment of PfRH5 is less than or equal to 360 amino acids in length.

Said fragment of PfRH5 may have an amino acid other than T at residue 216 and/or residue 286 and/or residue 299 of SEQ ID NO: 1 or 2. Preferably said fragment of PfRH5 has the amino acid A at residue 216 and/or residue 286 and/or residue 299 of SEQ ID NO: 1 or 2. More preferably said fragment of PfRH5 has the amino acid A at residues 216, 286 and 299 of SEQ ID NO: 1 or 2.

The composition may induce antibodies that have a growth inhibitory activity (GIA) of at least 50% at a concentration of 10 mg/ml.

Said Reticulocyte-binding protein Homologue 5 (PfRH5) antigen may be a discontinuous fragment of PfRH5. Said discontinuous fragment of PfRH5 may further lack the flexible loop region corresponding to amino acid residues 248 to 296 of SEQ ID NO: 1 or 2. Preferably said discontinuous fragment of PfRH5 has at least 90% sequence identity to any one of SEQ ID NO: 7 to 10.

Said fragment of PfRH5 may have at least 90% sequence identity to amino acid residues 140 to 526 of SEQ ID NO: 1 or 2. In one embodiment, said fragment of PfRH5 has the amino acid sequence of SEQ ID NO: 3 or 4. Said fragment of PfRH5 may have at least 90% sequence identity to amino acid residues 160 to 526 of SEQ ID NO: 1 or 2. In one embodiment, said fragment of PfRH5 has the amino acid sequence of SEQ ID NO: 5 or 6.

The composition of the invention may have at least 90% sequence identity to SEQ ID NO: 11, 12, 13 or 14.

The present invention further provides a composition as defined above, wherein the composition further comprises one or more antigens selected from PfAMA1, PfEBA175, PfRH1, PfRH2a, PfRH2b, PfRH4 and/or PfAARP (P. falciparum apical asparagine-rich protein), or a fragment thereof.

The composition of the invention may comprise said fragment of PfRH5 in the form of a recombinant protein, a protein particle, a virus-like particle, a fusion protein, or a combination thereof.

In one embodiment, the composition of the invention comprises a fusion of the fragment of PfRH5 and one or more antigens selected from PfAMA1, PfEBA175, PfRH1, PfRH2a, PfRH2b, PfRH4 and/or PfAARP, or a fragment thereof.

The invention further provides a viral vector, RNA vaccine or DNA plasmid that expresses a PfRH5 antigen of the invention. In one embodiment, the viral vector, RNA vaccine or DNA plasmid expresses a fragment of PfRH5, further comprising a signal peptide. The signal peptide may direct secretion from human cells and is optionally a mammalian signal peptide from tissue plasminogen activator.

The viral vector, RNA vaccine or DNA plasmid of the invention may further express one or more antigens selected from PfAMA1, PfEBA175, PfRH1, PfRH2a, PfRH2b, PfRH4 and/or PfAARP, or a fragment thereof. The fragment of PfRH5 antigen and one or more antigens selected from PfAMA1, PfEBA175, PfRH1, PfRH2a, PfRH2b, PfRH4 and/or PfAARP, or a fragment thereof, may be expressed as a fusion protein.

The present invention also provides a viral vector, RNA vaccine or DNA plasmid as defined herein in combination with a viral vector, RNA vaccine or DNA plasmid that expresses one or more antigens selected from PfAMA1, PfEBA175, PfRH1, PfRH2a, PfRH2b, PfRH4 and/or PfAARP, or a fragment thereof.

The viral vector of the invention may be a human or simian adenovirus, or a pox virus, preferably an AdHu5, ChAd63, ChAdOX1, ChAdOX2 or modified vaccinia Ankara (MVA) vector.

The RNA vaccine or DNA plasmid of the invention may be capable of expression in an immunised mammalian cell. Further, the DNA plasmid of the invention may be capable of expression in a heterologous protein expression system.

The invention further provides an antibody, or binding fragment thereof, that specifically binds to a PfRH5 antigen of the invention. Said antibody may be a monoclonal or polyclonal antibody. Said antibody may be an Fab, F(ab')2, Fv, scFv, Fd or dAb.

The invention further provides an oligonucleotide aptamer that specifically binds to a PfRH5 antigen of the invention.

The invention also provides a vaccine composition comprising the viral vector, and/or virus-like particle, and/or protein, and/or RNA vaccine and/or DNA plasmid of the invention.

The present invention also provides a vaccine composition, and/or virus-like particle, and/or protein, and/or viral vector and/or RNA vaccine and/or DNA vaccine and/or antibody and/or aptamer of the invention for use in the treatment and/or prevention of malaria.

The present invention further provides the use of a vaccine composition, and/or virus-like particle, and/or protein, and/or viral vector and/or RNA vaccine and/or DNA vaccine and/or antibody and/or aptamer of the invention in the manufacture of a medicament for the prevention and/or treatment of malaria.

The present invention also provides vaccine composition of the invention for use in the treatment and/or prevention of malaria, wherein the treatment and/or prevention comprises priming a subject with a human or simian adenovirus, for example AdHu5, ChAd63, ChAdOX1 or ChAdOX2. The treatment and/or prevention may further comprise boosting a subject with a pox virus, for example MVA.

The present invention further provides a vaccine composition for use in immunising a subject, wherein the PfRH5 antigen results in antibodies with a growth inhibitory activity (GIA) of at least 50% against the blood-stage *Plasmodium* parasite. In one embodiment, the PfRH5 antigen results in antibodies with a growth inhibitory activity (GIA) of at least 50% against a plurality of genetic strains of the blood-stage *Plasmodium* parasite.

In one embodiment the *Plasmodium* parasite is *Plasmodium falciparum*.

DETAILED DESCRIPTION OF THE INVENTION

PfRH5 Fragments

Invasion of host red blood cells is an essential stage in the life cycle of the *Plasmodium* parasites and in development of the pathology of malaria. Central to invasion by all species are host-parasite interactions mediated by two parasite protein families, the reticulocyte-binding homologue (RH) proteins and the erythrocyte-binding like (EBL) proteins. In *Plasmodium falciparum*, just one member of these families, PfRH5, has been shown to be necessary for red blood cell invasion, through its interaction with the red blood cell surface protein basigin. The present inventors have previously shown that antibodies targeting PfRH5 can block parasite invasion in vitro.

Figure 1:
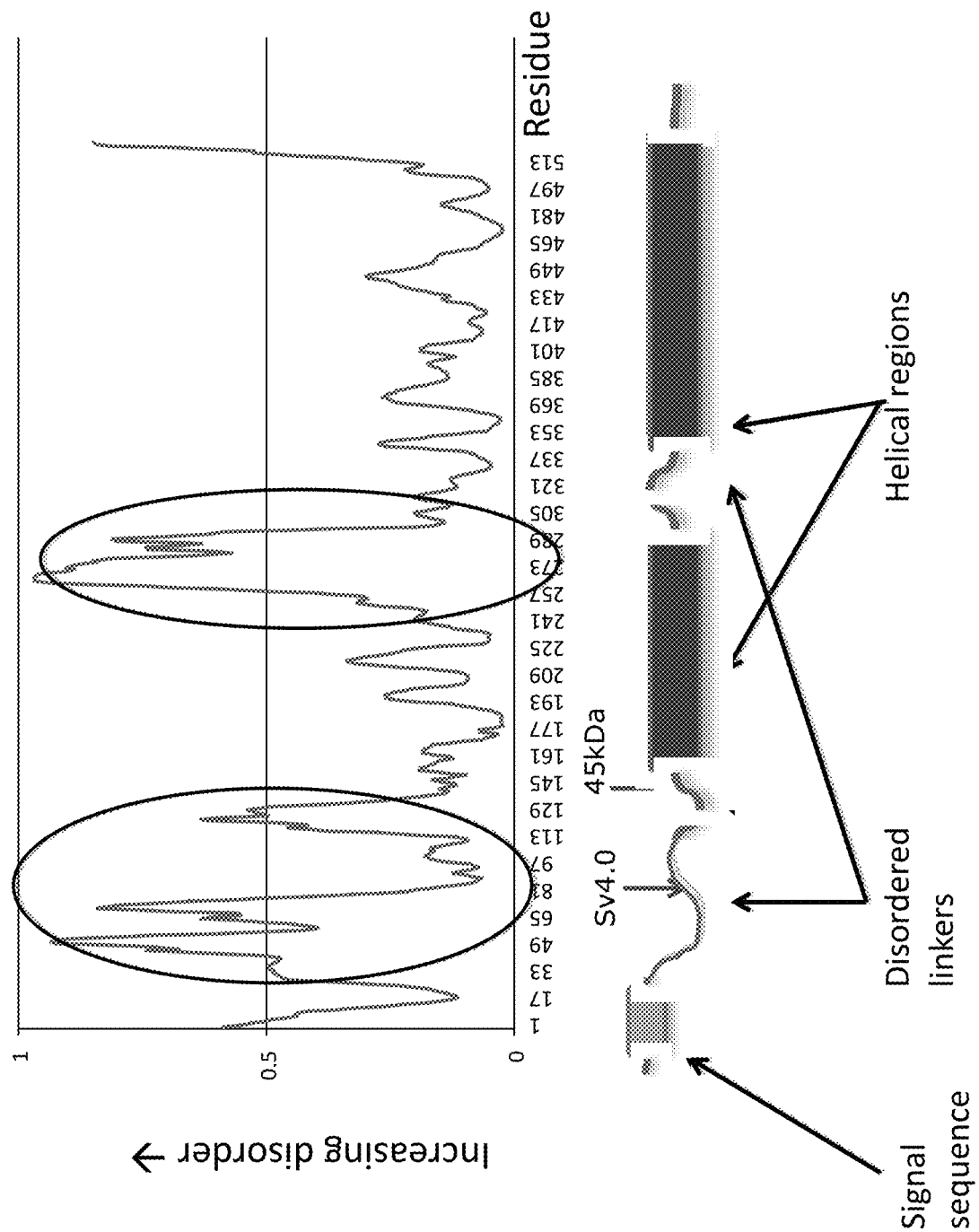
FIG. 1: Graph showing the disorder across the full length PfRH5 protein, together with a schematic of full length PfRH5 indicating the ordered and disordered regions.
Figure 2:
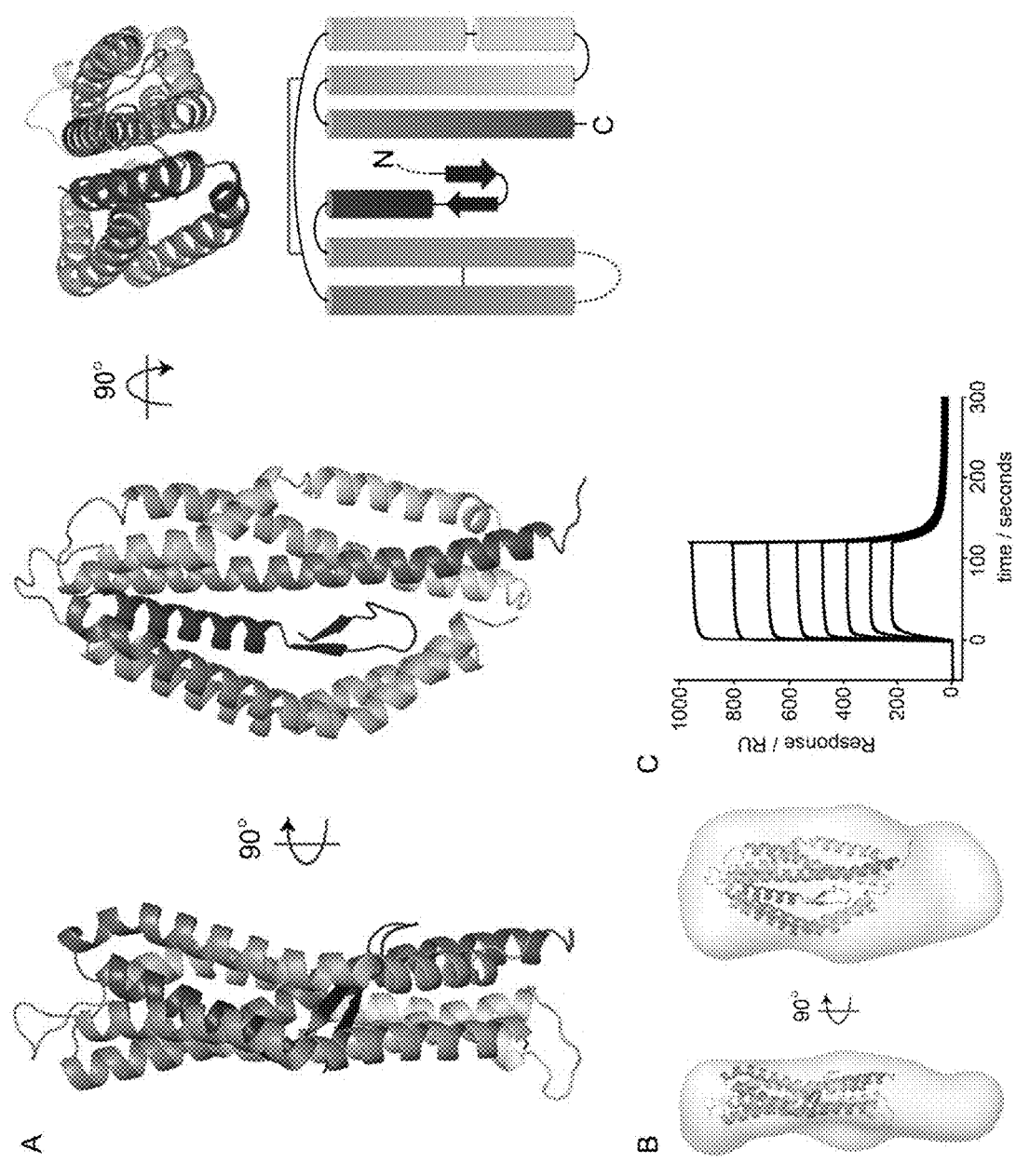
FIG. 2: The structure of RH5. (A) Three views of the structure of RH5ΔNL, and a schematic topology diagram, coloured from the N-terminus to the C-terminus. (B) RH5ΔNL, docked into a molecular envelope derived from small angle X-ray scattering. (C) Surface plasmon resonance (SPR) analysis of the RH5ΔNL:basigin interaction in which a concentration series of RH5ΔNL (8, 4, 2, I, 0.5, 0.25, 0.125, and 0.0625 μM) was injected over immobilized basigin. The data were fit to a 1:1 binding model, with a $K_d$ of 1.3 μM.

The present inventors have solved the crystal structure of PfRH5, specifically PfRH5 binding to basigin (FIG. 2). This is the first structure made available for any RH protein. Full length PfRH5 comprises disordered regions, where there is little secondary structure. In particular, full length PfRH5 comprises a flexible, disordered N-terminal region and a flexible, disordered central linker (see FIG. 1).

The present inventors have solved the crystal structure of a fragment of the PfRH5 protein lacking the flexible N-terminal region with basigin. The present inventors have identified a novel fold in which two three-helical bundles come together to form a kite-like architecture, and show that the structural basis for RH5 binding to basigin is the tip of RH5, which binds to each of the two immunoglobulin domains of basigin.

According to the present invention, the flexible N-terminal region of PfRH5 comprises amino acid residues corresponding to amino acid residues 1 to 139 of SEQ ID NO: 1 or 2. For example, in a preferred embodiment the flexible N-terminal region of PfRH5 corresponds to amino acid residues 1 to 159 of SEQ ID NO: 1 or 2. Amino acid residues corresponding to amino acid residues 1 to 23 of SEQ ID NO:

1 or 2 are typically a signal peptide that is cleaved from the mature PfRH5 protein. As used herein, the term flexible N-terminal region may include or exclude the signal peptide. Thus, the term flexible N-terminal region may include the signal peptide and so refer to the amino acids corresponding to amino acid residues 1 to 139 of SEQ ID NO: 1 or 2 or the amino acids corresponding to amino acid residues 1 to 159 of SEQ ID NO: 1 or 2. Alternatively, the term flexible N-terminal region may exclude the signal peptide and so refer to the amino acids corresponding to amino acid residues 24 to 139 of SEQ ID NO: 1 or 2 or the amino acids corresponding to amino acid residues 24 to 159 of SEQ ID NO: 1 or 2. The present invention provides a PfRH5 fragment which lacks the flexible N-terminal region of PfRH5, wherein the flexible N-terminal region of PfRH5 is as defined herein. The flexible N-terminal region of PfRH5 as defined herein may comprise or consist of one of the recited sequences or variants thereof.

In embodiments where the PfRH5 protein of a *Plasmodium* parasite does not consist precisely of the sequence of SEQ ID NO: 1 or 2, i.e. a variant PfRH5 protein, the flexible N-terminal region of PfRH5 of said *Plasmodium* parasite will correspond to the N-terminal region defined by reference to SEQ ID NO: 1 or 2 and may be easily identified using standard techniques. In particular, it is envisaged that the flexible N-terminal region of such a variant PfRH5 protein will have at least 60%, at least 70%, at least 80%, at least 85%, at least 90%, at least 95%, at least 99% or more sequence identity with the flexible N-terminal region of PfRH5 as defined herein. Preferably the flexible N-terminal region has at least 90%, at least 95%, at least 99% or more sequence identity with the flexible N-terminal region of PfRH5 as defined herein.

According to the present invention, the flexible disordered central linker region of PfRH5 typically corresponds to amino acid residues 248 to 296 of SEQ ID NO: 1 or 2. The terms "flexible disordered central linker region", "flexible central linker region" and "flexible central linker" are used interchangeable herein. The flexible central linker of PfRH5 as defined herein may comprise or consist of one of the recited sequences or variants thereof.

In embodiments where the PfRH5 protein of a *Plasmodium* parasite does not consist precisely of the sequence of SEQ ID NO: 1 or 2, i.e. a variant PfRH5 protein, the flexible central linker of PfRH5 of said *Plasmodium* parasite will correspond to the flexible central linker defined by reference to SEQ ID NO: 1 or 2 and may be easily identified using standard techniques. In particular, it is envisaged that the flexible central linker of such a variant PfRH5 protein will have at least 60%, at least 70%, at least 80%, at least 85%, at least 90%, at least 95%, at least 99% or more sequence identity with the flexible central linker of PfRH5 as defined herein. Preferably the flexible central linker has at least 90%, at least 95%, at least 99% or more sequence identity with the flexible central linker of PfRH5 as defined herein.

The present invention provides PfRH5 fragments which lack the flexible central linker of PfRH5 as defined herein.

The present invention provides PfRH5 fragments that lack the flexible N-terminal region of PfRH5 and/or the flexible central linker region of PfRH5. In a preferred embodiment, the present invention provides PfRH5 fragments which lack both the flexible N-terminal region and the flexible central linker of PfRH5 as defined herein.

The PfRH5 fragments of the invention are antigens, specifically PfRH5 antigens. The terms PfRH5 antigen and PfRH5 fragment are used interchangeably herein when describing the PfRH5 fragments/antigens of the invention.

The term antigen or fragment as used herein refers to any peptide-based sequence that can be recognised by the immune system and/or that stimulates a cell-mediated immune response and/or stimulates the generation of antibodies. The PfRH5 fragments of the invention may be present in the form of a vaccine composition or vaccine formulation.

Typically the PfRH5 fragments of the invention bind to basigin (BSG), the red blood cell receptor for PfRH5. Binding of a PfRH5 fragment of the invention to basigin can be determined and/or quantified by any appropriate means. Standard methods for determining binding of a PfRH5 fragment of the invention to basigin, such as pull-down assays or surface plasmon resonance (SPR), are known in the art. In a preferred embodiment SPR is used to determine binding of PfRH5 fragments of the invention to basigin.

The PfRH5 fragments of the invention typically retain the same binding affinity for basigin as the full length PfRH5 protein. In the context of the present invention, this may mean having a binding affinity for basigin of at least 80%, at least 85%, at least 90%, at least 95%, at least 99% or more of that of the full length PfRH5 protein. Preferably the PfRH5 fragments of the invention have a binding affinity for basigin of at least 90%, at least 95%, at least 99% or more of that of the full length PfRH5 protein.

In some embodiments, the PfRH5 fragments of the invention have a binding affinity for basigin greater than that of the full length protein. For example, the PfRH5 fragments of the invention may have a binding affinity of at least 100%, at least 110%, at least 120%, or at least 150% or more of that of the full length PfRH5 protein.

In other embodiments, the PfRH5 fragments of the invention may have a binding affinity for basigin less than that of the full length protein. For example, the PfRH5 fragments of the invention may have a binding affinity of less than 80%, less than 70%, less than 60%, less than 50% or less of that of the full length PfRH5 protein.

The binding affinity of a PfRH5 fragment of the invention for basigin may be quantified in terms of dissociation constant ($K_d$). $K_d$ may be determined using any appropriate technique, but SPR is generally preferred in the context of the present invention. A PfRH5 fragment of the invention may bind to basigin with a $K_d$ of less than 10 µM, less than 9 µM, less than 8 µM, less than 7 µM, less than 6 µM, less than 5 µM, less than 4 µM, less than 3 µM, less than 2 µM, less than 1.5 µM, less than 1 µM, less than 0.5 µM or less. Typically a PfRH5 fragment of the invention binds to basigin with a $K_d$ of less 5 µM.

As discussed above, a PfRH5 fragment of the invention may have the same binding affinity for basigin as full length PfRH5, a higher binding affinity for basigin as full length PfRH5 or a lower binding affinity for basigin as full length PfRH5. Thus, a PfRH5 fragment of the invention may have the same $K_d$ for binding to basigin as full length PfRH5, a lower $K_d$ for binding to basigin as full length PfRH5 and a higher $K_d$ for binding to basigin as full length PfRH5 respectively.

As described herein, the PfRH5 fragment of the invention may lack the flexible N-terminal region of the full length PfRH5 protein, wherein typically the flexible N-terminal region comprises amino acids corresponding to amino acid residues 1 to 139 of SEQ ID NO: 1 or 2. In a preferred embodiment the PfRH5 fragment of the invention lacks the flexible N-terminal region corresponding to amino acid residues 1 to 159 of SEQ ID NO: 1 or 2. Alternatively or in addition, the PfRH5 fragment of the invention may lack the flexible central linker of the full length PfRH5 protein, wherein typically the flexible central liner corresponds to amino acid residues 248 to 296 of SEQ ID NO: 1 or 2. In a preferred embodiment, the PfRH5 fragment of the invention lacks both the flexible N-terminal region comprising amino acids corresponding to amino acid residues 1 to 139 of SEQ ID NO: 1 or 2 and the flexible central liner corresponding to amino acid residues 248 to 296 of SEQ ID NO: 1 or 2. In a more preferred embodiment, the PfRH5 fragment of the invention lacks both the flexible N-terminal region corresponding to amino acid residues 1 to 159 of SEQ ID NO: 1 or 2 and the flexible central liner corresponding to amino acid residues 248 to 296 of SEQ ID NO: 1 or 2.

The PfRH5 fragment of the invention may be a fragment of amino acid residues 140 to 526 of SEQ ID NO: 1 or 2, or a fragment of amino acid residues 160 to 526 of SEQ ID NO: 1 or 2. The PfRH5 fragment of the invention may be a fragment of an amino acid sequence having at least 70%, at least 80%, at least 90%, at least 95%, at least 99% or more sequence identity to amino acid residues 140 to 526 of SEQ ID NO: 1 or 2 or a fragment of an amino acid sequence having at least 70%, at least 80%, at least 90%, at least 95%, at least 99% or more sequence identity to amino acid residues 160 to 526 of SEQ ID NO: 1 or 2. For example, the PfRH5 fragment of the invention may have at least 90% sequence identity to amino acid residues 140 to 526 of SEQ ID NO: 1 or 2, or at least 90% sequence identity to amino acid residues 160 to 526 of SEQ ID NO: 1 or 2. In one embodiment, the PfRH5 fragment of the invention has the amino acid sequence of any one of SEQ ID NO: 3, 4, 5 or 6.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 143 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 148 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 149 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 153 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 158 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 187 of SEQ ID NO: 1 or 2.

The PfRH5 fragment of the invention may include a continuous region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 191 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 204 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 197 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 212 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 221 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 237 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 247 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 303 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 310 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 328 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 344 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 350 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 358 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 359 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 360 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 366 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 437 of SEQ ID NO: 1 or 2.

The PfRH5 fragment of the invention may include a region of at least five, at least six, at least seven, at least eight, at least nine, at least ten, at least 15, at least 16, at least 17, at least 18, at least 19, at least 20, at least 25, at least 30, at least 40, at least 50 or more amino acids that overlaps with amino acid residue 443 of SEQ ID NO: 1 or 2.

In the context of the present invention, the term overlaps means that there is at least one N-terminal amino acid and one C-terminal amino acid to the specified amino acid. For example, in the case of amino acid residue 191 of SEQ ID NO: 1 or 2, to have a continuous region of overlap with amino acid 191 would require the presence of at least amino acid residue 190 and amino acid residue 192, similarly to have a continuous region of overlap with amino acid 359 of SEQ ID NO: 1 or 2 would require the presence of at least amino acid residue 358 and amino acid residue 360. As another non-limiting example, if the continuous region of overlap with amino acid residue 191 of SEQ ID NO: 1 or 2 is five amino acids in length, the additional three amino acids may either be N- or C-terminal to amino acid residue 191 (i.e. amino acid residues 188 to 192, amino acid residues 189 to 193, or amino acid residues 190 to 194). As a further non-limiting example, if the continuous region of overlap with amino acid residue 359 of SEQ ID NO: 1 or 2 is ten amino acids in length, the additional amino acids may either be N- or C-terminal to amino acid residue 359 (i.e. amino acid residues 351 to 360, amino acid residues 352 to 361, amino acid residues 353 to 362, amino acid residues 354 to 363, amino acid residues 355 to 364, amino acid residues 356 to 365, amino acid residues 357 to 368 or amino acid residues 358 to 367).

In a preferred embodiment, the PfRH5 fragment of the invention includes a region of at least ten or more amino acids that overlaps with amino acid residue 191 of SEQ ID NO: 1 or 2, and/or a region of at least ten or more amino acids that overlaps with amino acid residue 359 of SEQ ID NO: 1 or 2. In a more preferred embodiment, the PfRH5 fragment of the invention includes a region of at least ten or more amino acids that overlaps with amino acid residue 191 of SEQ ID NO: 1 or 2, and a region of at least ten or more amino acids that overlaps with amino acid residue 359 of SEQ ID NO: 1 or 2.

In solving the crystal structure of the fragment of the PfRH5 protein lacking the flexible N-terminal region with basigin, the inventors have identified the key PfRH5 amino acid residues that contact basigin (see Table 1). The inventors have also solved the crystal structure of this N-terminal domain lacking PfRH5 fragment with two invasion inhibitory antibodies, again identifying the key PfRH5 contact amino acid residues (see Table 1). Accordingly, the present invention provides PfRH5 fragments specifically designed to include one or more of these key contact amino acid residues.

TABLE 1

Description of Interactions between PfRH5 and Basigin, monoclonal antibody QA1 and monoclonal antibody 9AD4.

| PfRH5 | | | Basigin | | | Type of |
| --- | --- | --- | --- | --- | --- | --- |
| Chain | Residue | Group | Chain | Residue | Group | interaction |
| N-terminal domain: | | | | | | |
| A/C | S197 | side chain | B/D | Q100 | side chain NH2 | hydrogen bond |
| A/C | S197 | side chain | B/D | E84 | side chain | hydrogen bond |
| A/C | F350 | side chain | B/D |  | hydrophobic pocket | hydrophobic |
| A/C | N352 | side chain CO | B/D | N98 | backbone NH | hydrogen bond |
| A/C | N354 | side chain NH2 | B/D | N98 | backbone CO | hydrogen bond |
| A/C | R357 | side chain | B/D | V26 | backbone CO | hydrogen bond |
| A/C | W447 | side chain | B/D |  | hydrophobic pocket | hydrophobic |

TABLE 1-continued

Description of Interactions between PfRH5 and Basigin, monoclonal antibody QA1 and monoclonal antibody 9AD4.

| | | | | | | |
|---|---|---|---|---|---|---|
| A/C | W447 | backbone CO | B/D | T28 | backbone NH | hydrogen bond |
| A/C | R448 | side chain | B/D | T25 | side chain | hydrogen bond |
| A/C | T449 | side chain | B/D | V26 | backbone NH | hydrogen bond |
| A/C | T449 | backbone NH | B/D | V26 | backbone CO | hydrogen bond |
| Linker: | | | | | | |
| A/C | Y200 | side chain | B/D | H102 | side chain | hydrogen bond |
| C-terminal domain: | | | | | | |
| A/C | | hydrophobic pocket | B/D | V131 | side chain | hydrophobic |
| A | | hydrophobic patch | B | P133 | side chain | hydrophobic |
| A | D207 | side chain | B | Q164 | side chain NH2 | hydrogen bond |
| C | E362 | side chain | D | K191 | side chain | hydrogen bond |
| C | E362 | side chain | D | S190 | side chain | hydrogen bond |

| PfRH5 | | | QA1 | | | Type of |
|---|---|---|---|---|---|---|
| Chain | Residue | Group | Chain | Residue | Group | interaction |
| Heavy chain: | | | | | | |
| A/D | K196 | side chain | B/E | N101 | side chain CO | hydrogen bond |
| A/D | K196 | side chain | B/E | D31 | backbone CO | hydrogen bond |
| A/D | S197 | backbone NH | B/E | D53 | side chain | hydrogen bond |
| A/D | Y346 | side chain | B/E | Y33 | side chain | pi stacking |
| A/D | N348 | side chain CO | B/E | G105 | backbone NH | hydrogen bond |
| A/D | N352 | side chain | B/E | Y33 | side chain | hydrogen bond |
| A/D | N352 | side chain | B/E | Y59 | side chain | hydrogen bond |
| A/D | N354 | backbone NH | B/E | Y57 | side chain | hydrogen bond |
| A/D | K452 | side chain | B/E | D104 | side chain | hydrogen bond |
| Light chain: | | | | | | |
| A/D | N347 | side chain NH2 | C/F | S95 | backbone CO | hydrogen bond |
| A/D | N348 | backbone NH | C/F | Y36 | side chain | hydrogen bond |
| A/D | N349 | backbone NH | C/F | Y34 | side chain | hydrogen bond |
| A/D | N349 | side chain CO | C/F | W96 | side chain | hydrogen bond |
| A/D | F350 | side chain | C/F | | hydrophobic surface | hydrophobic |
| A/D | Q451 | backbone CO | C/F | Y34 | side chain | hydrogen bond |

| PfRH5 | | | 9AD4 | | | Type of |
|---|---|---|---|---|---|---|
| Chain | Residue | Group | Chain | Residue | Group | interaction |
| Heavy chain: | | | | | | |
| A | A205 | backbone CO | B | Y103 | backbone CO | hydrogen bond (via H2O) |
| A | F209 | side chain | B | | hydrophobic surface | hydrophobic |
| A | Y335 | side chain | B | Y103 | backbone CO | hydrogen bond |

TABLE 1-continued

Description of Interactions between PfRH5 and Basigin, monoclonal antibody QA1 and monoclonal antibody 9AD4.

| A | N338 | side chain CO | B | W107 | side chain | hydrogen bond |
|---|---|---|---|---|---|---|
| A | L339 | side chain | B | | hydrophobic surface | hydrophobic |
| A | E341 | side chain | B | S52 | side chain | hydrogen bond |
| A | E341 | side chain | B | M54 | backbone CO | hydrogen bond |
| A | E341 | side chain | B | A55 | backbone CO | hydrogen bond |
| A | E341 | side chain | B | Y56 | backbone CO | hydrogen bond |
| A | Q342 | side chain CO | B | N53 | side chain NH2 | hydrogen bond |
| A | | hydrophobic pocket | B | F101 | side chain | hydrophobic |
| Light chain: | | | | | | |
| A | K212 | side chain | C | Y32 | backbone CO | hydrogen bond |
| A | D331 | side chain | C | Y32 | side chain | hydrogen bond |
| A | N334 | side chain NH2 | C | Y31 | side chain | hydrogen bond (via H2O) |

In more detail, the present inventors have identified amino acid residues corresponding to amino acid residues 197 to 200, 350 to 362 and 447 to 449 of SEQ ID NO: 1 or 2 as key amino acid residues of PfRH5 which contact basigin. The present inventors have also identified amino acid residues corresponding to amino acid residues 196, 197, 346 to 354 and 452 of SEQ ID NO: 1 or 2 as key amino acid residues of PfRH5 which contact inhibitory monoclonal antibody QA1. The present inventors have further identified amino acid residues corresponding to amino acid residues 205 to 212 and 331 to 342 of SEQ ID NO: 1 or 2 as key amino acid residues of PfRH5 which contact inhibitory monoclonal antibody 9AD4.

The invention therefore provides a fragment of PfRH5 which comprises at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20 or more of the key PfRH5 contact residues for basigin, monoclonal antibody QA1 and/or monoclonal antibody 9AD4.

A fragment of PfRH5 of the invention may comprise at least one, at least two, at least three, at least four, at least five, at least six, at least seven, at least eight, at least nine, at least ten, at least 11, at least 12, at least 13, at least 14, at least 15, at least 16, at least 17, at least 18, at least 19, or all 20 of the key PfRH5 contact residues identified for basigin.

A fragment of PfRH5 of the invention may comprise at least one, at least two, at least three, at least four, at least five, at least six, at least seven, at least eight, at least nine, at least ten, or all 11 of the key PfRH5 contact residues identified for monoclonal antibody QA1.

A fragment of PfRH5 of the invention may comprise at least one, at least two, at least three, at least four, at least five, at least six, at least seven, at least eight, at least nine, at least ten, at least 11, at least 12, at least 13, at least 14, at least 15, at least 16, at least 17, at least 18, at least 19, or all 20 of the key PfRH5 contact residues identified for monoclonal antibody 9AD4.

A PfRH5 fragment of the invention may comprise a combination of the key PfRH5 contact residues for basigin, monoclonal antibody QA1 and/or monoclonal antibody 9AD4. For example, a PfRH5 fragment of the invention may comprise: (i) at least one, at least two, at least three, at least four, at least five, at least six, at least seven, at least eight, at least nine, at least ten, at least 11, at least 12, at least 13, at least 14, at least 15, at least 16, at least 17, at least 18, at least 19, or all 20 of the key PfRH5 contact residues identified for basigin; and/or (ii) at least one, at least two, at least three, at least four, at least five, at least six, at least seven, at least eight, at least nine, at least ten, or all 11 of the key PfRH5 contact residues identified for monoclonal antibody QA1; and/or (iii) at least one, at least two, at least three, at least four, at least five, at least six, at least seven, at least eight, at least nine, at least ten, at least 11, at least 12, at least 13, at least 14, at least 15, at least 16, at least 17, at least 18, at least 19, or all 20 of the key PfRH5 contact residues identified for monoclonal antibody 9AD4.

In one embodiment, the PfRH5 fragment of the invention comprises all of the key PfRH5 contact residues identified for basigin, monoclonal antibody QA1 and monoclonal antibody 9AD4, i.e. amino acid residues corresponding to amino acid residues 196 to 200, 205 to 212, 331 to 342, 346 to 362 and 447 to 449 and 452 of SEQ ID NO: 1 or 2.

In one embodiment, the PfRH5 fragment of the invention comprises: (i) at least one, at least two, at least three, at least four, at least five, at least six, at least seven, at least eight, at least nine, at least ten, at least 11, at least 12, at least 13, at least 14, at least 15, at least 16, at least 17, at least 18, at least 19, at least 20 or more of the key PfRH5 contact residues for basigin (i.e. of amino acid residues corresponding to amino acid residues 197 to 200, 350 to 362 and 447 to 449 of SEQ ID NO: 1 or 2); and/or (ii) at least one, at least two, at least three, at least four, at least five, at least six, at least seven, at least eight, at least nine, at least ten, or all 11 of the key PfRH5 contact residues identified for monoclonal antibody QA1 (i.e. amino acid residues corresponding to amino acid residues 196, 197, 346 to 354 and 452 of SEQ ID NO: 1 or 2); and/or (iii) at least one, at least two, at least three, at least four, at least five, at least six, at least seven, at least eight, at least nine, at least ten, at least 11, at least 12, at least 13, at least 14, at least 15, at least 16, at least 17, at least 18, at least 19, or all 20 of the key PfRH5 contact residues identified for monoclonal antibody 9AD4 (i.e. amino acid residues corresponding to amino acid residues 205 to 212 and 331 to 342 of SEQ ID NO: 1 or 2); and wherein the RH5 fragment is ≤350, ≤300, ≤290, ≤280, ≤270, ≤260, ≤250, ≤240, ≤230, ≤220, ≤210, ≤200, ≤190, ≤180, ≤170, ≤160, ≤150, ≤140, ≤130, ≤120, ≤110 or ≤100 amino acids in length. In one embodiment said PfRH5 fragment is also greater than 20 amino acids in length.

The PfRH5 fragment of the invention may comprise all of the key PfRH5 contact residues for basigin (i.e. amino acid residues corresponding to amino acid residues 197 to 200, 350 to 362 and 447 to 449 of SEQ ID NO: 1 or 2) and be ≤350, ≤300, ≤290, ≤280, ≤270 or ≤260 amino acids in length. In one embodiment said PfRH5 fragment is also greater than 20 amino acids in length. In a preferred embodiment, the PfRH5 fragment of the invention comprises all of the key PfRH5 contact residues for basigin (i.e. amino acid residues corresponding to amino acid residues 197 to 200, 350 to 362 and 447 to 449 of SEQ ID NO: 1 or 2) and is 253 amino acids in length.

The PfRH5 fragment of the invention may comprise all of the key PfRH5 contact residues for monoclonal antibody QA1 (i.e. amino acid residues corresponding to amino acid residues 196, 197, 346 to 354 and 452 of SEQ ID NO: 1 or 2) and be ≤350, ≤300, ≤290, ≤280, ≤270 or ≤260 amino acids in length. In one embodiment said PfRH5 fragment is also greater than 20 amino acids in length. In a preferred embodiment, the PfRH5 fragment of the invention comprises all of the key PfRH5 contact residues for monoclonal antibody QA1 (i.e. amino acid residues corresponding to amino acid residues 196, 197, 346 to 354 and 452 of SEQ ID NO: 1 or 2) and is 257 amino acids in length.

The PfRH5 fragment of the invention may comprise all of the key PfRH5 contact residues for monoclonal antibody 9AD4 (i.e. amino acid residues corresponding to amino acid residues 205 to 212 and 331 to 342 of SEQ ID NO: 1 or 2); and be ≤350, ≤300, ≤290, ≤280, ≤270, ≤260, ≤250, ≤240, ≤230, ≤220, ≤210, ≤200, ≤190, ≤180, ≤170, ≤160, ≤150 or ≤140 amino acids in length. In one embodiment said PfRH5 fragment is also greater than 20 amino acids in length. In a preferred embodiment, the PfRH5 fragment of the invention comprises all of the key PfRH5 contact residues for monoclonal antibody 9AD4 (i.e. amino acid residues corresponding to amino acid residues 205 to 212 and 331 to 342 of SEQ ID NO: 1 or 2) and is 138 amino acids in length.

A PfRH5 fragment of the invention may comprise any combination of the key contact residues for basigin, monoclonal antibody QA1 and monoclonal antibody 9AD4. In one embodiment, a PfRH5 fragment of the invention comprises all of the key contact residues for basigin, monoclonal antibody QA1 and monoclonal antibody 9AD4, i.e. amino acid residues corresponding to amino acid residues 196 to 200, 205 to 212, 331 to 342, 346 to 362, 447 to 449 and 452 of SEQ ID NO: 1 or 2 and is ≤350, ≤300, ≤290, ≤280, ≤270, ≤260 amino acids in length (for example 257 amino acids in length). In one embodiment said PfRH5 fragment is also greater than 20 amino acids in length.

In a preferred embodiment, the PfRH5 fragments of the invention are discontinuous PfRH5 fragments. A discontinuous PfRH5 fragment is one which is lacking at least one region of continuous amino acids from within the full length PfRH5 protein, such that the discontinuous fragment has at least one gap or break in the full length PfRH5 sequence.

Thus, a discontinuous PfRH5 fragment of the invention comprises at least two regions, at least three regions, at least four regions, at least five regions, at least six regions, at least seven regions, at least eight regions, at least nine regions, at least ten regions, or more regions of continuous amino acid sequence from the full length PfRH5 protein which are separated in the full length PfRH5 protein, but which form a single polypeptide in the discontinuous fragment.

For example, full length PfRH5 comprises a flexible central linker as described herein, at amino acid residues corresponding to amino acid residues 248 to 296 of SEQ ID NO: 1 or 2. The present invention provides a PfRH5 lacking this flexible central linker. A PfRH5 fragment comprising, for example, amino acid residues corresponding to amino acid residues 140 to 247 and 297 to 526 of SEQ ID NO: 1 or 2 as a single polypeptide is a discontinuous PfRH5 according to the present invention. Another example of a discontinuous PfRH5 fragment according to the present invention is a PfRH5 fragment comprising amino acid residues corresponding to amino acid residues 160 to 247 and 297 to 526 of SEQ ID NO: 1 or 2 as a single polypeptide.

In one embodiment, a discontinuous PfRH5 fragment of the invention lacks a flexible central linker as described herein, particularly a flexible central linker at amino acid residues corresponding to amino acid residues 248 to 296 of SEQ ID NO: 1 or 2. In a preferred embodiment, a discontinuous PfRH5 fragment of the invention also lacks the flexible N-terminal region as described herein, particularly a flexible N-terminal region comprising amino acids corresponding to amino acids 1 to 139 of SEQ ID NO: 1 or 2 or a flexible N-terminal region corresponding to amino acid residues 1 to 159 of SEQ ID NO: 1 or 2. In a particularly preferred embodiment, a discontinuous PfRH5 fragment of the present invention lacks both a flexible central linker as described herein and a flexible N-terminal region as described herein. Such a preferred PfRH5 fragment may lack a flexible central linker at amino acid residues corresponding to amino acid residues 248 to 296 of SEQ ID NO: 1 or 2 and a flexible N-terminal region comprising amino acids corresponding to amino acids 1 to 139 of SEQ ID NO: 1 or 2. Alternatively, a preferred PfRH5 fragment may lack a flexible central linker at amino acid residues corresponding to amino acid residues 248 to 296 of SEQ ID NO: 1 or 2 and a flexible N-terminal region corresponding to amino acids 1 to 159 of SEQ ID NO: 1 or 2.

A discontinuous PfRH5 fragment of the invention may have at least 70%, at least 80%, at least 85%, at least 90%, at least 95%, at least 99% or more sequence identity to SEQ ID NO: 5 or 6. Typically such a discontinuous PfRH5 fragment of the invention has at least 90%, at least 95%, at least 99% or more sequence identity to any one of SEQ ID NO: 77 to 10.

Any disclosure, feature and/or reference herein to a PfRH5 fragment of the invention may apply to continuous PfRH5 fragments of the invention and/or to discontinuous PfRH5 fragments of the invention unless otherwise stated.

PfRH5 fragments of the present invention are typically greater than 20 amino acids in length. PfRH5 fragments of the present invention may comprise or consist of at least 21, at least 30, at least 40, at least 50, at least 60, at least 70, at least 80, at least 90, at least 100, 110, 120, 130, 140, 150, 160, 170, 180, 190, 200, 210, 220, 230, 240, 250, 260, 270, 280, 290, 300, 310, 320, 330, 340, 350, 360, 370, 380 or more amino acid residues in length. PfRH5 fragments of the invention, including discontinuous PfRH5 fragments of the invention, may comprise regions of consecutive amino acids from the full length PfRH5 protein. For example, the PfRH5 fragments of the invention may comprise regions of at least 21, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220 or more consecutive amino acid residues in length. The fragments of the invention may be linear or branched, preferably linear. The fragments of the invention have a common antigenic cross-reactivity with the PfRH5 antigen.

The PfRH5 fragments of the invention may have substitutions at amino acid residues corresponding to amino acid residue 216 and/or amino acid residue 286 and/or amino acid residue 299 of SEQ ID NO: 1 or 2, wherein the amino acid T is replaced by an amino acid other than T. In one embodiment amino acid residues corresponding to amino acid residues 216, 286 and/or 299 of SEQ ID NO: 1 or 2 are replaced with A. Typically, amino acid residues corresponding to amino acid residues 216, 286 and 299 of SEQ ID NO: 1 or 2 are each replaced with A.

The PfRH5 fragments of the invention embrace fragments of variants of the full length PfRH5 protein, wherein said variants exhibit at least 90%, 91%, 92%, 93%, 94%, 95%, 96%, 97% 98%, 99% or more identity with SEQ ID NO: 1 or 2.

SEQ ID NO: 1 consists of 526 amino acid residues. Variants of SEQ ID NO: 1 or 2 are encompassed as set out above and may additionally or alternatively include amino acid sequences with one or more amino acid substitutions, deletions or insertions. Substitutions are particularly envisaged, as are N- and C-terminal deletions. Substitutions include conservative substitutions.

For example, a variant of SEQ ID NO: 1 or 2 may comprise an N-terminal deletion of at least 1 consecutive amino acid residues (e.g. at least 30, 35, 40, 45 or 50 consecutive amino acid residues) in length, and/or a C-terminal deletion of at least 1 consecutive amino acid residues (e.g. at least 5, 10, 15, 20, 25, 30, 35, 40, 45 or 50 consecutive amino acid residues) in length.

Conventional methods for determining amino acid sequence identity are known in the art. The terms "sequence identity" and "sequence homology" are considered synonymous in this specification.

By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (e.g. GAP, BESTFIT, FASTA or TFASTA), or BLAST and BLAST 2.0 algorithms.

The BLOSUM62 table shown below is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915-10919, 1992; incorporated herein by reference). Amino acids are indicated by the standard one-letter codes. The percent identity is calculated as:

$$\frac{\text{Total number of identical matches}}{[\text{length of the longer sequence plus the number of gaps introduced into the longer sequence in order to align the two sequences}]} \times 100$$

| BLOSUM62 table | | | | | | | | | | | | | | | | | | | | |
|---|---|---|---|---|---|---|---|---|---|---|---|---|---|---|---|---|---|---|---|---|
| | A | R | N | D | C | Q | E | G | H | I | L | K | M | F | P | S | T | W | Y | V |
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

In a homology comparison, the identity may exist over a region of the sequences that is at least 10 amino acid residues in length (e.g. at least 15, 20, 30, 40, 50, 75, 100, 150, 200, 250, 300, 350, 400, 450, 500 or 520 amino acid residues in length)—e.g. up to the entire length of the reference sequence.

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic:

glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

The PfRH5 fragments exemplified herein (namely PfRH5ΔN and PfRH5ΔNL) are derived from the 7G8 strain of P. falciparum (i.e. the PfRH5 protein sequence of SEQ ID NO: 2). PfRH5 fragments, particularly fragments corresponding to PfRH5ΔN and PfRH5ΔNL, derived from other P. falciparum strains are also encompassed by the present invention. In particular, the present invention encompasses PfRH5 fragments derived from the PfRH5 protein of the 3D7, 7G8 and FVO strains, preferably the PfRH5 of the 3D7 strain (SEQ ID NO: 1). The amino acid sequences of the PfRH5 proteins from the 7G8 and 3D7 strains are identical except for a single amino acid substitution: position 203 is a tyrosine (Y) in the 7G8 strain and a cysteine (C) in the 3D7 strain. Full length RH5 from the 3D7 strain has been shown to produce a higher quality antibody response than full length RH5 from the 7G8 strain. Accordingly, in one embodiment the PfRH5 fragments of the invention are derived from the PfRH5 protein from the 3D7 strain.

The PfRH5 fragments of the invention may additionally comprise a leader sequence, for example to assist in the recombinant production and/or secretion of the PfRH5 fragment. Any suitable leader sequence may be used, including conventional leader sequences known in the art. Suitable leader sequences include Bip leader sequences, which are commonly used in the art to aid secretion from insect cells and human tissue plasminogen activator leader sequence (tPA), which is routinely used in viral and DNA based vaccines and for protein vaccines to aid secretion from mammalian cell expression platforms.

The PfRH5 fragments of the invention may additionally comprise an N- or C-terminal tag, for example to assist in the recombinant production and/or purification of the PfRH5 fragment. Any N- or C-terminal tag may be used, including conventional tags known in the art. Suitable tags sequences include C-terminal hexa-histidine tags and the "C-tag" (the four amino acids EPEA at the C-terminus), which are commonly used in the art to aid purification from heterologous expression systems, e.g. insect cells, mammalian cells, bacteria, or yeast. In other embodiments, the PfRH5 fragments of the invention are purified from heterologous expression systems without the need to use a purification tag.

The PfRH5 fragments of the invention may comprise a leader sequence and/or a tag as defined herein. Typically, the PfRH5 fragments of the invention comprise both a leader sequence and a C-terminal tag. For example, the PfRH5 fragments of the invention may comprise a Bip leader sequence and a C-terminal hexa-histidine tag. Such PfRH5 fragments of the invention may have at least 70%, at least 80%, at least 85%, at least 90%, at least 95%, at least 99% or more sequence identity with any one of SEQ ID NOs: 11 to 14.

As described herein, the PfRH5 fragments of the invention raise antibodies that inhibit the growth of malarial parasites, i.e. Plasmodium parasites, preferably across a plurality of strains of blood-stage Plasmodium parasites. In a more preferred embodiment, the PfRH5 fragments of the invention raise antibodies that inhibit the growth of Plasmodium falciparum parasites, and more preferably across a plurality of strains of blood-stage P. falciparum parasites. The effectiveness of the PfRH5 fragments of the invention may be quantified using any appropriate technique and measured in any appropriate units. For example, the effectiveness of the PfRH5 fragments of the invention may be given in terms of their growth inhibitory activity (GIA), half maximal effective concentration ($EC_{50}$), antibody titre stimulated (in terms of antibody units, AU) and/or $EC_{50}$ in terms of AU. The latter of these gives an indication of the quality of the antibody response stimulated by the PfRH5 fragment of the invention. Any appropriate technique may be used to determine the GIA, $EC_{50}$, AU or $EC_{50}$/AU. Exemplary techniques are described in the examples and conventional techniques are known in the art.

Typically, the PfRH5 fragments of the invention induce antibodies that have a growth inhibitory activity (GIA) of at least 30%, at least 40%, at least 50%, at least 60%, at least 70%, at least 80%, at least 90% or more against Plasmodium parasites. In a preferred embodiment, the PfRH5 fragments of the invention induce antibodies that have a growth inhibitory activity (GIA) of at least 50%, at least 60%, at least 70%, at least 80%, at least 90% or more against Plasmodium parasites.

The growth inhibitory activity (GIA) may be measured at any appropriate concentration of the antibodies raised against the PfRH5 fragment, for example the GIA may be measured at 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 2 mg/ml, 3 mg/ml, 4 mg/ml, 5 mg/ml, 6 mg/ml, 7 mg/ml, 8 mg/ml, 9 mg/ml, or 10 mg/ml of purified IgG antibody. For example, the vaccine of the invention may comprise a PfRH5 fragment which will result in antibodies that give a GIA of least 20%, at least 30%, at least 50% and preferably at least 70% against the blood-stage Plasmodium parasite, at an IgG concentration of 10 mg/ml IgG, for example rabbit IgG.

Preferably the PfRH5 fragment of the invention is capable of inducing antibodies which exert similarly high levels of GIA against both the vaccine-homologous clone, 3D7, and against a vaccine-heterologous strain, FVO. The total IgG induced by the PfRH5 fragment of the invention has an $EC_{50}$ which is comparable to total IgG against full length PfRH5, and preferably significantly lower than the $EC_{50}$ against full length PfRH5. The total IgG induced by the PfRH5 fragment of the invention preferably has an $EC_{50}$ significantly lower than that of the anti-PfAMA1 BG98 standard (Faber et al. Infect. Immun. (2013), (81(5);1479-90; incorporated herein by reference). Typically a PfRH5 fragment of the invention induces IgG antibodies that have a total IgG $EC_{50}$ value of less than 10 mg/ml, less than 9 mg/ml, less than 8 mg/ml, less than 7 mg/ml, less than 6 mg/ml, less than 5 mg/ml, less than 4 mg/ml, less than 3 mg/ml, less than 2.5 mg/ml, less than 2 mg/ml, less than 1.5 mg/ml, less than 1 mg/ml, less than 0.5 mg/ml or less.

Typically the vaccine of the invention comprises a PfRH5 fragment of the invention which will raise antibodies that result in a GIA of at least 30%, at least 40%, at least 50%, at least 60%, at least 70%, at least 80%, at least 90% or more against the blood-stage Plasmodium parasite. In a preferred embodiment, the vaccine of the invention comprises a PfRH5 fragment of the invention which will raise antibodies that result in a GIA of at least 50% against the blood-stage Plasmodium parasite.

PfRH5 induces antibodies which are effective against genetically diverse strains of the *Plasmodium* parasite. This is likely to be of importance in achieving vaccine efficacy against the variety of strains circulating in the natural environment. Accordingly, in a preferred embodiment, the vaccine of the invention will raise antibodies that result in a GIA of at least 30% at least 40%, at least 50%, at least 60%, at least 70%, at least 80%, at least 90% or more against a plurality of genetic strains of the blood-stage *Plasmodium* parasite. In a preferred embodiment, the vaccine of the invention will raise antibodies that result in a GIA of at least 50% against a plurality of genetic strains of the blood-stage *Plasmodium* parasite.

Thus the vaccine of the invention can lead to improved outcomes after infection by *P. falciparum* and/or other species of the *Plasmodium* parasite. Monoclonal antibodies, DNA oligonucleotide aptamers, RNA oligonucleotide aptamers, and other engineered biopolymers against a PfRH5 fragment of the invention may also be able to replicate the activity of the vaccine-induced polyclonal antibodies described here. As a vaccine, PfRH5 fragments of the invention are likely amenable to expression by recombinant viral vectored vaccines, as well as nucleic acid-based vaccines such as RNA or DNA; and recombinant protein or virus-like particles (VLPs) expressed in mammalian expression systems or insect cell systems. It may also be possible to express the PfRH5 fragments of the invention as proteins or VLPs in bacteria or yeast, as well as plant/algae systems.

The vaccine of the invention may comprise a combination of a PfRH5 fragment of the invention and one or more additional antigen(s) or fragment(s) thereof (preferably a PfAARP antigen or fragment thereof) that raise antibodies that give at least 70%, at least 80%, at least 85%, at least 90%, at least 95% or at least 99% GIA at a total antibody concentration of 10 mg/mL IgG, for example rabbit IgG. This combination is preferably equally effective against both the vaccine-homologous 3D7 clone and the vaccine-heterologous FVO strain.

The amount of antibody produced may be quantified using any appropriate method, with standard techniques being known in the art. For example, the amount of antibody produced may be measured by ELISA in terms of the serum IgG response induced by the PfRH5 fragment of the invention. The amount of antibody produced may be given in terms of arbitrary antibody units (AU). Typically, a PfRH5 fragment of the invention will produce an anti-PfRH5 fragment antibody response of at least 200 AU, at least 300 AU, at least 400 AU, at least 500 AU, at least 600 AU, at least 700 AU, at least 800 AU, at least 900 AU, at least 1000 AU or more.

The PfRH5 fragment of the invention may have a comparable immunogenicity when compared with the full length PfRH5 antigen.

The immune response (or immunogenicity) to a PfRH5 fragment of the invention, particularly the antibody response, may be given as the half-maximal effective concentration in terms of the amount of antibody produced, i.e. $EC_{50}/AU$. This gives an indication of the quality of the immune response generated to the PfRH5 fragments. For example, a low $EC_{50}$ (i.e. effective response) but a high number of antibody units generated is less effective (and gives a higher $EC_{50}/AU$) than a low $EC_{50}$ with a low number of antibody units. This value thus indicates the quality of the antibody response by representing the functional anti-parasitic antibody activity (measured as the $EC_{50}$ in the assay of GIA) as a proportion of the total amount of anti-PfRH5 IgG antibody produced (measured by ELISA in AU). A more effective vaccine thus induces 50% GIA (the $EC_{50}$ with less antibody (lower AU).

Typically a PfRH5 fragment of the invention results in an $EC_{50}/AU$ value of less than 500, less than 400, less than 300, less than 250, less than 200, less than 150, less than 100, less than 90, less than 80, less than 70, less than 60, less than 50, less than 40, less than 30, less than 20, less than 10 or less. In a preferred embodiment, a PfRH5 fragment of the invention results in an $EC_{50}/AU$ value of less than 400.

Typically a PfRH5 fragment of the invention elicits an improved immune response, particularly an improved antibody response, compared with the full length PfRH5 protein. For example, a PfRH5 fragment of the invention may elicit antibodies with a greater GIA, a lower $EC_{50}$, and/or a lower $EC_{50}/AU$ than the full-length PfRH5 protein.

In one embodiment, the present invention excludes one or more PfRH5 fragments selected from: amino acid residues corresponding to amino acid residues 138 to 526 of SEQ ID NO: 1 or 2; amino acid residues corresponding to amino acid residues 143 to 526 of SEQ ID NO: 1 or 2; amino acid residues corresponding to amino acid residues 148 to 526 of SEQ ID NO: 1 or 2; amino acid residues corresponding to amino acid residues 149 to 526 of SEQ ID NO: 1 or 2; amino acid residues corresponding to amino acid residues 153 to 526 of SEQ ID NO: 1 or 2; amino acid residues corresponding to amino acid residues 158 to 526 of SEQ ID NO: 1 or 2; amino acid residues corresponding to amino acid residues 191 to 359 of SEQ ID NO: 1 or 2; amino acid residues corresponding to amino acid residues 191 to 360 of SEQ ID NO: 1 or 2; amino acid residues corresponding to amino acid residues 204 to 350 of SEQ ID NO: 1 or 2; amino acid residues corresponding to amino acid residues 204 to 360 of SEQ ID NO: 1 or 2; amino acid residues corresponding to amino acid residues 204 to 344 of SEQ ID NO: 1 or 2; amino acid residues corresponding to amino acid residues 187 to 197 of SEQ ID NO: 1 or 2; amino acid residues corresponding to amino acid residues 212 to 221 of SEQ ID NO: 1 or 2; amino acid residues corresponding to amino acid residues 237 to 247 of SEQ ID NO: 1 or 2; amino acid residues corresponding to amino acid residues 303 to 310 of SEQ ID NO: 1 or 2; amino acid residues corresponding to amino acid residues 358 to 366 of SEQ ID NO: 1 or 2; amino acid residues corresponding to amino acid residues 437 to 443 of SEQ ID NO: 1 or 2; amino acid residues corresponding to amino acid residues 203 to 224 of SEQ ID NO: 1 or 2; amino acid residues corresponding to amino acid residues 203 to 317 of SEQ ID NO: 1 or 2; amino acid residues corresponding to amino acid residues 203 to 329 of SEQ ID NO: 1 or 2; amino acid residues corresponding to amino acid residues 203 to 345 of SEQ ID NO: 1 or 2; amino acid residues corresponding to amino acid residues 203 to 351 of SEQ ID NO: 1 or 2; amino acid residues corresponding to amino acid residues 224 to 317 of SEQ ID NO: 1 or 2; amino acid residues corresponding to amino acid residues 224 to 329 of SEQ ID NO: 1 or 2; amino acid residues corresponding to amino acid residues 224 to 345 of SEQ ID NO: 1 or 2; amino acid residues corresponding to amino acid residues 224 to 351 of SEQ ID NO: 1 or 2; amino acid residues corresponding to amino acid residues 317 to 329 of SEQ ID NO: 1 or 2; amino acid residues corresponding to amino acid residues 317 to 345 of SEQ ID NO: 1 or 2; amino acid residues corresponding to amino acid residues 317 to 351 of SEQ ID NO: 1 or 2; amino acid residues corresponding to amino acid residues 329 to 345 of SEQ ID NO: 1 or 2; amino acid residues corresponding to amino acid residues 329 to 351 of SEQ ID NO: 1 or 2; amino acid residues corresponding to amino acid residues 345 to 351 of SEQ ID NO: 1 or 2; amino acid residues corresponding to amino acid residues 273 to 293 of SEQ ID NO: 1 or 2; amino acid residues corresponding to amino acid residues 201 to 220 of SEQ ID NO: 1 or 2; amino acid residues corresponding to amino acid residues 221 to 240 of SEQ ID NO: 1 or 2; amino acid residues corresponding to amino acid residues 361 to 380 of SEQ ID NO: 1 or 2; amino acid residues corresponding to amino acid residues 381 to 400 of SEQ ID NO: 1 or 2; amino acid residues corresponding to amino acid residues 461 to 480 of SEQ ID NO: 1 or 2; amino acid residues corresponding to amino acid residues 501 to 520 of SEQ ID NO: 1 or 2; and/or amino acid residues corresponding to amino acid residues 204 to 328 of SEQ ID NO: 1 or 2, or any combination thereof.

Combinations of Antigens

The present inventors have also found that even greater efficacy can be achieved through combining PfHR5 with one or more of other *P. falciparum* antigens. GIA assays involving such combinations have demonstrated an effect which is greater than the sum of inhibition with individual antibodies, i.e. a synergistic effect. This was found to be the case even though other members of the PfRH family do not appear to be particularly effective in the GIA assay.

Accordingly, the PfRH5 fragment of the invention may be used in combination with one or more additional malarial antigen(s), or fragment thereof, including malarial antigens already known in the art.

For example, the present invention provides a Reticulocyte-binding protein Homologue 5 (PfRH5) fragment of the invention in combination with one or more antigens selected from the group consisting of PfAMA1, PfEBA175, PfRH1, PfRH2a, PfRH2b or PfRH4, or PfAARP, or a fragment thereof. *P. falciparum* apical asparagine rich protein (PfAARP) is encoded by the *P. falciparum* clone 3D7 gene PF3D7_0423400 (previously known as MAL4P1.216 or PFD1105w). In particular, the present invention provides the PfRH5 fragment of the invention together with one or more of the PfEBA175, PfRH1, PfRH2a, PfRH2b, PfRH4 or PfAARP antigens, or a fragment thereof.

A particularly preferred embodiment includes the PfRH5 fragment of the invention together with a PfAARP antigen or fragment thereof. Such a combination may provide >90% GIA at a total antibody concentration of 0.625 mg/mL mouse IgG. Such a combination may be equally effective against both the vaccine-homologous 3D7 clone and the vaccine-heterologous FVO strain. One or more additional malarial antigen(s) can be used in combination with the PfRH5 fragment and PfAARP (or fragment) combination.

In one embodiment, the antigens or fragments thereof are present in the form of a vaccine formulation.

The combination of the invention may be present in a single vaccine product capable of inducing antibodies against both the PfRH5 fragment and the one or more additional antigen or fragment thereof. Alternatively the combination of the invention can be effected by mixing two separate recombinant protein vaccines (Pichyangkul, S., et al., *Vaccine*, 2009. 28(2): p. 452-62; and Ellis, R. D., et al., *PLoS One*, 2012. 7(10): p. e46094; both of which are incorporated herein by reference), or by co-delivering the PfRH5 fragment and one or more additional antigens or fragments thereof using vaccine platforms such as particle-based protein vaccine delivery (Bachmann, M. F., et al., *Nat Rev Immunol*, 2010. 10(11): p. 787-96; incorporated herein by reference), or virus-like particles (VLP), or by fusing or conjugating the PfRH5 fragment and the one or more additional antigen or fragment thereof to a construct or constructs that allow for particle formation and/or enhanced immunogenicity (Spencer, A. J., et al., *PLoS One*, 2012. 7(3): p. e33555; and Wu, Y., et al., *Proc Natl Acad Sci USA*, 2006. 103(48): p. 18243-8; both of which are incorporated herein by reference). In one embodiment, the PfRH5 fragment and the one or more additional antigen or fragment thereof may be delivered as a fusion protein (Biswas, S., et al., *PLoS One*, 2011. 6(6): p. e20977; incorporated herein by reference). Additionally or alternatively, the PfRH5 fragment and the one or more additional antigen or fragment thereof may be delivered using a mixture of viral vectors expressing the individual antigens (Forbes, E. K., et al., *J Immunol*, 2011. 187(7): p. 3738-50; and Sheehy, S. H., et al., *Mol Ther*, 2012. 20(12): p. 2355-68; both of which are incorporated herein by reference), or viral vectors co-expressing both the PfRH5 fragment and the one or more additional antigen or fragment thereof. Where the PfRH5 fragment and the one or more additional antigen or fragment thereof are co-expressed, this may be in the form of a fusion protein (Porter, D. W., et al., *Vaccine*, 2011. 29(43): p. 7514-22; incorporated herein by reference), or the PfRH5 fragment and the one or more additional antigen or fragment thereof expressed as separate transcripts under the control of separate promoters (Bruder, J. T., et al., *Vaccine*, 2010. 28(18): p. 3201-10; and Tine, J. A., et al., *Infect Immun*, 1996. 64(9): p. 3833-44; both of which are incorporated herein by reference), or the PfRH5 fragment and the one or more additional antigen or fragment thereof translated as a single polypeptide which undergoes cleavage to yield two separate antigens (Ibrahimi, A., et al., *Hum Gene Ther*, 2009. 20(8): p. 845-60; incorporated herein by reference).

Vectors and Plasmids

The present invention provides a vector that expresses a PfRH5 fragment of the invention. Typically the vector is present in the form of a vaccine formulation.

The present invention further provides a vector that expresses PfRH5 fragment of the invention, and one or more antigens selected from the group consisting of PfAMA1, PfEBA175, PfRH1, PfRH2a, PfRH2b, PfRH4, or PfAARP or a fragment thereof. In another aspect, the present invention provides a vector that expresses a PfRH5 fragment of the invention, together with a further vector that expresses one or more antigens selected from the group consisting of PfAMA1, PfEBA175, PfRH1, PfRH2a, PfRH2b, PfRH4, or PfAARP, or a fragment thereof. Preferred embodiments include a vector or vectors which express a PfRH5 fragment of the invention together with one or more of the PfEBA175, PfRH1, PfRH2a, PfRH2b, PfRH4 or PfAARP antigens, or a fragment thereof. The vector or vectors may be present in the form of a vaccine formulation.

The vector may be a viral vector. Such a viral vector may be an adenovirus (of a human serotype such as AdHu5, a simian serotype such as ChAd63, ChAdOX1 or ChAdOX2, or another form) or poxvirus vector (such as a modified vaccinia Ankara (MVA)). ChAdOX1 and ChAdOX2 are disclosed in WO2012/172277. ChAdOX2 is a BAC-derived and E4 modified AdC68-based viral vector.

Viral vectors are usually non-replicating or replication impaired vectors, which means that the viral vector cannot replicate to any significant extent in normal cells (e.g. normal human cells), as measured by conventional means—e.g. via measuring DNA synthesis and/or viral titre. Non-replicating or replication impaired vectors may have become so naturally (i.e. they have been isolated as such from nature) or artificially (e.g. by breeding in vitro or by genetic manipulation). There will generally be at least one cell-type in which the replication-impaired viral vector can be grown—for example, modified vaccinia Ankara (MVA) can be grown in CEF cells. In one embodiment, the vector is selected from a human or simian adenovirus or a poxvirus vector.

Typically, the viral vector is incapable of causing a significant infection in an animal subject, typically in a mammalian subject such as a human or other primate.

The invention further provides a DNA vector that expresses a PfRH5 fragment of the invention, such as a plasmid-based DNA vaccine. In one embodiment the DNA vector is capable of expression in a mammalian cell expression system, such as an immunised cell.

The vector may be a RNA vector, such as a self-amplifying RNA vaccine (Geall, A. J. et al., Proc Natl Acad Sci USA 2012; 109(36) pp. 14604-9; incorporated herein by reference).

The present invention also provides virus-like particles (VLP) and/or fusion proteins comprising a PfRH5 fragment of the invention, as described herein. References herein to vectors of the invention may apply equally to VLP and/or fusion proteins of the invention.

Antibodies and Other Binding Compounds

As set out above, PfRH5 is a component of the mechanism by which the *Plasmodium* parasite invades RBCs. Compounds that specifically bind to PfRH5 inhibit this process and prevent the invasion of RBCs.

Accordingly, the present invention also provides binding compounds to Reticulocyte-binding protein Homologue 5 (PfRH5) fragments of the invention.

The present invention also provides binding compounds to PfRH5 fragments of the invention, in combination with binding compounds to any of PfAMA1, PfEBA175, PfRH1, PfRH2a, PfRH2b, PfRH4 or PfAARP, or fragments thereof. Particularly preferred embodiments include binding compounds to a PfRH5 fragment of the invention in combination with binding compounds to one or more of the PfEBA175, PfRH1, PfRH2a, PfRH2b, PfRH4 or PfAARP antigens or a fragment thereof.

The binding compound may be an antibody, such as a monoclonal antibody or polyclonal antibody. The binding compound may be an antigen-binding fragment of a monoclonal or polyclonal antibody, or a peptide which binds to a PfRH5 fragment of the invention with specificity. The antibody may be a Fab, F(ab')2, Fv, scFv, Fd or dAb.

In another embodiment, the binding compound may be an oligonucleotide aptamer. The aptamer may bind to a PfRH5 fragment of the invention. The aptamer may specifically bind to PfRH5 or a fragment thereof.

Aptamers to PfRH5 may inhibit *Plasmodium* parasite growth in a GIA assay. Such aptamers can be found by known methods (e.g. as set out in D. H. J. Bunka, P. G. Stockley, *Nature Reviews Microbiology* 4, 588 (2006)). The aptamer may be optimised to render it suitable for therapeutic use, e.g. it may be conjugated to a monoclonal antibody to modify its pharmacokinetics (e.g. half-life and biodistribution) and/or recruit Fc-dependent immune functions.

The binding compound of the invention may be used in combination with a binding compound to one or more additional malarial antigen(s), including malarial antigens already known in the art. In a preferred embodiment, the present invention relates to the combination of a binding compound to the PfRH5 fragment of the invention with a binding compound to the PfAARP antigen or fragment thereof. One or more binding compound(s) to one or more additional malarial antigens can be used together with the combination of a binding compound to PfRH5 fragment and the binding compound to PfAARP (or fragment).

Typically the binding compounds of the invention are specific for the PfRH5 fragment of the invention. By specific, it will be understood that a binding compound binds to the molecule of interest, in this case the PfRH5 fragment of the invention, with no significant cross-reactivity to any other molecule, particularly any other nucleic acid. For example, a binding compound or antibody that is specific for a PfRH5 fragment of the invention will show no significant cross-reactivity with human neutrophil elastase. Cross-reactivity may be assessed by any suitable method. Cross-reactivity of a binding compound (e.g. antibody) for the PfRH5 fragment with a molecule other than the PfRH5 fragment may be considered significant if the binding compound (e.g. antibody) binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to the PfRH5 fragment. A binding compound that is specific for the PfRH5 fragment may bind to another molecule such as human neutrophil elastase at less than 90%, 85%, 80%, 75%, 70%, 65%, 60%, 55%, 50%, 45%, 40%, 35%, 30%, 25% or 20% the strength that it binds to the PfRH5 fragment. Preferably, the binding compound (e.g. antibody) binds to the other molecule at less than 20%, less than 15%, less than 10% or less than 5%, less than 2% or less than 1% the strength that it binds to the PfRH5 fragment.

Typically the binding compounds of the invention are specific for the PfRH5 fragment of the invention, in that they do not binding to full-length PfRH5, or to fragments of PfRH5 comprising the flexible N-terminal region, or that the binding site for the binding compound is not contained (fully or in part) within the flexible N-terminal region of PfRH5.

Therapeutic Indications

The present invention also provides a method of stimulating or inducing an immune response in a subject comprising administering to the subject a PfRH5 fragment of the invention, or vector of the invention, or a binding compound of the invention (as described above).

Thus, in one embodiment, the method of stimulating or inducing an immune response in a subject comprises administering a PfRH5 fragment of the invention, or a vector of the invention, or a binding compound of the invention (as described above) to a subject.

In the context of the therapeutic uses and methods, a "subject" is any animal subject that would benefit from stimulation or induction of an immune response against a *Plasmodium* parasite. Typical animal subjects are mammals, such as primates, for example, humans.

Thus, the present invention provides a method for treating or preventing malaria.

The present invention also provides a PfRH5 fragment of the invention for use in prevention or treatment of malaria. Said fragment of PfRH5 may be in the form of a recombinant protein, a protein particle, a virus-like particle, a fusion protein, or a combination thereof as described herein.

The present invention further provides a PfRH5 fragment of the invention, and one or more further antigens selected from the group consisting of PfEBA175, PfRH1, PfRH2a, PfRH2b, PfRH4, or PfAARP, or a fragment thereof; for use in prevention or treatment of malaria. In a preferred embodiment, the present invention provides a PfRH5 fragment of the invention, and a PfAARP antigen or a fragment thereof; for use in prevention or treatment of malaria.

The present invention provides the vectors as described herein for use in the prevention or treatment of malaria.

The present invention further provides the binding compounds as described herein for use in the prevention or treatment of malaria.

The present invention provides the use of the PfRH5 fragment of the invention, vector, or binding compound of the invention (as described above) for use either alone or in combination in the prevention or treatment of malaria.

Additionally, the present invention provides the use of the PfRH5 fragment of the invention, vector, or binding compound of the invention (as described above), in the manufacture of a medicament for the prevention or treatment of malaria.

In one embodiment, the method for treating or preventing malaria comprises administering a therapeutically effective amount of a PfRH5 fragment of the invention, or binding compound, or a vector, of the invention (as described above), either alone or in combination, to a subject.

As used herein, the term "treatment" or "treating" embraces therapeutic or preventative/prophylactic measures, and includes post-infection therapy and amelioration of malaria.

As used herein, the term "preventing" includes preventing the initiation of malaria and/or reducing the severity or intensity of malaria. The term "preventing" includes inducing or providing protective immunity against malaria Immunity to malaria may be quantified using any appropriate technique, examples of which are known in the art.

A PfRH5 fragment of the invention, or binding compound, or a vector, of the invention (as described above) may be administered to a subject (typically a mammalian subject such as a human or other primate) already having malaria, a condition or symptoms associated with malaria, to treat or prevent malaria. For example, the subject may be suspected of having come in contact with *Plasmodium* parasite, or has had known contact with *Plasmodium* parasite, but is not yet showing symptoms of exposure.

When administered to a subject (e.g. a mammal such as a human or other primate) that already has malaria, or is showing symptoms associated with *Plasmodium* parasite infection, the PfRH5 fragment of the invention, or binding compound, or a vector, of the invention (as described above) can cure, delay, reduce the severity of, or ameliorate one or more symptoms, and/or prolong the survival of a subject beyond that expected in the absence of such treatment.

Alternatively, a PfRH5 fragment of the invention, or binding compound, or a vector, of the invention (as described above) may be administered to a subject (e.g. a mammal such as a human or other primate) who ultimately may be infected with *Plasmodium* parasite, in order to prevent, cure, delay, reduce the severity of, or ameliorate one or more symptoms of malaria, or in order to prolong the survival of a subject beyond that expected in the absence of such treatment, or to help prevent that subject from transmitting malaria.

The treatments and preventative therapies of the present invention are applicable to a variety of different subjects of different ages. In the context of humans, the therapies are applicable to children (e.g. infants, children under 5 years old, older children or teenagers) and adults. In the context of other animal subjects (e.g. mammals such as primates), the therapies are applicable to immature subjects and mature/adult subjects.

The present invention provides vaccine compositions comprising any of the PfRH5 fragments of the invention (described herein). Said vaccine compositions may further comprise one or more additional malarial antigens as described herein, and/or any further components as described herein.

The PfRH5 fragment of the invention, or a vector, of the invention (as described above) can be employed as vaccines. Accordingly, the present invention provides a vaccine composition comprising the PfRH5 fragment of the invention.

A vaccine composition of the invention comprising a PfRH5 fragment of the invention may further comprise one or more additional antigens selected from the group consisting of PfAMA1, PfEBA175, PfRH1, PfRH2a, PfRH2b, PfRH4, PfAARP, or a fragment thereof. For example, the present invention provides a vaccine composition comprising PfRH5 fragment of the invention in combination with one or more of the PfEBA175, PfRH1, PfRH2a, PfRH2b, PfRH4 or PfAARP antigens or a fragment thereof. In a preferred embodiment, the present invention provides a vaccine composition comprising a PfRH5 fragment of the invention in combination with a PfAARP antigen or a fragment thereof.

The present invention provides a vaccine composition comprising a vector that expresses a PfRH5 fragment of the invention. The vector of such a vaccine composition may further express one or more additional antigens selected from the group consisting of PfAMA1, PfEBA175, PfRH1, PfRH2a, PfRH2b, PfRH4, PfAARP, or a fragment thereof. Alternatively, the present invention provides a vaccine composition comprising a vector that expresses a PfRH5 fragment of the invention, together with a vector that expresses one or more further antigens selected from the group consisting of PfAMA1, PfEBA175, PfRH1, PfRH2a, PfRH2b, PfRH4 or PfAARP, or a fragment thereof. For example, the present invention provides a vaccine composition comprising a vector or vectors that express a PfRH5 fragment of the invention in combination with one or more of the PfEBA175, PfRH1, PfRH2a, PfRH2b, PfRH4 or PfAARP antigens, or a fragment thereof.

In a further aspect the present invention provides a vaccine composition comprising a PfRH5 fragment of the invention, optionally together with one or more additional antigens or fragments thereof (particularly PfAARP or a fragment thereof), where either or both the PfRH5 fragment and/or the one or more additional antigen or fragment thereof may be expressed as a virus like particle (VLP). Recombinant particulate vaccines are well known in the art. They may be, for example, either fusion proteins or proteins chemically conjugated to particles. Examples of fusion proteins are hepatitis B surface antigen fusions (e.g. as in the RTS,S malaria vaccine candidate), hepatitis B core antigen fusions, or Ty-virus like particles. Examples of chemical fusion particles are the Q-beta particles under development by the biotechnology company Cytos (Zurich, Switzerland).

The present invention further provides a vaccine composition comprising a PfRH5 fragment of the invention, optionally together with one or more additional antigen or a fragment thereof (particularly PfAARP or a fragment thereof), where either or both the PfRH5 fragment and/or the one or more additional antigen or fragment thereof may be expressed as a soluble recombinant protein. Recombinant protein-based vaccines are well known in the art. They may be, for example, monomeric soluble proteins or soluble fusion proteins. Such proteins are typically administered or formulated in a vaccine adjuvant. Examples of protein-based vaccines are diphtheria and tetanus toxoids, or soluble malaria protein antigens such as the AMA1 protein vaccine candidates developed for blood-stage malaria (Spring, M. D., et al., *PLoS ONE*, 2009. 4(4): p. e5254; incorporated herein by reference).

The PfRH5 fragment of the invention and one or more additional antigen or fragment thereof (preferably a PfAARP antigen or fragment thereof) may be combined to provide a single vaccine product (as described above) capable of inducing antibodies against both antigens, e.g. by mixing two separate recombinant protein vaccines, or by co-delivering the antigens using vaccine platforms such as particle-based protein vaccine delivery, or using a fusion of the two antigens; or by using a mixture of viral vectors expressing the individual antigens, or viral vectors co-expressing both antigens.

As used, herein, a "vaccine" is a formulation that, when administered to an animal subject such as a mammal (e.g. a human or other primate) stimulates a protective immune response against *Plasmodium* parasitic infection. The immune response may be a humoral and/or cell-mediated immune response. A vaccine of the invention can be used, for example, to protect a subject from the effects of *P. falciparum* infection (i.e. malaria).

The lack of polymorphism at the PfRH5 locus (five non-synonymous SNP across its entire length in circulating *P. falciparum* parasites) suggest either a lack of substantial immune pressure, or a high degree of functional constraint that prevents mutations from freely occurring. This property makes it highly likely that functional antibodies raised against a fragment of a single allele of PfRH5 according to the present invention will have broadly neutralising activity.

Thus, the PfRH5 fragments of the invention typically induce antibodies that provide a highly effective cross-strain GIA against the *Plasmodium* parasite. Thus, in one embodiment, the PfRH5 fragment of the invention provides protection (such as long term protection) against disease caused by *Plasmodium* parasites. Typically, the PfRH5 fragment of the invention provides an antibody response (e.g. a neutralising antibody response) to *Plasmodium* parasitic infection. The PfRH5 fragments, vaccine compositions, vectors, plasmids, antibodies and/or aptamers of the invention as described herein may be used to confer pre-erythrocytic or transmission-blocking protection against *Plasmodium* parasites.

Pharmaceutical Compositions and Formulations

The term "vaccine" is herein used interchangeably with the terms "therapeutic/prophylactic composition", "formulation" or "medicament".

The vaccine of the invention (as defined above) can be combined or administered in addition to a pharmaceutically acceptable carrier. Alternatively or in addition the vaccine of the invention can further be combined with one or more of a salt, excipient, diluent, adjuvant, immunoregulatory agent and/or antimicrobial compound.

Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of immunogenic compositions, therapeutic formulations, medicaments and prophylactic formulations (e.g. vaccines) is generally by conventional routes e.g. intravenous, subcutaneous, intraperitoneal, or mucosal routes. The administration may be by parenteral injection, for example, a subcutaneous, intradermal or intramuscular injection. Formulations comprising neutralizing antibodies may be particularly suited to administration intravenously, intramuscularly, intradermally, or subcutaneously.

Accordingly, immunogenic compositions, therapeutic formulations, medicaments and prophylactic formulations (e.g. vaccines) of the invention are typically prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active immunogenic ingredients (such as the PfRH5 fragments of the invention) are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds adjuvant (IFA), Saponin, a purified extract fraction of Saponin such as Quil A, a derivative of Saponin such as QS-21, lipid particles based on Saponin such as ISCOM/ISCOMATRIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, the MF59 formulation developed by Novartis, and the AS02, AS01, AS03 and AS04 adjuvant formulations developed by GSK Biologicals (Rixensart, Belgium).

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

The following Examples illustrate the invention.

EXAMPLES

Example 1—Solving the Crystal Structure of PfRH5

Structural studies of PfRH5 required design of a protein construct lacking flexible regions but still capable of binding basigin. Long-range predictions were carried out using Prediction Of Order and Disorder by machine LEarning (POODLE), which is described in Hirose et al. (2007) Bioinformatics 23:2046-2053. These predictions suggested disorder within regions 1-140 and 248-296 (FIG. 1).

In cultured parasite lines, PfRH5 is processed from ~60 kDa by removal of the N-terminus (equivalent to approximately residues 1-140) to generate a ~45 kDa protein. Guided by these observations, a PfRH5 fragment was designed which encompassed residues 140-526 but lacked residues 248-296 (RH5ΔNL). RH5ΔNL was produced in a stable *Drosophila* S2 cell system and was shown to bind basigin by surface plasmon resonance (SPR) with an affinity of 1.3 µM (FIG. 2C), comparable to 1.1 µM for full-length RH5 (FLRH5) binding to basigin.

In more detail, codon optimized, recombinant full length PfRh5 and RH5ΔNL (containing residues 140-248 and 296-526) from the 7G8 strain of *P. falciparum* were produced in *Drosophila* S2 cells from ExpreS²ions Biotechnologies with a C-terminal hexa-histidine tag and purified from the supernatant by Ni-NTA chromatography and ConA lectin-binding chromatography. Basigin (residues 22-205) was produced with an N-terminal hexa-histidine tag in Origami B (DE3) *E. coli* and purified by Ni-NTA chromatography, removal of the hexa-histidine tag using a TEV cleavage site, and gel filtration. Monoclonal antibodies 9AD4 and QA1 were expressed by hybridomas, and purified by protein G chromatography prior to mixture with RH5ΔNL. Fabs for use in the present experiments were produced from the corresponding monoclonal antibody by overnight papain digestion followed by protein A chromatography.

RH5ΔNL protein for crystallography was cleaved with endoproteinase GluC overnight, mixed with binding partner (BSG, 9AD4, or QA1), chemically methylated overnight and gel filtered. Crystals of RH5ΔNL:BSG, RH5ΔNL:9AD4, and RH5ΔNL:QA1 were obtained by the sitting-drop method. Data was collected at the Diamond synchrotron (Harwell, UK), and structures solved by molecular replacement followed by iterative refinement and building. SAXS data were collected for full-length Rh5 alone and in complex with BSG and Fabs 9AD4, QA1, and QAS, and data analysed using the ATSAS suite.

Data sets were collected to 2.3 Å (RH5ΔNL:9AD4) and 3.1 Å resolution (RH5ΔNL:basigin and RH5ΔNL:QA1). Structures were determined using molecular replacement, with a Fab fragment used as a search model for the determination of the RH5ΔNL:9AD4 structure, and the resulting RH5ΔNL model used a search model, together with structures of basigin and a Fab fragment, to determine structures of other complexes.

The structure of RH5 was shown to form a rigid, flat, 'kite-shaped' architecture not previously observed, with a pseudo-two-fold rotation symmetry (FIG. 2A). Each half is predominantly built from a three helical bundle, with the outermost helices showing significant kinks or breaks. The N-terminal half begins with a short, two-stranded β-sheet that crosses the long axis of the kite at the centre of the molecule. This is followed by a single, short helix and then by two long, kinked helices. Between the second and third helices is the loop truncated in this construct, which contains 58 residues in full-length RH5. The C-terminal half is simpler, consisting of three long helices that span the entire length of the domain and finishing with a flexible C-terminus. One disulphide bond stabilises the loop that links the two halves of the structure, while another links the second and third helices.

The RH5 structure is predominantly rigid, with the five copies found in the three different crystals aligning with an rmsd (root-mean-square-deviation, which is used to quanitfy the deviation of the observed molecular internal coordinates from the predicted values) of 0.9 Å over 95% of the residues (data not shown). The only differences were in the organisation of the C-terminus (residue 496-end) and the loop linking helices 4 and 5 (residues 396-406), which adopt a different position in the RH5:basigin structure due to crystal packing. A molecular envelope derived from small angle X-ray scattering (SAXS) analysis of full-length RH5 in solution exhibits a similar flat structure (FIG. 2C). This is elongated relative to RH5ΔNL, most likely due to the C-terminus, the flexible loop, and perhaps also part of the extended N-terminus.

As members of the *Plasmodium* Rh family show little sequence identity, a combination of sequence alignments and structure-based threading were used to determine whether other members contain the RH5 fold. For each protein analysed (*P. falciparum* Rh1, Rh2a, Rh2b, Rh3 and Rh4, *P. vivax* RBP-1 and RBP-2, *P. reichenowi* RH5, and *P. yoelii* Py01365), N-terminal RH5-like domains were identified with high confidence (data not shown). The sequence identity of this region to PfRH5 ranges from 14% (PvRBP1) to 70% (PrRH5), with no totally conserved residues. Residues showing similarity are located primarily in the interior of the domain, where they are likely to stabilise the fold (data not shown) and no conserved disulphide bonds are present. For PfRh4, the only other Rh protein whose erythrocyte receptor has been identified, the putative RH5 fold overlaps with a large region known to contain the complement receptor 1 (CR1) binding site and this RH5-like domain is an excellent candidate for the ligand binding module in other Rh family members.

Figure 3:
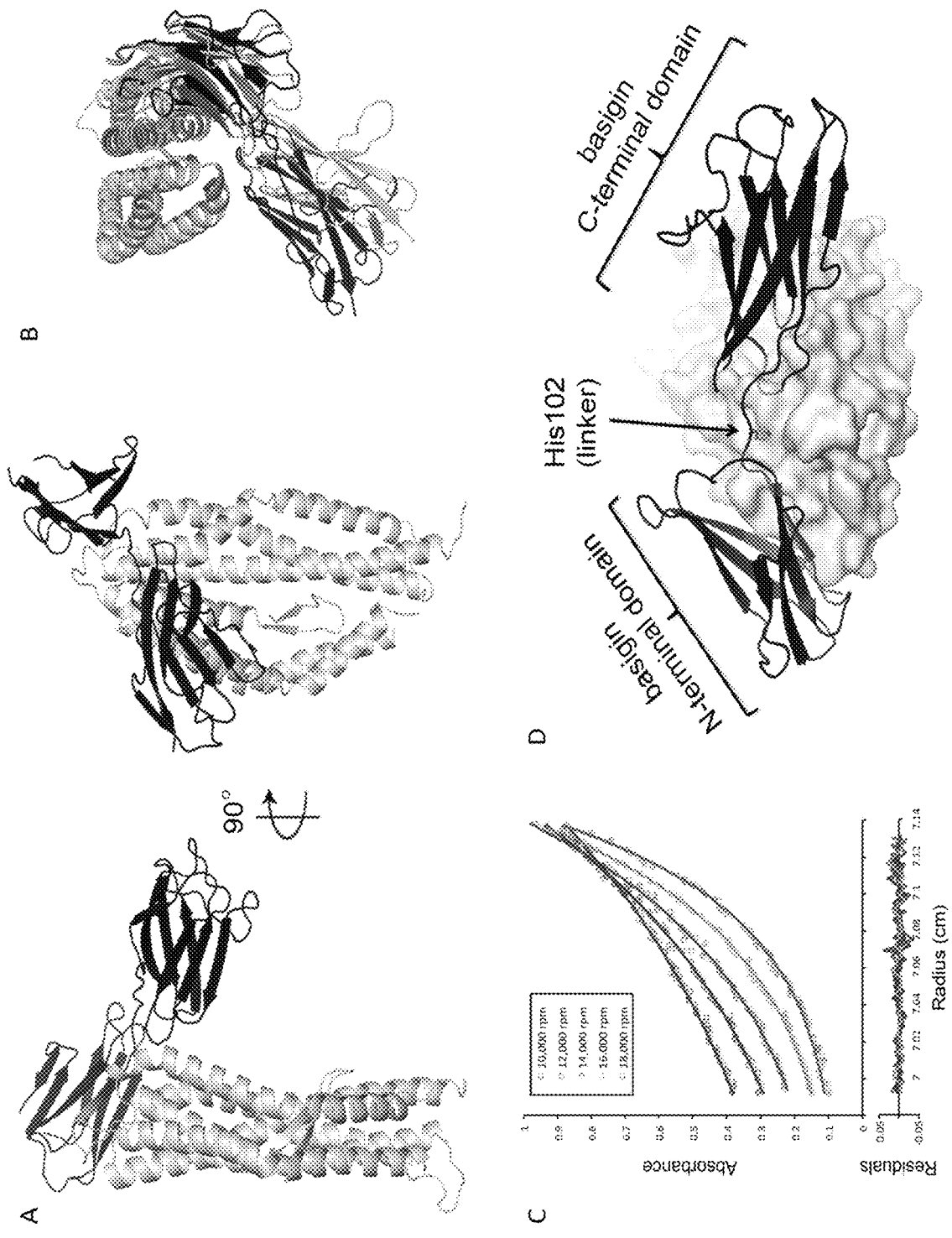
FIG. 3: The structure of the RH5:basigin complex. (A) The structure of RH5ΔNL bound to basigin. (B) A top view of the RH5ΔNL:basigin complex showing two conformations of basigin, corresponding to the two copies of basigin found in the crystal asymmetric unit, aligned based on the structure of RH5. (C) Equilibrium analytical ultracentrifugation analysis of the stoichiometry of the RH5:basigin interaction. A gel filtered complex of RH5ΔNL and basigin (at a concentration of 9 μM) was analysed at five different speeds and data were fit to an ideal monodisperse model giving a molecular weight of ~70 kDa for the complex, indicating a 1:1 complex. (D) Close-up of the RH5:basigin binding site. Residues where basigin contacts RH5 are located in the N-terminal domain, the linker (His102), and the C-terminal domain. In the other conformation of the basigin C-terminus (from the other copy of basigin in the asymmetric unit of the crystal), the loop contacts RH5.

The binding site for basigin has been demonstrated to lie at the tip of RH5, distant from the flexible loop and C-terminus, with both of the basigin domains and the linker making direct contacts with RH5 (FIG. 3 A, D). This is consistent with previous studies showing that both basigin domains are required for RH5 binding. The majority of the contact area (~1350 Å$^2$) occurs between strands A and G of the N-terminal domain of basigin and the loops at the tip of RH5. These contacts mostly involve hydrogen bonding to the backbone of basigin by the side chains of RH5 and the backbone of RH5 residues 447-449. Residues F350 and W447 of RH5 stabilise the interaction by packing into hydrophobic pockets on basigin. The relative lack of involvement of basigin side chains in the interaction will reduce the chance of basigin escape mutants that prevent RH5 binding.

Both the C-terminal domain of basigin and the side chain of H102 in the linker were also shown to make direct contacts with RH5. The three loops at the tip of the C-terminal domain (linking strands B and C, strands D and E and strands F and G) interact with the second and fourth helices of RH5. This is stabilised by hydrogen bonds and by a hydrophobic patch contributed by residues VPP from the BC loop. However, the C-terminal basigin domain was differently positioned in the two copies of the complex in the asymmetric unit of the crystal, with chain B interacting through the BC and DE loops (a contact area of ~570 Å) and chain D interacting through the BC and FG loops (~475 Å) (FIG. 3B). This leads to a maximum difference of 18 Å in the position of the C-terminus of basigin when the two complexes are aligned based on the structure of RH5. This flexibility is also reflected in an envelope of the RH5:basigin structure obtained through SAXS analysis of the complex in solution (data not shown). While RH5 and the N-terminal domain of basigin fit into this envelope, the C-terminal domain only fit partially, confirming that this domain interacts more flexibly with the helical side of the molecule.

Figure 4:
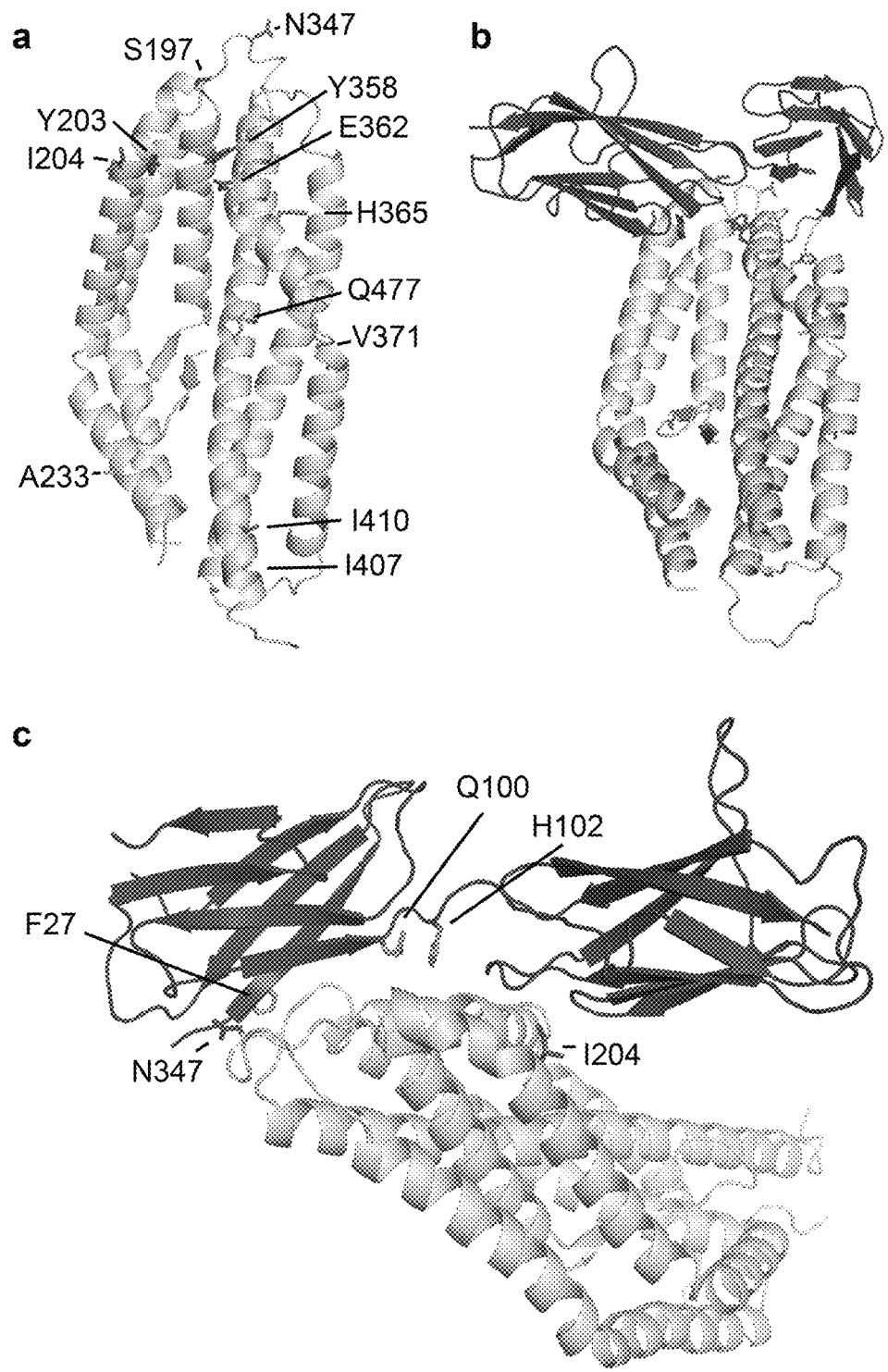
FIG. 4: Location of PfRH5 polymorphisms, and residues of PfRH5 and basigin implicated in host tropism. (A) and (B)—the locations of PfRH5 SNPs that are common (10% frequency or greater) or uncommon among 227 field isolates, as well as additional SNPs observed in lab strains are indicated. (B) Basigin is shown in addition to PfRH5. SNPs Y203, I204, N347, Y358, and E362 are localized in or near the PfRH5:basigin interface. Not visible in this orientation is lab strain polymorphism K429. (C) Highlighted are basigin residues F27, Q100, and H102, which affect the affinity for PfRH5 when mutated. Also shown are two SNPs of PfRH5, namely N347 and I204, found in the PfRH5:basigin binding interface and linked to the strain's ability to invade *Aotus* monkey erythrocytes.

RH5 is highly conserved, with just 12 non-synonymous SNPs found in 290 different isolates from across the world, and only 5 at frequencies of 10% or greater. These SNPs are distributed across the surface of the domain, with just one, Y203, forming part of the basigin binding site, but having no effect on the RH5:basigin affinity (FIG. 4). In sequenced laboratory strains there are eight different RH5 SNPs, all found in strains with increased ability to invade *Aotus* erythrocytes. A number of these residues (I204, N347, Y358 and E362) have been shown to be close to, or involved in the basigin binding site, and changes here are likely to affect the interaction of RH5 with basigin from different species. Basigin residues which, when mutated, affect RH5 affinity (F27, Q100 and H102) are also located at the interface.

The two RH5:basigin complexes in the asymmetric unit of the crystal pack together through a series of basigin-mediated contacts, including a ~911 Å interface between the two C-terminal domains of basigin, which brings the basigin C-termini into close proximity (data not shown). As basigin is linked to the erythrocyte membrane through a C-terminal helix, it is possible that this complex, containing two RH5 molecules and two basigin molecules, assembles during erythrocyte invasion, perhaps mediating a signalling event in either parasite or erythrocyte. However, in solution, at concentrations up to 24 µM no formation of a 2:2 complex was observed, either through SAXS (data not shown) or analytical ultracentrifugation (FIG. 2C).

X-ray crystallography and SAXS of RH5 in complex with Fab fragments of monoclonal antibodies known to block parasite growth were used to reveal regions of RH5 that can be targeted in vaccine development. Monoclonal antibody QA1 has been shown to directly block basigin binding in addition to preventing parasite growth. Both crystal structure and SAXS envelope demonstrated that QA1 binds to the tip of RH5, projecting along the RH5 long axis (FIGS. 5A and 6), with its hypervariable loops contacting RH5 through a loop (346-352) and the tips of helices 2 and 6 (198 and 452). This binding site partially overlaps that of the basigin N-terminal domain.

Figure 5:
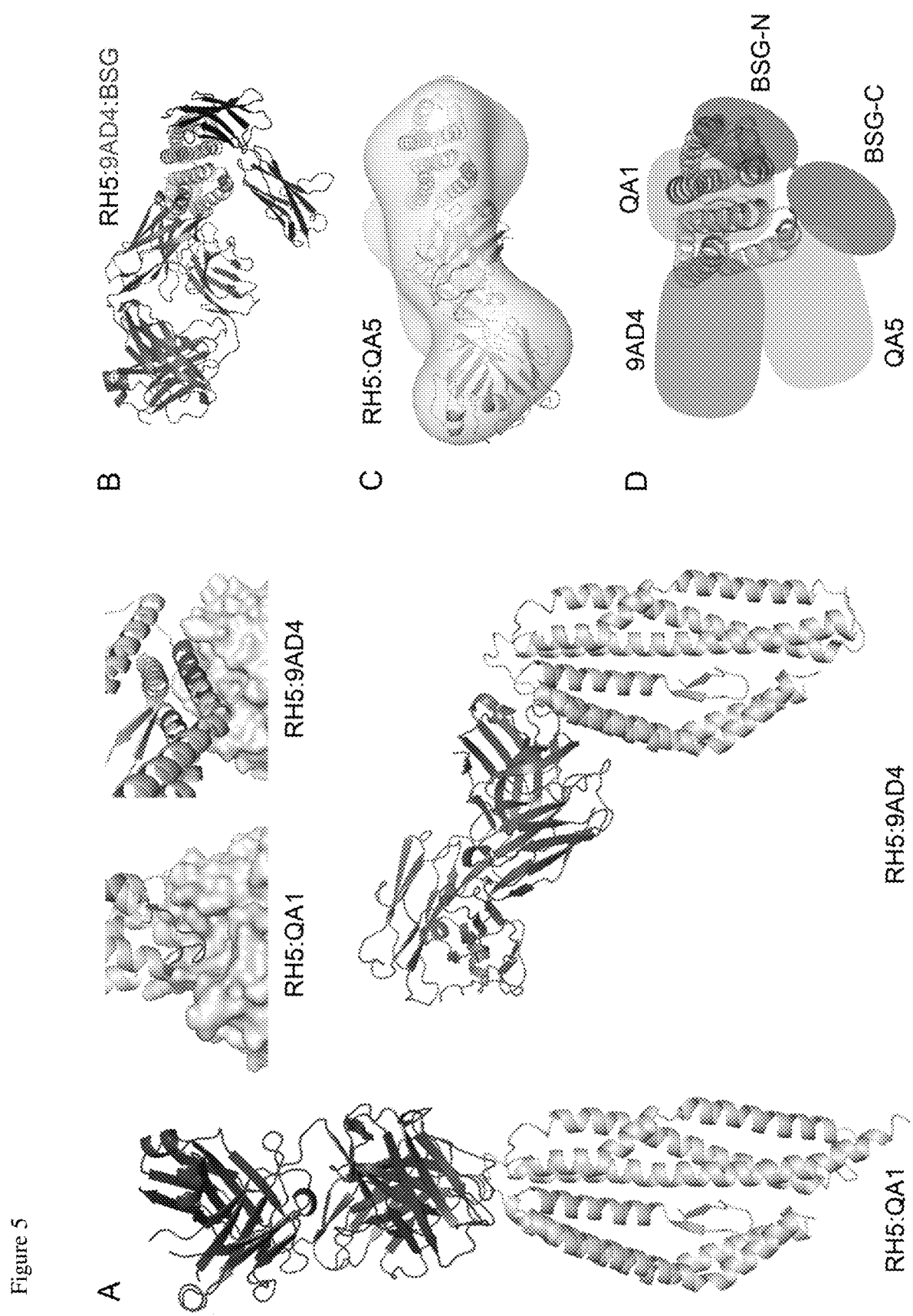
FIG. 5: Structural analysis of the binding of invasion-inhibitory Fab fragments to RH5. (A) Crystal structures of RH5ΔNL bound to inhibitory Fab fragments QA1 (left) and 9AD4 (right). Close-up views of the RH5 epitopes are shown, with the Fab fragment in each case shown as a grey surface. (B) Top view of RH5:9AD4 crystal structure with superimposed basigin, which was aligned based on the structure of RH5. (C) Top view of a model of the RH5:QAS interaction, docked into a molecular envelope derived from SAXS. (D) A schematic diagram showing the binding sites for basigin, QA1, 9AD4 and QAS, on the structure of RH5, showing QA1 and QAS to overlap with the basigin binding site on RH5.
Figure 6:
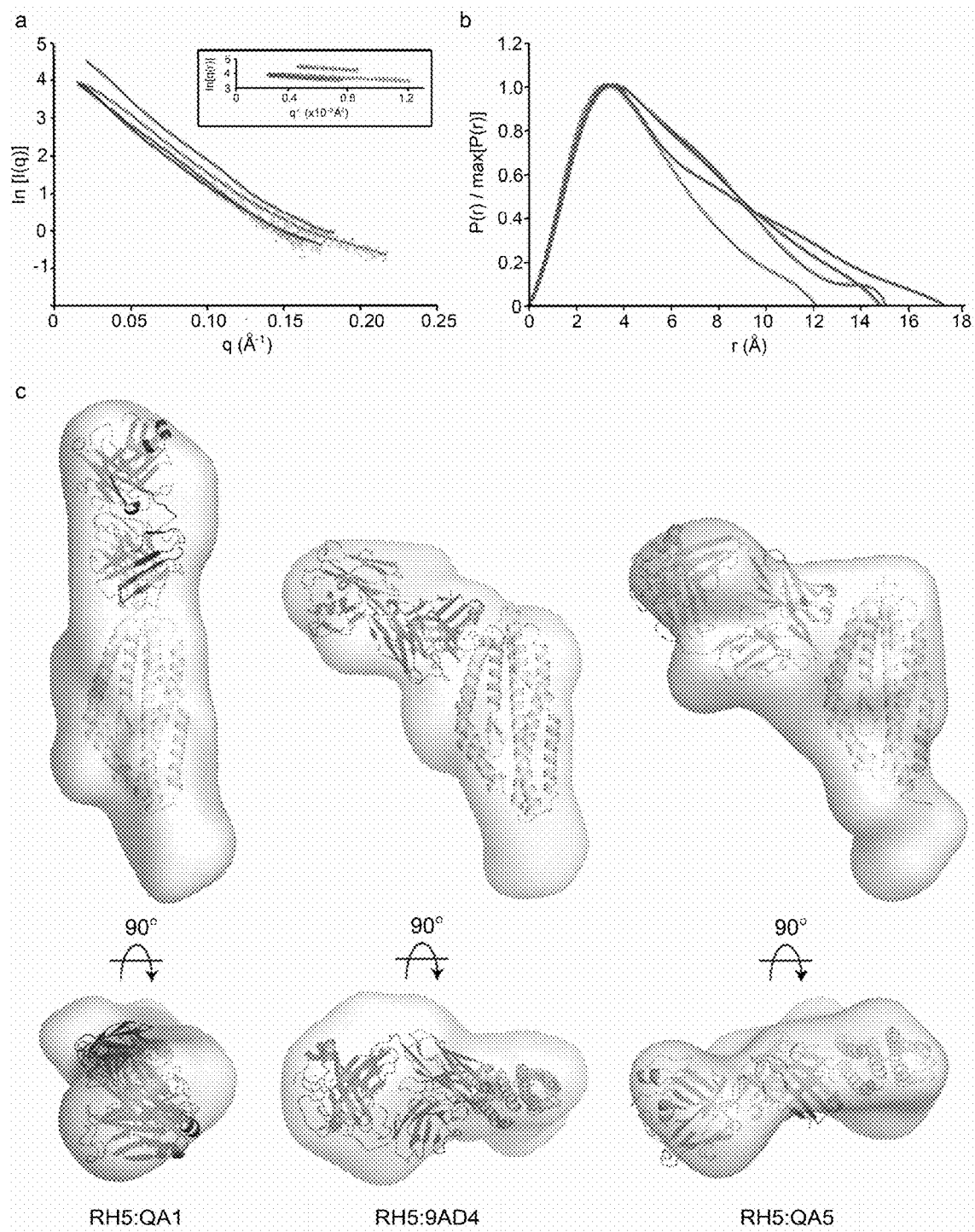
FIG. 6: SAXS of PfRH5 in complex with growth-inhibitory Fab fragments. (A) The theoretical scattering calculated from the average of 20 ab initio reconstructions (continuous lines) plotted with the experimental scattering intensity curves (black diamonds). The data are presented as the natural logarithm of the intensity. The Guiner plots are displayed in the inset. (B) The distance distribution function, P(r), with colours as in (A). (C) The crystal structures of PfRH5ΔNL:QA1(left) and PfRH5ΔNL:9AD4 (middle) were docked into the corresponding full-length PfRH5:Fab envelopes. PfRH5ΔNL and a Fab fragment were docked into the PfRH5:QA5 SAXS envelope to generate a model of the PfRH5:QA5 structure (right).

In contrast, another crystal structure, supported by SAXS data, showed that monoclonal antibody 9AD4 interacts with RH5 helices 2 (residues 209-213) and 3 (residues 331-341), binding close to the tip of the domain on its lateral edge (FIGS. 5A and 6). Superposition of the RH5:basigin structure onto that of RH5:9AD4 reveals that, although the C-terminal domain of basigin also interacts with helix 2, the 9AD4 binding site does not overlap with that of basigin (FIG. 5B). Consistent with these findings, 9AD4 does not impede basigin binding in a protein-protein interaction experiment. Nevertheless, 9AD4 is highly inhibitory of parasite growth. It is most likely that the close proximity of the 9AD4 binding site to that of basigin leads to a steric block in vivo that prevents binding when RH5 is immobilized on the parasite surface and basigin is tethered on the erythrocyte membrane.

A third antibody, QA5, known to block both basigin binding and parasite growth, was also studied by SAXS. Previous studies showed QA5 to interact with a linear peptide containing residues 201-213 from helix 2. This is compatible with the SAXS-derived molecular envelope, allowing generation of a model of the RH5:QA5 structure (FIG. 5C). This suggested that QA5 binds in between 9AD4 and the C-terminal domain of basigin, and overlaps with the binding sites of both, consistent with the ability of QA5 to compete with both basigin and 9AD4 binding.

Therefore, invasion-inhibitory antibodies can block the binding of the N-terminal domain (QA1) or the C-terminal domain (QA5) of basigin, or can bind nearby without directly overlapping the basigin binding site (9AD4; FIG. 5D). These regions of RH5 should all be included in any immunogen to raise inhibitory antibody responses to block basigin binding and parasite invasion.

In conclusion, the present experiments demonstrate that RH5 adopts a novel architecture, formed, as in many families of parasite surface proteins, from a robust a-helical scaffold. This allows maintenance of the overall fold, through retention of residues required for close packing of the helices, while allowing significant surface sequence variation. This fold is also found at the N-terminus of other members of the Rh protein family, where it is likely to act as a ligand-binding module.

Furthermore, the present data reveal for the first time that basigin binds at the tip of the RH5 domain, and reveal that monoclonal antibodies that block parasite growth bind at or close to this site Immunogens containing these regions of RH5 will be important components of a vaccine to prevent *Plasmodium falciparum* erythrocyte invasion, thereby crippling the parasite responsible for the deadliest form of human malaria.

Example 2—Functional In Vitro Growth Inhibitory Activity (GIA) of IgG Purified from the Serum of Rabbits Immunised with Full-Length PfRH5 Protein, Sv2 Protein (PfRH5ΔN) or Sv3 (PfRH5ΔNL)

Rabbits were immunised with full length RH5 (RH5), RH5 lacking the flexible N-terminal region of amino acid residues 1 to 139 of SEQ ID NO: 2 (RH5ΔN—SEQ ID NO: 4) or RH5 lacking the flexible N-terminal region of amino acid residues 1 to 139 of SEQ ID NO: 2 and the flexible central linker of amino acid residues 248 to 296 of SEQ ID NO: 2 (RH5ΔNL—SEQ ID NO: 8). Rabbit immunisations were carried out by Biogenes (Germany). Female ZiKa rabbits (n=4) were immunised intramuscularly (i.m.) with 20 µg protein on day 0, formulated in complete Freund's adjuvant, followed by two booster immunisations i.m. on days 28 and 56 with the same dose of protein formulated in incomplete Freund's adjuvant. Control rabbits received the same immunisation schedule with 50 µg ovalbumin protein. Serum was collected two weeks after the final immunisation and shipped frozen.

Total IgG was purified from rabbit sera using protein G columns (Pierce). The *P. falciparum* 3D7 and 7G8 lines were maintained in continuous culture using fresh $O^+$ erythrocytes at 2% haematocrit and synchronised by two incubations in 5% sorbitol 6-8 h apart. Synchronised trophozoites were adjusted to 0.3% parasitaemia and then incubated for 42 h with the various IgG concentrations (tested in triplicate)

Final parasitaemia was determined by biochemical determination of parasite lactate dehydrogenase. Percentage growth inhibition is expressed relative to wells containing IgG from control immunised rabbits. The mean of the three replicate wells was taken to obtain the final data for each individual rabbit at each tested IgG concentration. Experiments were performed twice against each strain of parasite with very similar results.

The assay of GIA was performed using the method of the MVI/NIH reference laboratory (as set out in K. Miura et al., Clinical and Vaccine Immunology 16, 963 (2009)). Total IgG was purified using Protein G (Pierce).

Results were calculated relative to growth in the presence of 10 mg/mL IgG from a rabbit immunized with non-malaria control vaccines.

Figure 7:
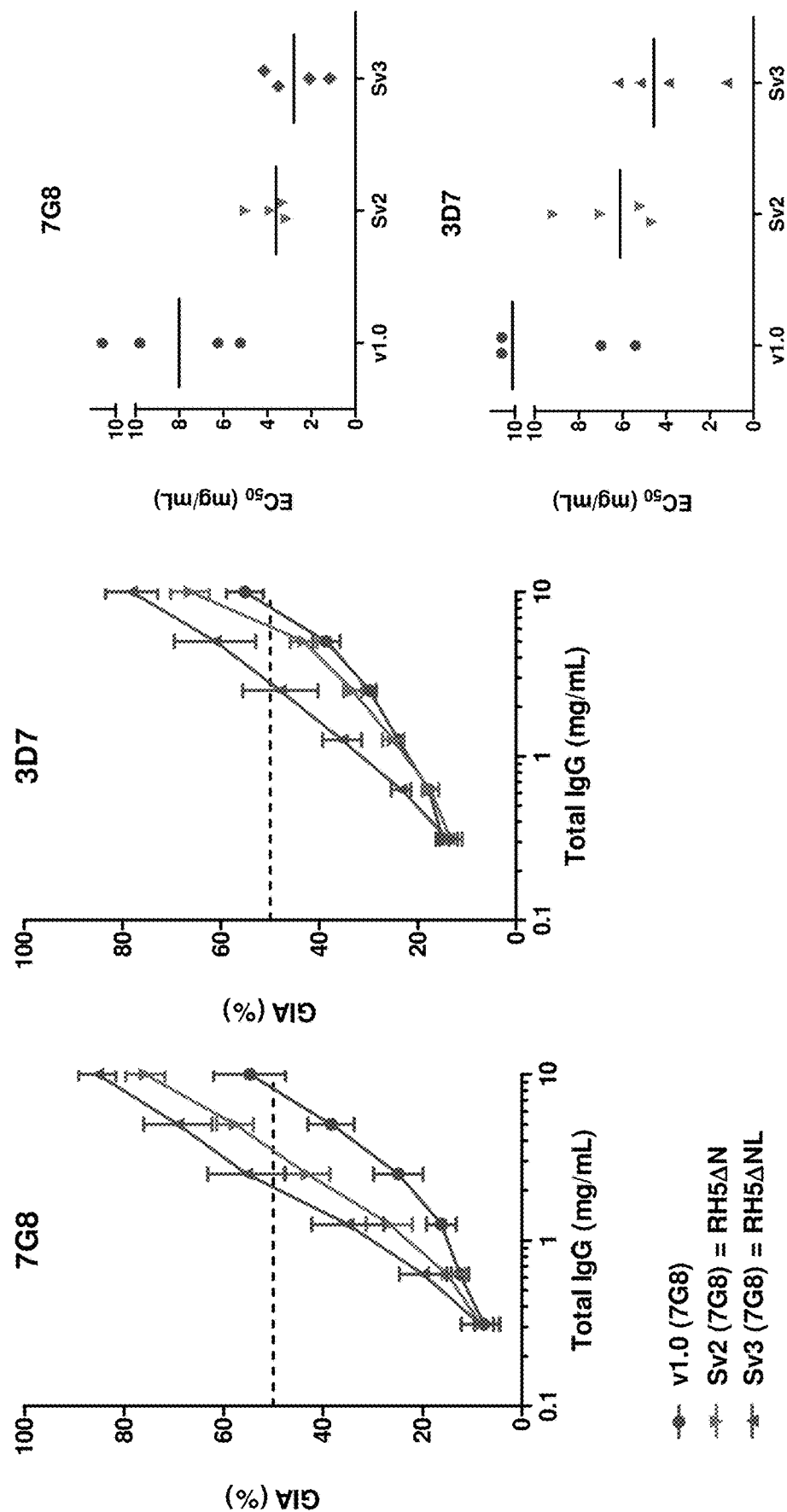
FIG. 7: Functional in vitro GIA of IgG purified from the serum of rabbits immunised with full-length PfRH5 protein, Sv2 protein (PfRH5ΔN) or Sv3 (PfRH5ΔNL) based on the 7G8 sequence. (left-hand panels) Rabbits were immunised as described and serum harvested on day 70 (two weeks post-final boost). IgG was purified and used to assess functional GIA in vitro against 3D7 clone and 7G8 strain parasites. Graphs show dilution of total IgG used in the assay against % GIA. Mean±sem is shown. (right-hand panels) $EC_{50}$s in terms of total IgG are shown for each individual rabbit. Note if the $EC_{50}$ was >10 mg/mL then this has not been extrapolated, and is plotted at 15 mg/ml.

It was found that IgG induced by RH5ΔN and RH5ΔNL potently inhibited parasite growth of both the 7G8 and 3D7 parasite strains (FIG. 7 left panels, show dilution of total IgG used against % GIA. Mean±sem shown). For both 7G8 and 3D7, RH5ΔN had a greater inhibitory effect on parasite growth than full length RH5, and RH5ΔNL had a greater effect than RH5ΔN (RH5<RH5ΔN<RH5ΔNL).

$EC_{50}$ values were estimated for the GIA effect of anti-PfRH5FL, anti-PfRH5ΔNL and anti-PfRH5ΔNL IgG against the 3D7 and 7G8 parasite strains. FIG. 7 right panels, gives the $EC_{50}$ values in terms of total IgG for each individual rabbit. Any $EC_{50}$ values >10 mg/mL have not been extrapolated, and are instead plotted at 15 mg/ml.

The results show that the RH5ΔNL (PfRH5ΔNL) vaccine induces the highest levels of functional GIA (lowest $EC_{50}$s) against both homologous (7G8) and heterologous (3D7) parasites. RH5ΔN (PfRH5ΔN) is intermediate, and full-length PfRH5 induces the lowest levels of functional GIA (highest $EC_{50}$s).

Example 3—Serum IgG ELISA Titres for Rabbits Immunised with Full-Length PfRH5 Protein, PfRH5ΔN or PfRH5ΔNL Rabbits were immunised, serum harvested on day 70 (two weeks post-final boost) and polyclonal antibodies against full length RH5, RH5ΔN and RH5ΔNL based on the 7G8 sequence were generated as described above.

Figure 8:
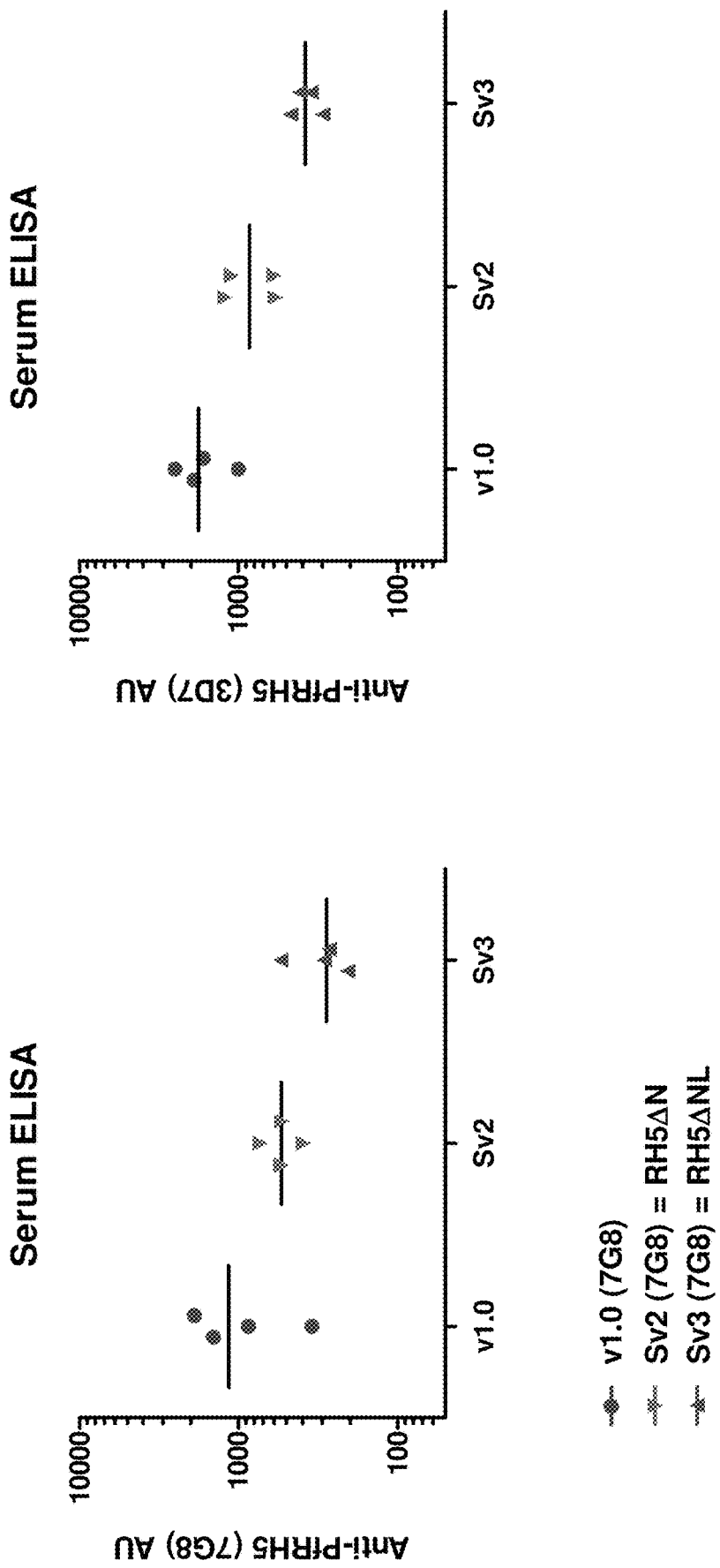
FIG. 8: Serum IgG ELISA titres for rabbits immunised with full-length PfRH5 protein, Sv2 protein (PfRH5ΔN) or Sv3 (PfRH5ΔNL) based on the 7G8 sequence.

ELISAs were performed against 3D7 and 7G8 PfRH5 recombinant protein to give the total antibody response in arbitrary antibody units (AU) as below (FIG. 8).

For PfRH5 ELISAs, PfRH5 protein was produced in Drosophila S2 cells and purified from supernatant. Maxisorp plates (Nunc-Immuno) were coated overnight with protein diluted in PBS. The next day plates were washed 6× in PBS containing 0.05% Tween 20 (PBS/T) and blocked for 1 h with Casein block solution (Pierce, UK). Plates were washed again, and then a standard serum sample, test sera, internal control and blank samples all diluted in Casein block solution were added to each plate for 2 h according to published methodology (Miura et al., Vaccine (2008), 26(2): 193-200; Sheehy et al., Mol. Ther. (2011), 19(12):2269-2276). The standard was serially diluted on every plate to make a standard curve. Test sera were diluted and tested in duplicate wells. Plates were washed again, followed by addition for 1 h of alkaline phosphatase-conjugated anti-rabbit IgG (whole molecule) (Sigma) diluted 1:5000 in Casein block solution. Plates were washed again and bound antibodies were detected by adding p-nitrophenylphosphate substrate (Sigma) diluted in diethanolamine buffer (Fisher Scientific, UK). Optical density was read at 405 nm (OD405) using an ELx800 microplate reader (BioTek, UK).

The ELISA antibody unit (AU) value of the standard was assigned as the reciprocal of the dilution giving an $OD_{405}$ of 1.0 in the standardized assay. The $OD_{405}$ of individual test samples was converted into AU by using the standard curve and GenS ELISA software v1.10 (BioTek, UK). If the $OD_{405}$ of test plasma was too high to read off the linear part of the curve, the assays were repeated, testing sera at a higher dilution.

The same pattern of antibody levels across full length RH5, RH5ΔN and RH5ΔNL was observed for both homologous (7G8) and heterologous (3D7) RH5 protein.

Example 4—GIA $EC_{50}$s Expressed in Terms of Anti-PfRH5 (7G8) ELISA Antibody Units (AU)

The purified IgG used in the GIA assays (Example 2, FIG. 7A) were assessed by ELISA using 7G8 PfRH5 recombinant protein to give the number of AU per mg/mL purified IgG.

Figure 9:
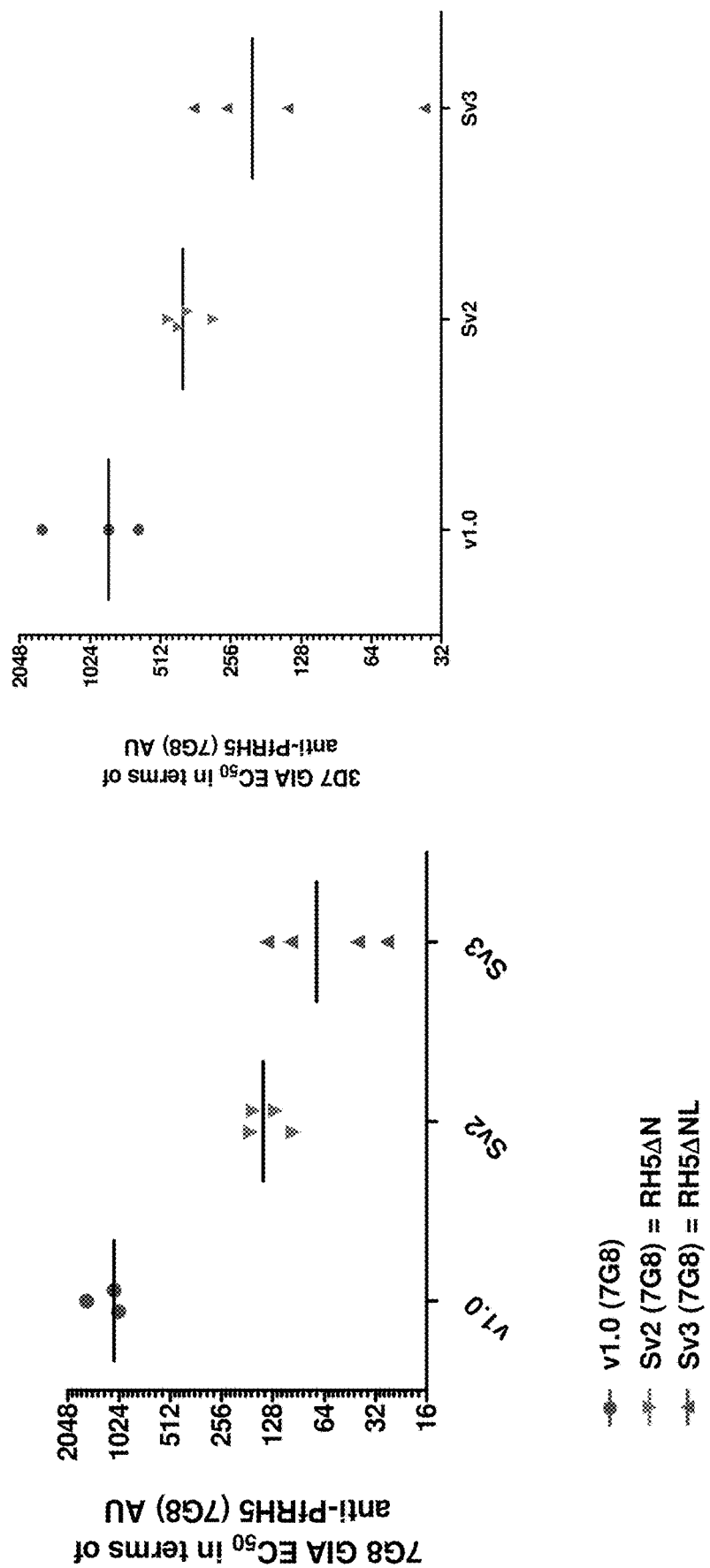
FIG. 9: GIA $EC_{50}$s expressed in terms of anti-PfRH5 (7G8) ELISA antibody units (AU).

The total IgG $EC_{50}$s reported against 7G8 strain and 3D7 clone parasites (FIG. 7B) are reported in terms of anti-PfRH5 (7G8) AU in FIG. 9.

The results show that RH5ΔNL (PfRH5ΔNL) protein induces an antibody response of the highest quality (>RH5ΔN (PfRH5ΔN)>full-length), achieving the same level of GIA (50%) with a lower amount of PfRH5-specific IgG.

Accordingly, the data presented herein demonstrate that rationally designed RH5 fragments which lack the flexible N-terminal region (RH5ΔN) produce a higher quality antibody response than the full length RH5 protein. Furthermore, RH5 fragments lacking the flexible N-terminal region and the flexible central linker (RH5ΔNL) produce an antibody response of even higher quality over the RH5 fragment lacking the N-terminal region.

The experimental data herein relates to RH5 fragments generated from the 7G8 strain (SEQ ID NO: 2). The present inventors have previously shown that full length RH5 from the 3D7 strain (SEQ ID NO: 1) elicits antibodies that are more effective against both homologous and heterologous parasite strains than full length RH5 from the 7G8 strain. Therefore, RH5 fragments derived from the 3D7 strain (for example RH5ΔN and/or RH5ΔNL from the 3D7 strain (SEQ ID NOs: 3 and 5 respectively) are likely to give rise to similarly improved antibody responses compared with corresponding RH5 fragments derived from the 7G8 strain. RH5 fragments derived from the 7G8, 3D7 and other strains are encompassed by the present invention.

Example 5—In Vivo Use of PfRH5 Fragment Vaccines in Primates

Vaccine

The vaccines used are unadjuvanted replication-deficient viral vectors for RH5ΔN (PfRH5ΔN) or RH5ΔNL (PfRH5ΔNL), with adenoviruses used for priming (likely serotype AdHu5, ChAd63, ChAdOX1 or ChAdOX2), and poxviruses used for boosting (Modified Vaccinia Ankara, MVA).

Viral vector vaccines are stored at −80° C. or on dry ice prior to use, then thawed and are stable at 4° C./on ice for at least 2 hours. Vaccines are prepared for administration by dilution in PBS, which can be performed at an earlier date (followed by re-freezing) if necessary.

Doses to be used are calculated with reference to tolerability of vectored vaccines in humans, and doses used in previous rabbit studies with this antigen. The vaccines express fragments of the blood-stage P. falciparum antigen RH5. It has previously been demonstrated that vaccines expressing full length RH5 are immunogenic in mice and rabbits. The antibodies induced are highly effective in GIA.

Preparation of Animals

*Aotus nancymaae* can be sourced from San Marcos University captive breeding programme and housed in AAALAC-accredited facilities at NAMRU-6.

Animals can be used which have previously been used in other studies, provided they are malaria-naive and have intact spleens. Possible confounding differences between animals (e.g. age, weight, type of previous use) could be addressed by stratified randomisation of animals to study groups.

Provisional group structure is as follows:

|  | Group number | Vaccine antigen | Number |
|---|---|---|---|
| VACCINE STUDY | 1 | AMA1 +/− MSP1 | 8 |
|  | 2 | PfRH5FL viral vectors | 8 |
|  | 3 | RH5ΔN viral vectors | 8 |
|  | 4 | RH5ΔNL viral vectors | 8 |
|  | 5 | Empty vectors (no malaria antigen; negative control) | 8 |
| THERAPY STUDY | 6 | PfRH5FL monoclonal antibody | 5 |
|  | 7 | RH5ΔN monoclonal antibody | 5 |
|  | 8 | RH5ΔNL monoclonal antibody | 5 |
|  | 9 | RH5ΔN aptamer | 5 |
|  | 10 | RH5ΔNL aptamer | 5 |
|  | 11 | Untreated infection controls | 5 |
|  | N/A | N/A - challenge donor | 1 |
|  |  | Total | 71 |

Precise size and number of groups is determined with statistical advice, after review of the variability in outcomes in non-vaccinated control *Aotus* in previous *P. falciparum* challenge trials.

Administration of Vaccine

An 8 week prime-boost interval gives reliable immunogenicity in mouse, rabbit, macaque and humans with these and related vectors.

*P. falciparum* Challenge

Challenge is performed 2 weeks post-boost, at which time antibody responses were at or near maximum in a macaque study of related vectors (Draper et al., J. Immunol. (2010), 185(12):7583-7595).

Frozen vials of FVO parasites are available at NAMRU-6. Optimal dose of parasites to be used for challenge is determined by balancing improved reliability of outcome in negative control animals if higher dose used, versus possible improved sensitivity of efficacy detection with prolonged period of parasitaemia if a lower dose is used.

10,000 ring-stage parasites appear to be commonly used, obtained by dilution of blood of a donor monkey with microscopically-patent parasitaemia (Dutta et al., Plos One (2009), 4(12):e8138).

The schedule is as follows:

Day −1: -Pre-immune bleed (c. 2 ml blood, for serum+/−PBMCs). This can be performed immediately prior to vaccination on day 0 if preferable for convenience of animal handling.

Day 0: Prime vaccination (adenovirus vectors in PBS, c. 200 ul intramuscular)

Day 14: Post-prime immuno-monitoring bleed (c. 2 ml blood, for serum+/−PBMCs)

Day 49: Optional immuno-monitoring bleed (0.5 ml blood, for serum)

Day 55: Pre-boost immuno-monitoring bleed (c. 2 ml blood, for serum+/−PBMCs). This can be performed immediately prior to boost vaccination on day 56 if preferable for convenience or animal handling.

Day 56: Boost vaccination (MVA vectors in PBS, 200-400 ul intramuscular)

Day 69=Day C−1: Post-boost immuno-monitoring bleed (c. 2 ml blood, for serum+/−PBMCs). This can be performed immediately prior to challenge on day 70 if preferable for convenience or animal handling.

Day 70=Day C+0: Challenge with FVO parasites. Dose and protocol TBC as above.

Daily from day C+3 until treatment endpoint: Clinical symptom scoring. Bleeds for parasitaemia monitoring by microscopy+/−QPCR; measurement of hematocrit and/or hemoglobin concentration. See below for treatment endpoints.

Day of treatment: Post-challenge immuno-monitoring bleed (0.5 ml blood, for serum)

~Day 91=Day C+21: End of challenge phase of study.

Re-challenge: a second challenge of the animals is envisaged.

Immunological and Parasitological Assays

Antigen-specific antibody titers are quantified by ELISA at multiple timepoints.

Additional assays include:
  GIA (pre-challenge timepoint; 70% GIA at 1:10 serum dilution has been proposed as a correlate of vaccine-induced protection in *Aotus*);
  IFA (pre-challenge timepoint);
  ADRB;
  QPCR monitoring of parasite density
  ELISPOT or ICS quantification of antigen-specific T cells.

Endpoints

Different possible endpoints have been proposed for *Aotus-P. falciparum* challenges. Cumulative parasitemia calculated by summing daily parasitemia from the day of challenge until the day the first animal in the study is treated for any reason has been used in some recent studies and, by virtue of being a continuous variable, may have statistical advantages (Lyon et al., PloS One (2008), 3(7):e2830).

Humane drug treatment endpoints are employed which may include the following:
  clinical symptoms exceeding a pre-defined score,
  a threshold level of uncontrolled parasitaemia e.g. 200,000 p/µl or 5%,
  a threshold level of anaemia,
  reaching a pre-specified day post-challenge, e.g. C+21.

Example 6—Use of PfRH5 Fragment Vaccine in Humans

Construction of Vaccine

Viral-vector expressed PfRH5 fragment (PfRH5ΔN or PfRH5ΔNL) is generated from MVA, or AdHu5 or ChAd63 or ChAdOX1 or ChAdOX2. The process is initiated using a plaque-purified recombinant and GMP-certified HEK293 cells (available at the Jenner Institute Clinical Biomanufacturing Facility). A single batch of $>1.2 \times 10^{13}$ viral particles (vp) is generated. Release assays are according to the European Pharmacopoeia. Absence of replication competent virus is demonstrated. The MVA-PfRH5ΔN or MVA-PfRH5ΔNL antigen is used as a boosting agent and is manufactured in chicken embryo fibroblasts (CEFs). The seed stock virus is supplied for production of the master seed virus/working seed virus (MSV/WSV). A clinical lot is then produced from the WSV. Vaccine toxicology studies are undertaken Administration of Vaccine Volunteers receive various dose schedules of viral-vector expressed PfRH5ΔN or PfRH5ΔNL in groups. The sample size is sufficient to monitor routine and/or unexpected local and systemic AEs, whilst providing a thorough analysis of vaccine-induced cellular and humoral immunogenicity. Vaccine safety and immunogenicity is monitored in detail and analysed between dosing/regime groups using appropriate non-parametric statistics for small group sizes.

Vaccine-induced antigen-specific IgG function is assessed by in vitro assays of growth inhibitory activity (GIA) against *P. falciparum* strain 3D7, FVO, 7G8 and/or Dd2 parasites.

All vaccinations are administered intramuscularly in the deltoid muscle of the upper arm. This route of administration has been shown to be safe for other ChAd63 vaccines and to significantly reduce local AEs in comparison to intradermal vaccination.

Volunteers in Group 1 receive a dose of $5\times10^9$ vp of ChAd63 PfRH5ΔN or PfRH5ΔNL (Group 1) and volunteers in Group 2 receive the full dose of $5\times10^{10}$ vp of ChAd63 PfRH5ΔN or PfRH5ΔNL (Group 2). This two-step dose escalation for the ChAd63 vaccine vector has been applied to ChAd63-PfMSP1 and ChAd63-PfAMA1 in clinical trials without any safety issues arising.

Within Group 2 ($5\times10^{10}$ vp ChAd63-PfRH5ΔN or ChAd63-PfRH5ΔNL), two sub-groups of volunteers (2B and 2C) are boosted after 8 weeks with an escalating dose of MVA-PfRH5ΔN or MVA-PfRH5ΔNL. Group 2A represents non-boosted controls.

The doses of MVA-PfRH5ΔN or MVA-PfRH5ΔNL are $1\times10^8$ pfu for Group 2B, and $2\times10^8$ pfu for Group 2C. A dose of $1-2\times10^8$ pfu is the standard dose currently used in other studies of MVA vaccines encoding ME-TRAP, PfMSP1 or PfAMA1.

Assessment Following Administration of Antigen

Safety and tolerability of viral-vector expressed PfRH5ΔN or PfRH5ΔNL is assessed by comparing the frequency and severity of both local and systemic adverse events (AEs) between the dosing groups, including using diary cards for the first week. Details of AEs are collected at each clinic visit, along with a medical examination. Blood samples for haematology and biochemistry are taken at screening, and days 14, 28, 56, 63, 84 and 140.

Humoral and cellular immunogenicity of viral-vector expressed PfRH5ΔN or PfRH5ΔNL vaccines administered in the various dosing regimens is assessed.

Immunological blood samples are taken at screening and days 0, 1, 4, 7, 14, 28, 56, 57, 60, 63, 84, 112 and 140 with respect to ChAd63-PfRH5ΔN or ChAd63-PfRH5ΔNL vaccination on day 0 and MVA-PfRH5ΔN or MVA-PfRH5ΔNL vaccination on day 56.

PfRH5ΔN or PfRH5ΔNL-specific immunogenicity is assessed by a variety of immunological assays including total IgG, isotype and avidity ELISA, GIA, memory B cell and plasma cell (ASC) ELIspot, ex-vivo IFN-γ ELISPOT, multiparameter flow cytometry and more exploratory assays including host gene expression studies post-vaccination.

Sporozoite Challenge

Once adequate immunogenicity is observed—defined as >20% GIA activity in at least half the vaccinees—a further group of subjects is vaccinated with the most immunogenic regime identified.

These subjects are challenged (along with non-vaccinated controls) with a number (e.g. 5) of infectious mosquito bites. This procedure is now well established by the Imperial College (R Sinden)—Oxford—Walter Reed (J Murphy) team and over 250 individuals have been challenged in the last six years.

Control volunteers develop patent parasitaemia at, on average, 11 days post challenge and those who do not develop malaria by day 21 are considered fully protected. The subjects are monitored carefully for any evidence of immunopathology (although this is very unlikely at the low parasite densities that are reached prior to treatment).

A real-time PCR assay to quantify blood-stage infection is used twice a day during the key follow-up period from day 6.5 to 14.0 post challenge (and daily thereafter). This has proved valuable in monitoring rates of parasite growth in vaccinees, recently providing evidence of measurable but low level blood-stage efficacy with the PEV3a vaccine.

Assessment Following Sporozoite Challenge

As in the above assessment following administration of antigen, detailed immunomonitoring is undertaken and, in this case, correlates of GIA activity and/or immune responses with efficacy are searched for.

Fully protected volunteers are invited to undergo a re-challenge at six months after their final vaccination to determine the durability of protection.

Example 7—In Vivo Treatment of Malaria in Primates Using PfRH5ΔN or PfRH5ΔNL Binding Agents Construction of Binding Agents Construction of Bind PfRH5ΔN or PfRH5ΔNL-Binding Monoclonal Antibodies.

Murine monoclonal antibodies which specifically bind PfRH5ΔN or PfRH5ΔNL in an ELISA are isolated from hybridomas generated by fusing splenocytes from mice immunized with PfRH5ΔN or PfRH5ΔNL with myeloma cells. It is confirmed that these antibodies recognise native parasites in an indirect immunofluorescence assay, and inhibit parasite growth in GIA.

A panel of mAbs is generated which are capable of binding PfRH5ΔN or PfRH5ΔNL by ELISA. BALB/c mice are immunised with adenovirus and MVA-vectored PfRH5ΔN or PfRH5ΔNL vaccines at doses of $1\times10^8$ infectious units and $1\times10^7$ plaque forming units respectively, and with an 8 to 12 week prime-boost interval. Splenocytes are fused with Sp2 myeloma cells, according to previously published methods (Yokoyama et al. Curr. Protoc. Immunol. (2006) Chapter 2:Unit 2.5). Hybridoma supernatants are screened for binding to recombinant PfRH5ΔN or PfRH5ΔNL protein by ELISA, using previously published methods.

The ability of each of the mAbs to neutralize 3D7-strain parasites is tested in a GIA assay.

Previously published methods are used to minimize the immunogenicity of the monoclonal antibody in order to make it suitable for human use, such as replacement of the murine Fc region with a human Fc region of a chosen Ig class and subtype.

Construction of Bind PfRH5ΔN or PfRH5ΔNL-Binding Polyclonal Antibodies

Construction of polyclonal antibodies is carried out as in Example 2 above.

Construction of PfRH5-Binding Aptamers

An oligonucleotide aptamer which specifically bind PfRH5ΔN or PfRH5ΔNL is identified using known methods (as set out e.g. in D. H. J. Bunka, P. G. Stockley, Nature Reviews Microbiology 4, 588 (2006)). It is confirmed that this molecule recognizes native parasites in an indirect immunofluorescence assay, and inhibited parasite growth in GIA.

Previously published methods are used to optimize the pharmacokinetics (half-life and biodistribution) of the aptamer, to render it suitable for therapeutic use.

The aptamer is conjugated to a monoclonal antibody to modify its pharmacokinetics and/or recruit Fc-dependent immune functions.

Preparation of Animals

This is carried out as in Example 5 above.

*P. falciparum* Challenge

This is carried out as in Example 5 above, with the exception that malaria- and vaccine-naïve monkeys are infected with *P. falciparum* FVO parasites.

Treatment

At a pre-determined point at which all monkeys exhibit microscopically quantifiable parasitaemia, the therapeutic agents (monoclonal antibody or aptamer) are administered at high dose.

The dosage regime in the case of monoclonal antibody is in the region of 1 mg/ml blood volume. The dosage regime in the case of aptamers is the molar equivalent (around 7 μM)).

The outcome of infection is compared to infected but untreated control monkeys.

Immunological and Parasitological Assays

This is carried out as in Example 5 above.

Endpoints

These are considered as in Example 5 above.

Sequence Information

Full Length PfRH5 Amino Acid Sequence (3D7) Including Signal Sequence: SEQ ID NO: 1

```
  1 MIRIKKKLIL TIIYIHLFIL NRLSFENAIK KTKNQENNLT LLPIKSTEEE KDDIKNGKDI

61 KKEIDNDKEN IKTNNAKDHS TYIKSYLNTN VNDGLKYLFI PSHNSFIKKY SVFNQINDGM

121 LLNEKNDVKN NEDYKNVDYK NVNFLQYHFK ELSNYNIANS IDILQEKEGH LDFVIIPHYT

181 FLDYYKHLSY NSIYHKSSTY GKCIAVDAFI KKINETYDKV KSKCNDIKND LIATIKKLEH

241 PYDINNKNDD SYRYDISEEI DDKSEETDDE TEEVEDSIQD TDSNHTPSNK KKNDLMNRTF

301 KKMMDEYNTK KKKLIKCIKN HENDFNKICM DMKNYGTNLF EQLSCYNNNF CNTNGIRYHY

361 DEYIHKLILS VKSKNLNKDL SDMTNILQQS ELLLTNLNKK MGSYIYIDTI KFIHKEMKHI

421 FNRIEYHTKI INDKTKIIQD KIKLNIWRTF QKDELLKRIL DMSNEYSLFI TSDHLRQMLY

481 NTFYSKEKHL NNIFHHLIYV LQMKFNDVPI KMEYFQTYKK NKPLTQ
```

Signal sequence (amino acids 1 to 23) is in bold italics, flexible N-terminal (amino acids 1 to 139) and flexible loop (amino acids 248 to 296) regions are underlined.

Full Length PfRH5 Amino Acid Sequence (7G8) Including Signal Sequence: SEQ ID NO: 2

```
  1 MIRIKKKLIL TIIYIHLFIL NRLSFENAIK KTKNQENNLT LLPIKSTEEE KDDIKNGKDI

61 KKEIDNDKEN IKTNNAKDHS TYIKSYLNTN VNDGLKYLFI PSHNSFIKKY SVFNQINDGM

121 LLNEKNDVKN NEDYKNVDYK NVNFLQYHFK ELSNYNIANS IDILQEKEGH LDFVIIPHYT

181 FLDYYKHLSY NSIYHKSSTY GKYIAVDAFI KKINETYDKV KSKCNDIKND LIATIKKLEH

241 PYDINNKNDD SYRYDISEEI DDKSEETDDE TEEVEDSIQD TDSNHTPSNK KKNDLMNRTF

301 KKMMDEYNTK KKKLIKCIKN HENDFNKICM DMKNYGTNLF EQLSCYNNNF CNTNGIRYHY

361 DEYIHKLILS VKSKNLNKDL SDMTNILQQS ELLLTNLNKK MGSYIYIDTI KFIHKEMKHI

421 FNRIEYHTKI INDKTKIIQD KIKLNIWRTF QKDELLKRIL DMSNEYSLFI TSDHLRQMLY

481 NTFYSKEKHL NNIFHHLIYV LQMKFNDVPI KMEYFQTYKK NKPLTQ
```

Signal sequence (amino acids 1 to 23) is in bold italics, flexible N-terminal (amino acids 1 to 139) and flexible loop (amino acids 248 to 296) regions are underlined.

PfRH5 Amino Acid Sequence (3D7) Excluding Signal Sequence and Flexible N-Terminal Region (Amino Acids 1 to 139): SEQ ID NO: 3

```
  1 KNVNFLQYHF KELSNYNIAN SIDILQEKEG HLDFVIIPHY TFLDYYKHLS YNSIYHKSST
 61 YGKCIAVDAF IKKINEAYDK VKSKCNDIKN DLIATIKKLE HPYDINNKND DSYRYDISEE
121 IDDKSEETDD ETEEVEDSIQ DTDSNHAPSN KKKNDLMNRA FKKMMDEYNT KKKKLIKCIK
181 NHENDFNKIC MDMKNYGTNL FEQLSCYNNN FCNTNGIRYH YDEYIHKLIL SVKSKNLNKD
241 LSDMTNILQQ SELLLTNLNK KMGSYIYIDT IKFIHKEMKH IFNRIEYHTK IINDKTKIIQ
301 DKIKLNIWRT FQKDELLKRI LDMSNEYSLF ITSDHLRQML YNTFYSKEKH LNNIFHHLIY
361 VLQMKFNDVP IKMEYFQTYK KNKPLTQ
```

Flexible loop (corresponding to amino acids 248 to 296 of full length PfRH5 of SEQ ID NO: 1) region is underlined.

PfRH5 Amino Acid Sequence (7G8) Excluding Signal Sequence and Flexible N-Terminal Region (Amino Acids 1 to 139): SEQ ID NO: 4

```
  1 KNVNFLQYHF KELSNYNIAN SIDILQEKEG HLDFVIIPHY TFLDYYKHLS YNSIYHKSST
 61 YGKYIAVDAF IKKINEAYDK VKSKCNDIKN DLIATIKKLE HPYDINNKND DSYRYDISEE
121 IDDKSEETDD ETEEVEDSIQ DTDSNHAPSN KKKNDLMNRA FKKMMDEYNT KKKKLIKCIK
181 NHENDFNKIC MDMKNYGTNL FEQLSCYNNN FCNTNGIRYH YDEYIHKLIL SVKSKNLNKD
241 LSDMTNILQQ SELLLTNLNK KMGSYIYIDT IKFIHKEMKH IFNRIEYHTK IINDKTKIIQ
301 DKIKLNIWRT FQKDELLKRI LDMSNEYSLF ITSDHLRQML YNTFYSKEKH LNNIFHHLIY
361 VLQMKFNDVP IKMEYFQTYK KNKPLTQ
```

Flexible loop (corresponding to amino acids 248 to 296 of full length PfRH5 of SEQ ID NO: 2) region is underlined.

PfRH5 Amino Acid Sequence (3D7) Excluding Signal Sequence and Flexible N-Terminal Region (Amino Acids 1 to 159): SEQ ID NO: 5

```
  1 SIDILQEKEG HLDFVIIPHY TFLDYYKHLS YNSIYHKSST YGKCIAVDAF IKKINEAYDK
 61 VKSKCNDIKN DLIATIKKLE HPYDINNKND DSYRYDISEE IDDKSEETDD ETEEVEDSIQ
121 DTDSNHAPSN KKKNDLMNRA FKKMMDEYNT KKKKLIKCIK NHENDFNKIC MDMKNYGTNL
181 FEQLSCYNNN FCNTNGIRYH YDEYIHKLIL SVKSKNLNKD LSDMTNILQQ SELLLTNLNK
241 KMGSYIYIDT IKFIHKEMKH IFNRIEYHTK IINDKTKIIQ DKIKLNIWRT FQKDELLKRI
301 LDMSNEYSLF ITSDHLRQML YNTFYSKEKH LNNIFHHLIY VLQMKFNDVP IKMEYFQTYK
361 KNKPLTQ
```

Flexible loop (corresponding to amino acids 248 to 296 of full length PfRH5 of SEQ ID NO: 1) region is underlined.

PfRH5 Amino Acid Sequence (7G8) Excluding Signal Sequence and Flexible N-Terminal Region (Amino Acids 1 to 159): SEQ ID NO: 6

```
  1 SIDILQEKEG HLDFVIIPHY TFLDYYKHLS YNSIYHKSST YGKYIAVDAF IKKINEAYDK
 61 VKSKCNDIKN DLIATIKKLE HPYDINNKND DSYRYDISEE IDDKSEETDD ETEEVEDSIQ
```

-continued

```
121 DTDSNHAPSN KKKNDLMNRA FKKMMDEYNT KKKKLIKCIK NHENDFNKIC MDMKNYGTNL

181 FEQLSCYNNN FCNTNGIRYH YDEYIHKLIL SVKSKNLNKD LSDMTNILQQ SELLLTNLNK

241 KMGSYIYIDT IKFIHKEMKH IFNRIEYHTK IINDKTKIIQ DKIKLNIWRT FQKDELLKRI

301 LDMSNEYSLF ITSDHLRQML YNTFYSKEKH LNNIFHHLIY VLQMKFNDVP IKMEYFQTYK

361 KNKPLTQ
```

Flexible loop (corresponding to amino acids 248 to 296 of full length PfRH5 of SEQ ID NO: 2) region is underlined.

PfRH5 Amino Acid Sequence (3D7) Excluding Signal Sequence, Flexible N-Terminal (Amino Acids 1 to 139) and Flexible Loop (Amino Acids 248 to 296) Regions: SEQ ID NO: 7

```
  1 KNVNFLQYHF KELSNYNIAN SIDILQEKEG HLDFVIIPHY TFLDYYKHLS YNSIYHKSST

61 YGKCIAVDAF IKKINEAYDK VKSKCNDIKN DLIATIKKLE HPYDINNKNR AFKKMMDEYN

121 TKKKKLIKCI KNHENDFNKI CMDMKNYGTN LFEQLSCYNN NFCNTNGIRY HYDEYIHKLI

181 LSVKSKNLNK DLSDMTNILQ QSELLLTNLN KKMGSYIYID TIKFIHKEMK HIFNRIEYHT

241 KIINDKTKII QDKIKLNIWR TFQKDELLKR ILDMSNEYSL FITSDHLRQM LYNTFYSKEK

301 HLNNIFHHLI YVLQMKFNDV PIKMEYFQTY KKNKPLTQ
```

PfRH5 Amino Acid Sequence (7G8) Excluding Signal Sequence, Flexible N-Terminal (Amino Acids 1 to 139) and Flexible Loop (Amino Acids 248 to 296) Regions: SEQ ID NO: 8

```
  1 KNVNFLQYHF KELSNYNIAN SIDILQEKEG HLDFVIIPHY TFLDYYKHLS YNSIYHKSST

61 YGKYIAVDAF IKKINEAYDK VKSKCNDIKN DLIATIKKLE HPYDINNKNR AFKKMMDEYN

121 TKKKKLIKCI KNHENDFNKI CMDMKNYGTN LFEQLSCYNN NFCNTNGIRY HYDEYIHKLI

181 LSVKSKNLNK DLSDMTNILQ QSELLLTNLN KKMGSYIYID TIKFIHKEMK HIFNRIEYHT

241 KIINDKTKII QDKIKLNIWR TFQKDELLKR ILDMSNEYSL FITSDHLRQM LYNTFYSKEK

301 HLNNIFHHLI YVLQMKFNDV PIKMEYFQTY KKNKPLTQ
```

PfRH5 Amino Acid Sequence (3D7) Excluding Signal Sequence, Flexible N-Terminal (Amino Acids 1 to 159) and Flexible Loop (Amino Acids 248 to 296) Regions: SEQ ID NO: 9

```
  1 SIDILQEKEG HLDFVIIPHY TFLDYYKHLS YNSIYHKSST YGKCIAVDAF IKKINEAYDK

61 VKSKCNDIKN DLIATIKKLE HPYDINNKNR AFKKMMDEYN TKKKKLIKCI KNHENDFNKI

121 CMDMKNYGTN LFEQLSCYNN NFCNTNGIRY HYDEYIHKLI LSVKSKNLNK DLSDMTNILQ

181 QSELLLTNLN KKMGSYIYID TIKFIHKEMK HIFNRIEYHT KIINDKTKII QDKIKLNIWR

241 TFQKDELLKR ILDMSNEYSL FITSDHLRQM LYNTFYSKEK HLNNIFHHLI YVLQMKFNDV

301 PIKMEYFQTY KKNKPLTQ
```

PfRH5 Amino Acid Sequence (7G8) Excluding Signal Sequence, Flexible N-Terminal (Amino Acids 1 to 159) and Flexible Loop (Amino Acids 248 to 296) Regions: SEQ ID NO: 10

```
  1 SIDILQEKEG HLDFVIIPHY TFLDYYKHLS YNSIYHKSST YGKYIAVDAF IKKINEAYDK

61 VKSKCNDIKN DLIATIKKLE HPYDINNKNR AFKKMMDEYN TKKKKLIKCI KNHENDFNKI

121 CMDMKNYGTN LFEQLSCYNN NFCNTNGIRY HYDEYIHKLI LSVKSKNLNK DLSDMTNILQ

181 QSELLLTNLN KKMGSYIYID TIKFIHKEMK HIFNRIEYHT KIINDKTKII QDKIKLNIWR

241 TFQKDELLKR ILDMSNEYSL FITSDHLRQM LYNTFYSKEK HLNNIFHHLI YVLQMKFNDV

301 PIKMEYFQTY KKNKPLTQ
```

Sv2 Vaccine Sequence Based on 3D7 Sequence Lacking Flexible N-Terminal Region (Amino Acids 1 to 139) and Comprising a Hexa-Histidine C-Terminal Tag (Dash-Underlined) and Bip Leader Sequence (Underlined): SEQ ID NO: 11

```
  1 MKLCILLAVV AFVGLSLGKN VNFLQYHFKE LSNYNIANSI DILQEKEGHL DFVIIPHYTF

61 LDYYKHLSYN SIYHKSSTYG KCIAVDAFIK KINEAYDKVK SKCNDIKNDL IATIKKLEHP

121 YDINNKNDDS YRYDISEEID DKSEETDDET EEVEDSIQDT DSNHAPSNKK KNDLMNRAFK

181 KMMDEYNTKK KKLIKCIKNH ENDFNKICMD MKNYGTNLFE QLSCYNNNFC NTNGIRYHYD

241 EYIHKLILSV KSKNLNKDLS DMTNILQQSE LLLTNLNKKM GSYIYIDTIK FIHKEMKHIF

301 NRIEYHTKII NDKTKIIQDK IKLNIWRTFQ KDELLKRILD MSNEYSLFIT SDHLRQMLYN

361 TFYSKEKHLN NIFHHLIYVL QMKFNDVPIK MEYFQTYKKN KPLTQHHHHH H
```

Sv2 Vaccine Sequence Based on 7G8 Sequence Lacking Flexible N-Terminal Region (Amino Acids 1 to 139) and Comprising a Hexa-Histidine C-Terminal Tag (Dash-Underlined) and Bip Leader Sequence (Underlined): SEQ ID NO: 12

```
  1 MKLCILLAVV AFVGLSLGKN VNFLQYHFKE LSNYNIANSI DILQEKEGHL DFVIIPHYTF

61 LDYYKHLSYN SIYHKSSTYG KYIAVDAFIK KINEAYDKVK SKCNDIKNDL IATIKKLEHP

121 YDINNKNDDS YRYDISEEID DKSEETDDET EEVEDSIQDT DSNHAPSNKK NKDLMNRAFK

181 KMMDEYNTKK KKLIKCIKNH ENDFNKICMD MKNYGTNLFE QLSCYNNNFC NTNGIRYHYD

241 EYIHKLILSV KSKNLNKDLS DMTNILQQSE LLLTNLNKKM GSYIYIDTIK FIHKEMKHIF

301 NRIEYHTKII NDKTKIIQDK IKLNIWRRFQ KDELLKRILD MSNEYSLFIT SDHLRQMLYN

361 TFYSKEKHLN NIFHHLIYVL QMKFNDVPIK MEYFQTYKKN KPLTQHHHHH H
```

Sv3 Vaccine Sequence Based on 3D7 Sequence Lacking Flexible N-Terminal (Amino Acids 1 to 139) and Flexible Loop (Amino Acids 248 to 296) Regions and Comprising a Hexa-Histidine C-Terminal Tag (Dash-Underlined) and Bip Leader Sequence (Underlined): SEQ ID NO: 13

```
  1 MKLCILLAVV AFVGLSLGKN VNFLQYHFKE LSNYNIANSI DILQEKEGHL DFVIIPHYTF

61 LDYYKHLSYN SIYHKSSTYG KCIAVDAFIK KINEAYDKVK SKCNDIKNDL IATIKKLEHP

121 YDINNKNRAF KKMMDEYNTK KKKLIKCIKN HENDFNKICM DMKNYGTNLF EQLSCYNNNF

181 CNTNGIRYHY DEYIHKLILS VKSKNLNKDL SDMTNILQQS ELLLTNLNKK MGSYIYIDTI
```

-continued

```
241 KFIHKEMKHI FNRIEYHTKI INDKTKIIQD KIKLNIWRTF QKDELLKRIL DMSNEYSLFI

301 TSDHLRQMLY NITYSKEKHL NNIFHHLIYV LQMKFNDVPI KMEYFQTYKK NKPLTQHHHH

361 HH
```

Sv3 Vaccine Sequence Based on 7G8 Sequence Lacking Flexible N-Terminal (Amino Acids 1 to 139) and Flexible Loop (Amino Acids 248 to 296) Regions and Comprising a Hexa-Histidine C-Terminal Tag (Dash-Underlined) and Bip Leader Sequence (Underlined): SEQ ID NO: 14

```
  1 MKLCILLAVV AFVGLSLGKN VNFLQYHFKE LSNYNIANSI DILQEKEGHL DFVIIPHYTF

61 LDYYKHLSYN SIYHKSSTYG KYIAVDAFIK KINEAYDKVK SKCNDIKNDL IATIKKLEHP

121 YDINNKNRAF KKMMDEYNTK KKKLIKCIKN HENDFNKICM DMKNYGTNLF EQLSCYNNNF

181 CNTNGIRYHY DEYIHKLILS VKSKNLNKDL SDMTNILQQS ELLLTNLNKK MGSYIYIDTI

241 KFIHKEMKHI FNRIEYHTKI INDKTKIIQD KIKLNIWRTF QKDELLKRIL DMSNEYSLFI

301 TSDHLRQMLY NITYSKEKHL NNIFHHLIYV LQMKFNDVPI KMEYFQTYKK NKPLTQHHHH

361 HH
```

The invention claimed is:

1. A viral vector, RNA vaccine or DNA plasmid that expresses a PfRH5 antigen, wherein the antigen is a basigin-binding discontinuous fragment of PfRH5 which lacks (i) the flexible N-terminal region of PfRH5 corresponding to amino acid residues 1 to 139 of SEQ ID NO: 1 or 2; and (ii) the flexible loop region corresponding to amino acid residues 248 to 296 of SEQ ID NO: 1 or 2; optionally wherein said viral vector, RNA vaccine or DNA plasmid, which expresses the basigin-binding discontinuous fragment of PfRH5, further comprises a signal peptide; optionally wherein the signal peptide directs secretion from human cells; optionally wherein the signal peptide is a mammalian signal peptide from tissue plasminogen activator.

2. The viral vector, RNA vaccine or DNA plasmid of claim 1, wherein;
   (i) the viral vector, RNA vaccine or DNA plasmid further expresses one or more antigens selected from PfAMA1, PfEBA175, PfRH1, PfRH2a, PfRH2b, PfRH4 and/or PfAARP, or a fragment thereof; optionally wherein said fragment of PfRH5 antigen and one or more antigens selected from PfAMA1, PfEBA175, PfRH1, PfRH2a, PfRH2b, PfRH4 and/or PfAARP, or a fragment thereof, is expressed as a fusion protein; or
   (ii) the viral vector, RNA vaccine or DNA plasmid, is in combination with a viral vector, RNA vaccine or DNA plasmid that expresses one or more antigens selected from PfAMA1, PfEBA175, PfRH1, PfRH2a, PfRH2b, PfRH4 and/or PfAARP, or a fragment thereof.

3. The viral vector of claim 1, wherein the viral vector is a human or simian adenovirus, or a pox virus; optionally wherein the viral vector is an AdHu5, ChAd63, ChAdOX1, ChAdOX2 or modified vaccinia Ankara (MVA) vector.

4. The RNA vaccine or DNA plasmid of claim 1, wherein the RNA vaccine or DNA plasmid is capable of expression in an immunised mammalian cell; or wherein the DNA plasmid is capable of expression in a heterologous protein expression system.

5. A vaccine composition comprising the viral vector, and/or RNA vaccine and/or DNA plasmid of claim 1.

6. A vaccine composition comprising a Reticulocyte-binding protein Homologue 5 (PfRH5) antigen, wherein said antigen is a basigin-binding discontinuous fragment of PfRH5 which lacks (i) the flexible N-terminal region of PfRH5 corresponding to amino acid residues 1 to 139 of SEQ ID NO: 1 or 2; and (ii) the flexible loop region corresponding to amino acid residues 248 to 296 of SEQ ID NO: 1 or 2.

7. The vaccine composition of claim 6, wherein
   (i) said basigin-binding discontinuous fragment of PfRH5 includes a region of at least ten continuous amino acids that overlaps with amino acid residue 191 and/or amino acid residue 359 of SEQ ID NO: 1 or 2; and/or
   (ii) said basigin-binding discontinuous fragment of PtRH5 comprises at least amino acid residues:
   (a) 197 to 200, 350 to 362 and 447 to 449 of SEQ ID NO: 1 or 2;
   (b) 196, 197, 346 to 354 and 452 of SEQ ID NO: 1 or 2;
   (c) 205 to 212 and 331 to 342 of SEQ ID NO: 1 or 2; or
   (d) any combination thereof;
   wherein optionally said basigin-binding discontinuous fragment (ii) of PfRH5 is less than or equal to 360 amino acids in length.

8. The vaccine composition of claim 6, wherein:
   (i) said basigin-binding discontinuous fragment of PfRH5 has an amino acid other than T at residue 216 and/or residue 299 of SEQ ID NO: 1 or 2; and/or
   (ii) said vaccine composition induces antibodies that have a growth inhibitory activity (GIA) of at least 50% at a concentration of 10 mg/ml.

9. The vaccine composition of claim 6, wherein said basigin-binding discontinuous fragment of PfRH5 has at least 90% sequence identity to any one of SEQ ID NO: 7 to 10.

10. The vaccine composition of claim 6, wherein said basigin-binding discontinuous fragment of PfRH5 has at least 90% sequence identity to:
    (i) amino acid residues 140 to 247 and 297 to 526 of SEQ ID NO: 1 or 2, wherein optionally said basigin-binding discontinuous fragment of PfRH5 has the amino acid sequence of SEQ ID NO: 3 or 4; and/or
    (ii) SEQ ID NO: 11, 12, 13 or 14.

11. The vaccine composition of claim 6, wherein:
    (i) the vaccine composition further comprises one or more antigens selected from PfAMA1, PfEBA175, PfRH1, PfRH2a, PfRH2b, PfRH4 and/or PfAARP; and/or
    (ii) said basigin-binding discontinuous fragment of PfRH5 is in the form of a recombinant protein, a protein particle, a virus-like particle, a fusion protein, or a combination thereof;
    wherein optionally said vaccine composition further comprises a fusion of the basigin-binding discontinuous fragment of PfRH5 and one or more antigens selected from PfAMA1, PfEBA175, PfRH1, PfRH2a, PfRH2b, PfRH4 and/or PfAARP.

12. The vaccine composition of claim 8, wherein said basigin-binding discontinuous fragment of PfRH5 has the amino acid A at residue 216 and/or residue 299 of SEQ ID NO: 1 or 2.

13. The vaccine composition of claim 8, wherein said basigin-binding discontinuous fragment of PfRH5 has the amino acid A at residues 216 and 299 of SEQ ID NO: 1 or 2.

14. A method of (i) treating malaria in a subject; or (ii) immunizing a subject, comprising administering a therapeutically effective amount of the vaccine composition of claim 6 to the subject, wherein the PfRH5 antigen is a basigin-binding discontinuous PfRH5 fragment which results in antibodies with a growth inhibitory activity (GIA) of at least 50% against the blood-stage *Plasmodium* parasite.

15. The method of claim 14, wherein the treatment further comprises priming a subject with a human or simian adenovirus, for example AdHu5, ChAd63, ChAdOX1 or ChAdOX2; optionally wherein said treatment further comprises boosting a subject with a pox virus, for example MVA.

16. The method of claim 14, wherein (i) the PfRH5 antigen is a basigin-binding discontinuous PfRH5 fragment which results in antibodies with a growth inhibitory activity (GIA) of at least 50% against a plurality of genetic strains of the blood-stage *Plasmodium* parasite; and/or (ii) the *Plasmodium* parasite is *Plasmodium falciparum*.

\* \* \* \* \*